(12) United States Patent
Pompejus et al.

(10) Patent No.: US 9,109,244 B2
(45) Date of Patent: Aug. 18, 2015

(54) FERMENTATIVE PRODUCTION OF FINE CHEMICALS

(75) Inventors: Markus Pompejus, Seoul (KR); Stephan Freyer, Neustadt (DE); Markus Lohscheidt, Heidelberg (DE); Oskar Zelder, Speyer (DE); Matthias Boy, Langen (DE)

(73) Assignee: BASF SE, Ludwigshafen (DE)

( * ) Notice: Subject to any disclaimer, the term of this patent is extended or adjusted under 35 U.S.C. 154(b) by 1388 days.

(21) Appl. No.: 11/597,782

(22) PCT Filed: May 27, 2005

(86) PCT No.: PCT/EP2005/005728
§ 371 (c)(1),
(2), (4) Date: Nov. 27, 2006

(87) PCT Pub. No.: WO2005/116228
PCT Pub. Date: Dec. 8, 2005

(65) Prior Publication Data
US 2009/0162892 A1  Jun. 25, 2009

(30) Foreign Application Priority Data

May 28, 2004 (DE) .......... 10 2004 026 152

(51) Int. Cl.
| | |
|---|---|
| C12P 25/00 | (2006.01) |
| C12P 7/46 | (2006.01) |
| C12P 13/12 | (2006.01) |
| C12P 13/02 | (2006.01) |
| C12P 13/08 | (2006.01) |
| C12P 13/10 | (2006.01) |
| C12P 13/14 | (2006.01) |
| C12P 13/24 | (2006.01) |
| C12P 19/02 | (2006.01) |
| C12P 19/14 | (2006.01) |
| C12P 19/20 | (2006.01) |

(52) U.S. Cl.
CPC . *C12P 25/00* (2013.01); *C12P 7/46* (2013.01); *C12P 13/02* (2013.01); *C12P 13/08* (2013.01); *C12P 13/10* (2013.01); *C12P 13/12* (2013.01); *C12P 13/14* (2013.01); *C12P 13/24* (2013.01); *C12P 19/02* (2013.01); *C12P 19/14* (2013.01); *C12P 19/20* (2013.01)

(58) Field of Classification Search
CPC ............ A61K 2300/00; A61K 31/685; A61K 35/612; A61K 31/122; A61K 38/1709; A61K 31/401; A61K 36/48; A61K 38/1767; A61K 9/2009; A61K 9/2054; A61K 9/2866; A61K 31/133; A61K 31/198; A61K 31/202; A61K 31/575; A61K 31/661; Y02E 50/17; Y02E 50/16; A23V 2002/00; A23V 2200/08; A23V 2200/3204; A23V 2250/2132; A23V 2250/218; C12P 7/06; C12P 7/48; G01N 2021/8416; G01N 2021/8592; G01N 2030/8854; G01N 2030/8886; G01N 21/274
See application file for complete search history.

(56) References Cited

U.S. PATENT DOCUMENTS

| | | | |
|---|---|---|---|
| 3,787,587 A | 1/1974 | Weber | |
| 4,306,023 A | 12/1981 | Crombie | |
| 4,889,921 A * | 12/1989 | Diosady et al. | ............... 530/377 |
| 5,431,933 A | 7/1995 | Binder et al. | |
| 5,770,409 A | 6/1998 | Pfefferle et al. | |
| 5,840,358 A | 11/1998 | Höfler et al. | |
| 2002/0079268 A1 | 6/2002 | Caboche et al. | |
| 2003/0087002 A1 | 5/2003 | Fouache et al. | |
| 2004/0002142 A1 | 1/2004 | Nielsen et al. | |
| 2004/0113551 A1 | 6/2004 | Klein et al. | |

FOREIGN PATENT DOCUMENTS

| | | |
|---|---|---|
| CN | 1173541 | 2/1998 |
| CN | 1218111 | 6/1999 |

(Continued)

OTHER PUBLICATIONS

Beukema, K.J. et al., "Production of Fermentation Syrups by Enzymatic Hydrolysis of Potatoes," *Biotechnological Research in the Netherlands*, Programme and Poster Abstract, No. A.2 (1983).
de Menezes, T.J.B., "Fungal celluloses as an aid for the saccharification of Cassava," *Biotechnology and Bioengineering*, John Wiley & Sons, Ed. Elmer L. Gaden, Jr., vol. 20(4):557-558 (1978).

(Continued)

*Primary Examiner* — Debbie K Ware
(74) *Attorney, Agent, or Firm* — Drinker Biddle & Reath LLP

(57) ABSTRACT

The invention relates to a process for the production of at least one microbial metabolite having at least 3 carbon atoms or at least 2 carbon atoms and at least 1 nitrogen atom by means of sugar-based microbial fermentation, comprising:
a) the preparation of a sugar-containing liquid medium with a monosaccharide content of more than 20% by weight from a starch feedstock, the sugar-containing liquid medium also comprising non-starchy solid constituents of the starch feedstock;
b) the fermentation of the sugar-containing liquid medium for the production of the metabolite(s); and
c) depletion or isolation of at least one metabolite from the fermentation liquor,
wherein a microorganism strain which produces the desired metabolite(s) is cultivated with the sugar-containing liquid medium, said liquid medium being obtained by:
a1) milling the starch feedstock; and
a2) liquefying the millbase in an aqueous liquid in the presence of at least one starch-liquefying enzyme, followed by saccharification using at least one saccharifying enzyme, where at least some of the millbase is liquefied by continuous or batchwise addition to the aqueous liquid.

22 Claims, No Drawings

(56) References Cited

FOREIGN PATENT DOCUMENTS

| | | |
|---|---|---|
| CN | 1266102 | 9/2000 |
| DE | 31 46 558 A1 | 6/1983 |
| DE | 195 19 270 A1 | 12/1996 |
| EP | 0532867 A1 | 3/1993 |
| EP | 0809940 A2 | 12/1997 |
| EP | 1 205 557 A1 | 5/2002 |
| EP | 1205557 A1 | 5/2002 |
| EP | 1 308 505 A2 | 5/2003 |
| EP | 1308505 A2 | 5/2003 |
| JP | 56-169594 | 12/1981 |
| JP | 56169594 A | 12/1981 |
| JP | 57-159500 | 10/1982 |
| JP | 11-501813 A | 2/1999 |
| JP | 2001-72701 | 3/2001 |
| JP | 2001-275693 | 10/2001 |
| JP | 2001-309751 | 11/2001 |
| JP | 2003-528602 | 9/2003 |
| NL | 8302229 | 1/1985 |
| RU | 2081166 C1 | 6/1997 |
| RU | 2090614 C1 | 9/1997 |
| WO | WO 96/28567 A1 | 9/1996 |
| WO | WO-01/72689 A2 | 10/2001 |
| WO | WO-02/077252 A1 | 10/2002 |
| WO | WO-03/095659 A1 | 11/2003 |
| WO | WO-2004/113551 A1 | 12/2004 |

OTHER PUBLICATIONS de Menezes, T.J.B., "Saccharification of Cassava for Ethyl Alcohol Production," *Process Biochemistry*, vol. 13(9):24, 26 (1978).
Mersmann, Alfons et al, "Selection and Design of Aerobic Bioreactors," *Chem. Eng. Technol.*, vol. 13:357-370 (1990).
Pfefferle, Walter et al, "Biotechnological Manufacture of Lysine," *Advances in Biochemical Engineering/Biotechnology*, vol. 79:59-112 (2003).
International Search Report for Application No. PCT/EP2005/005728, dated Mar. 3, 2006.
Göksungur, Y., et al., "Enzymatic Hydrolysis and Production of Ethanol From Potato Starch", GIDA, vol. 19, No. 2, (1994), pp. 89-92.
Nigam, P, et al., "Enzyme and Microbial Systems Involved in Starch Processing", Enzyme and Microbial Technology, vol. 17, (1995), pp. 770-778.
Excerpt from ROMPP Online regarding grain, Version 3.9, downloaded Nov. 24, 2010 from http://www.roempp.com/prod/roempp.php. (Translation attached).
Partial Translation of Excerpt from ROMPP Online regarding grain, Version 3.9, downloaded Nov. 24, 2010 from http://www.roempp.com/prod/roempp.php.
Excerpt from Wikipedia regarding by-product formation during alcoholic fermentation (Translation attached), downloaded Dec. 13, 2010 from http://de.wikipedia.org/wiki/Begleitalkohol, 3 pages.
Partial translation of Excerpt from Wikipedia regarding by-product formation during alcoholic fermentation (Translation attached), downloaded Dec. 13, 2010 from http://de.wikipedia.org/wiki/Begleitalkohol, 1 page.
"Bioethanol-Produktionsverfahren" of CropEnergies AG, (Translation attached), Aug. 6, 2009, 4 pages.
Partial translation of "Bioethanol-Produktionsverfahren" of CropEnergies Ag, Aug. 6, 2009, 1 page.
Stryer, L., "Monosaccharides are Aldehydes or Ketones with Multiple Hydroxyl Groups", in Biochemistry, third edition, 1975, pp. 332-333.
Tegge, G., "8.2 Enzymkatalysierte Hyrdyse", Starke and Starkederivate, Behr's Verlag (Hamburg), (2006), pp. 238-259.

\* cited by examiner

FERMENTATIVE PRODUCTION OF FINE CHEMICALS

RELATED APPLICATIONS

The present application is a 35 U.S.C. 371 national stage filing of International Application No. PCT/EP2005/005728, filed May 27, 2005, which claims priority to German Application No. 10 2004 026152.0, filed May 28, 2004. The entire contents of each of these applications are hereby incorporated by reference herein.

DESCRIPTION OF THE INVENTION

The present invention relates to the fermentative production of fine chemicals by grinding, liquefying and saccharifying starch feedstocks and to the use of the resulting sugar solution as fermentation medium.

Fermentative processes for the production of fine chemicals such as, for example, amino acids, vitamins and carotenoids by means of microorganisms are generally known. Depending on the various process conditions, they exploit different carbon feedstocks. They extend from pure sucrose via beet and sugarcane molasses to what are known as high-test molasses (inverted sugarcane molasses) to glucose from starch hydrolyzates. Moreover, acetic acid and ethanol are mentioned as cosubstrates which can be employed on an industrial scale for the biotechnological production of L-lysine (Pfefferle et al., Biotechnological Manufacture of Lysine, Advances in Biochemical Engineering/Biotechnology, Vol. 79 (2003), 59-112).

Based on the abovementioned carbon feedstocks, various methods and procedures for the sugar-based, fermentative production of fine chemicals are established. Taking L-lysine as an example, these are described for example by Pfefferle et al. (loc. cit.) with regard to strain development, process development and industrial production.

An important carbon feedstock for the microorganism-mediated fermentative production of fine chemicals is starch. The latter must first be liquefied and saccharified in preceding reaction steps before it can be exploited as carbon feedstock in a fermentation. To this end, the starch is usually obtained in pre-purified form from a natural starch feedstock such as potatoes, cassava, cereals, for example wheat, corn, barley, rye, triticale or rice, and subsequently enzymatically liquefied and saccharified, whereafter it is employed in the actual fermentation for producing the fine chemicals.

In addition to the use of such pre-purified starch feedstocks, the use of non-pretreated starch feedstocks for the preparation of carbon feedstocks for the fermentative production of fine chemicals has also been described. Typically, the starch feedstocks are initially comminuted by grinding. The millbase is then subjected to liquefaction and saccharification. Since this millbase naturally comprises, besides starch, a series of nonstarchy constituents which adversely affect the fermentation, these constituents are usually removed prior to fermentation. The removal can be effected either directly after grinding (WO 02/277252; JP 2001-072701; JP 56-169594; CN 1218111), after liquefaction (WO 02/277252; CN 1173541) or subsequently to saccharification (CN 1266102; Beukema et al.: Production of fermentation syrups by enzymatic hydrolysis of potatoes; potato saccharification to give culture medium (Conference Abstract), Symp. Biotechnol. Res. Neth. (1983), 6; NL8302229). However, all variants involve the use of a substantially pure starch hydrolyzate in the fermentation.

More recent techniques deal in particular with improved methods which are intended to make possible a purification, for example of liquefied and saccharified starch solutions (JP 57159500) and of fermentation media from renewable resources (EP 1205557) prior to fermentation.

Unprocessed starch feedstocks, in contrast, are known to be employed on a large scale in the fermentative production of bioethanol. Here, the method known as "dry milling", liquefaction and saccharification of starch feedstocks is established on a large industrial scale. Suitable process descriptions can be found for example in "The Alcohol Textbook—A reference for the beverage, fuel and industrial alcohol industries", Jaques et al. (ed.), Nottingham Univ. Press 1995, ISBN 1-8977676-735 and in McAloon et al., "Determining the cost of producing ethanol from corn starch and lignocellulosic feedstocks", NREL/TP-580-28893, National Renewable Energy Laboratory, October 2000.

In the first step of the dry-milling method, whole cereal kernels, preferably corn, wheat, barley, millet and rye, are ground finely. In contrast to what is known as the wet-milling method, no additional liquid is added. The purpose of grinding the material into fine constituents is to make the starch present in the kernels accessible to the effect of water and enzymes in the subsequent liquefaction and saccharification.

Since in the fermentative production of bioethanol the product of value is obtained by distillation, the use of starch feedstocks from the dry-milling process in non-pre-purified form does not constitute a particular problem. However, when using a dry-milling method for the production of fine chemicals, the solids stream introduced into the fermentation via the sugar solution is problematic since it not only may have an adverse effect on the fermentation, but also makes the subsequent processing substantially more difficult.

Thus, the oxygen supply for the microorganisms employed is a limiting factor in many fermentations, in particular when the former have demanding oxygen requirements. In general, little is known about the effect of high solids concentrations on the transition of oxygen from the gas phase into the liquid phase, and thus on the oxygen transfer rate. On the other hand, it is known that a viscosity which increases with increasing solids concentrations leads to a reduced oxygen transfer rate. If, moreover, surface-active substances are introduced into the fermentation medium together with the solids, they affect the tendency of the gas bubbles to coagulate. The resulting bubble size, in turn, has a substantial effect on oxygen transfer (Mersmann, A. et al.: Selection and Design of Aerobic Bioreactors, Chem. Eng. Technol. 13 (1990), 357-370).

As the result of the introduction of solids, a critical viscosity value of the media used can be reached as early as during the preparation of the starch-containing suspension since, for example, a suspension with more than 30% by weight of ground corn in water can no longer be mixed homogeneously (Industrial Enzymology, 2nd ed., T. Godfrey, S. West, 1996). This limits the glucose concentration in conventional procedures. As a result, it is disadvantageous for process economical reasons to use solutions with a lower concentration since this results in a disproportionate dilution of the fermentation liquor. This causes the achievable final concentration of the target products to drop, which results in additional costs when these are isolated, and the space-time yield decreases, which, given an equal production quantity, leads to a higher volume requirement, i.e. higher investment costs.

During work-up, the increased solids concentration may result in particular difficulties for the use of specific methods. Thus, for example, when purifying the fermentation liquor by means of ion-exchange chromatography, it must be taken into consideration that the chromatography column employed tends to clogging (i.e. blockage).

Owing to these difficulties, prior-art variants of the dry-milling method are not suitable for providing starch feedstock for the fermentative production of fine chemicals and are therefore without particular economical importance. To date, attempts to apply the dry-milling concept and the advantages which exist in principle in connection with this method, to the industrial-scale production of fine chemicals have only been described using cassava as starch feedstock.

Thus, while JP 2001/275693 describes a method for the fermentative production of amino acids in which peeled cassava tubers which have been ground in the dry state are employed as starch feedstock, it is necessary, to carry out the process, to adjust the particle size of the millbase at ≤150 µm. In the filtration step which is employed for this purpose, more than 10% by weight of the millbase employed, including non-starch-containing constituents, are removed before the starch obtained is liquefied/saccharified and subsequently fermented. Moreover, the method dispenses with the problem of removing non-starch-containing constituents in as far as the fermentation products, for example lysine, are intended to be used as feed additive and the non-starch-containing cassava constituents may thus remain in the product of value.

A similar method is described in JP 2001/309751 for the production of an amino-acid-containing feed additive. Analogously, a purification, or removal of solids, is not required.

However, cassava should be relatively problem-free in relation to the dry-milling process in comparison with other starch feedstocks. While the starch typically accounts for at least 80% by weight of the dry cassava root (Menezes et al., Fungal celluloses as an aid for the saccharification of Cassava, Biotechnology and Bioengineering, Vol. 20 (4), 1978, John Wiley and Sons, Inc., Table 1, page 558), the starch content (dry matter) in cereal is comparatively much lower, generally below 70% by weight, for example it amounts to approximately 68% by weight in the case of corn and to approximately 65% by weight in the case of wheat (Jaques et al., The Alcohol Textbook, ibid.). Accordingly, the glucose solution obtained after liquefaction and saccharification comprises fewer contaminants, in particular fewer solids, when employing dry-milled cassava than when employing another dry-milled starch feedstock.

An increased amount of contaminations increases the viscosity of the reaction mixture. Cassava starch, however, should be relatively easy to process. While it has a higher viscosity at the swelling temperature in comparison with corn starch, the viscosity, in contrast, drops more rapidly at increasing temperatures than in the case of corn starch (Menezes, T. J. B. de, Saccharification of Cassava for ethyl alcohol production, Process Biochemistry, 1978, page 24, right column). Moreover, the swelling and gelatinization temperatures of cassava starch are lower than those of starch from cereals such as corn, which is why it is more readily accessible to bacterial α-amylase than cereal starch (Menezes, T. J. B. de, loc. cit.).

Further advantages of cassava over other starch feedstocks are its low cellulose content and its low phytate content. Cellulose and hemicellulose can be converted into furfurals, in particular under acidic saccharification conditions (Jaques et al., The Alcohol Textbook, ibid.; Menezes, T. J. B. de, ibid.) which, in turn, may have an inhibitory effect on the microorganisms employed in the fermentation. Phytate likewise inhibits the microorganisms employed for the fermentation.

While it is thus possible, from a technical aspect, to process cassava as starch feedstock in a process which corresponds to the dry-milling process, such a cassava-based process is still complex, not optimized and therefore not widely used.

It was thus an object of the present invention to provide an efficient process for the fermentative production of fine chemicals which permits the use of a multiplicity of starch-containing, worldwide locally available plants, for example cereals or potatoes, as starch feedstock. The process was to be distinguished by easy handling of the media used and was to avoid, in particular, complicated pre-purification or main purification steps, such as, for example, the removal of solid non-starch-containing constituents, prior to fermentation. Moreover, it was to allow easy processing of the fermentation mixture. In connection with work carried out by the applicant company, it has been found, surprisingly, that such a process can be carried out in an efficient manner, despite the inherently increased introduction of solids.

The invention thus relates to a process for the production of at least one microbial metabolite having at least 3 carbon atoms, or having at least 2 carbon atoms and at least 1 nitrogen atom by means of sugar-based microbial fermentation, comprising:

a) the preparation of a sugar-containing liquid medium with a monosaccharide content of more than 20% by weight from a starch feedstock, the sugar-containing liquid medium also comprising non-starch-containing solid constituents of the starch feedstock;

b) the fermentation of the sugar-containing liquid medium for the production of the metabolite(s); and c) depletion or isolation of at least one metabolite from the fermentation liquor, which comprises culturing, with the sugar-containing liquid medium, a microorganism strain which produces the desired metabolite(s), which liquid media is obtained by:

a1) milling the starch feedstock; and a2) liquefying the millbase in an aqueous liquid in the presence of at least one starch-liquefying enzyme, followed by saccharification using at least one saccharifying enzyme, where at least some of the millbase is liquefied by continuous or batchwise addition to the aqueous liquid.

Suitable as starch feedstock are, mainly, dry grains or seeds where the starch amounts to at least 40% by weight and preferably at least 50% by weight in the dried state. They are found in many of the cereal plants which are currently grown on a large scale, such as corn, wheat, oats, barley, rye, triticale, rice and various sorghum and millet species, for example sorgo and milo. The starch feedstock is preferably selected from among cereal kernels, especially preferably among corn, rye, triticale and wheat kernels. In principle, the process according to the invention can also be carried out with other starch feedstocks such as, for example, potatoes, cassava/tapioca or a mixture of various starch-containing fruits or seeds.

The sugars present in the sugar-containing liquid medium are preferably monosaccharides such as hexoses and pentoses, for example glucose, fructose, mannose, galactose, sorbose, xylose, arabinose and ribose, in particular glucose. The amount of monosaccharides other than glucose can vary, depending on the starch feedstock used and the non-starchy constituents present therein; it may be affected by the conduct of the reaction, for example by the decomposition of cellulose constituents by addition of cellulases. The monosaccharides of the sugar-containing liquid medium advantageously comprise glucose in an amount of at least 60% by weight, preferably at least 70% by weight, especially preferably at least 80% by weight, based on the total amount of sugars present in the sugar-containing liquid medium. Usually, the glucose amounts to in the range of from 75 to 99% by weight, in particular from 80 to 97% by weight and specifically from 85 to 95% by weight, based on the total amount of sugars present in the sugar-containing liquid medium.

In accordance with the invention, the sugar-containing liquid medium with which the microorganism strain producing the desired metabolic products is cultured comprises at least some, preferably at least 20% by weight, in particular at least 50% by weight, specifically at least 90% by weight and very specifically at least 99% by weight of the nonstarchy solid constituents which are present in the milled cereal kernels, depending on the extraction rate. Based on the starchy constituents of the mill base (and thus on the amount of monosaccharide in the sugar-containing liquid medium), the nonstarchy solid constituents in the sugar-containing liquid medium preferably account for at least 10% by weight and in particular at least 25% by weight, for example between 25 and 75% by weight and specifically between 30 and 60% by weight.

To prepare the sugar-containing liquid medium, the starch feedstock in question is milled in step a1), with or without addition of liquid, for example water, preferably without addition of liquid. It is also possible to combine dry milling with a subsequent wet-milling step. Apparatuses which are typically employed for dry milling are hammer mills, rotor mills or roller crushers; those which are suitable for wet grinding are paddle mixers, agitated ball mills, circulation mills, disk mills, annular chamber mills, oscillatory mills or planetary mills. In principle, other mills are also suitable. The amount of liquid required for wet grinding can be determined by the skilled worker in routine experiments. It is usually adjusted in such a way that the dry matter content is in the range of from 10 to 20% by weight.

Grinding brings about a particle size which is suitable for the subsequent process steps. In this context, it has proved advantageous when the millbase obtained in the milling step, in particular the dry milling step, in step a1) has flour particles, i.e. particulate constituents, with a particle size in the range of from 100 to 630 μm in an amount of from 30 to 100% by weight, preferably 40 to 95% by weight and especially preferably 50 to 90% by weight. Preferably, the millbase obtained comprises 50% by weight of flour particles with a particle size of more than 100 μm. As a rule, at least 95% by weight of the flour particles obtained have a particle size of less than 2 mm. In this context, the particle size is measured by means of screen analysis using a vibration analyzer. In principle, a small particle size is advantageous for obtaining a high product yield. However, an unduly small particle size may result in problems, in particular problems due to clump formation/agglomeration, when the millbase is slurried during liquefaction or processing, for example during drying the solids after the fermentation step.

Usually, flours are characterized by the extraction rate or by the flour grade, whose correlation with one another is such that the characteristic of the flour grade increases with increasing extraction rate. The extraction rate corresponds to the amount by weight of the flour obtained based on 100 parts by weight of millbase applied. While, during the milling process, pure, ultrafine flour, for example from the interior of the cereal kernel, is initially obtained, the amount of crude fiber and husk content in the flour increases, while the proportion of starch decreases. The extraction rate is therefore also reflected in what is known as the flour grade, which is used as a figure for classifying flours, in particular cereal flours, and which is based on the ash content of the flour (known as ash scale). The flour grade or type number indicates the amount of ash (minerals) in mg which is left behind when 100 g of flour solids are incinerated. In the case of cereal flours, a higher type number means a higher extraction rate since the core of the cereal kernel comprises approximately 0.4% by weight of ash, while the husk comprise approximately 5% by weight of ash. In the case of a lower extraction rate, the cereal flours thus consist predominantly of the comminuted endosperm, i.e. the starch content of the cereal kernels; in the case of a higher extraction rate, the cereal flours also comprise the comminuted, protein-containing aleurone layer of the grains; in the case of coarse mill, they also comprise the constituents of the protein-containing and fat-containing embryo and of the husks, which comprise raw fiber and ash. For the purposes of the invention, flours with a high extraction rate, or a high type number, are preferred in principle. If cereal is employed as starch feedstock, it is preferred that the intact kernels together with their husks are milled and processed.

If appropriate, the starch feedstock will, prior to milling, be comminuted to a size which is suitable for milling, for example when using relatively large materials such as potatoes or cassava. In the case of cereals, this comminution step can be dispensed with, and the intact kernel is employed and milled.

To liquefy the starch present in the millbase, at least some of the millbase, preferably at least 40% by weight, in particular at least 50% by weight and very especially preferably at least 55% by weight, are introduced, in step a2), into the reactor in the course of the liquefaction step, but before the saccharification step. Frequently, the added amount will not exceed 90% by weight, in particular 85% by weight and especially preferably 80% by weight. Preferably, this part of the millbase which is added in the course of the process is supplied to the reactor under conditions as prevail during the liquefaction step. The addition can be effected batchwise, i.e. portionwise, in several portions which preferably in each case do not amount to more than 20% by weight, especially preferably not more than 10% by weight, for example 1 to 20% by weight, in particular 2 to 10% by weight, of the total amount of the millbase to be liquefied, or else continuously. It is essential for the invention that only some of the millbase, preferably not more than 60% by weight, in particular not more than 50% by weight and especially preferably not more than 45% by weight of the millbase are present in the reactor at the beginning of the liquefaction process and that the remainder of the millbase is added during the liquefaction step. The liquefaction can also be carried out continuously, for example in a multi-step reaction cascade.

In accordance with the invention, the liquefaction in step a2) is carried out in the presence of at least one starch-liquefying enzyme which is preferably selected from the α-amylases. Other enzymes which are active and stable under the reaction conditions and which liquefy stable starch can likewise be employed.

The α-amylase (or the starch-liquefying enzyme used) can be introduced first into the reaction vessel or added in the course of step a2). Preferably, some of the α-amylase required in step a2) is added at the beginning of step a2) or is first placed into the reactor. The total amount of α-amylase is usually in the range of from 0.002 to 3.0% by weight, preferably from 0.01 to 1.5% by weight and especially preferably from 0.02 to 0.5% by weight, based on the total amount of starch feedstock employed.

The liquefaction can be carried out above or below the gelling temperature. Preferably, the liquefaction in step a2) is carried out at least in part above the gelling temperature of the starch employed (known as the cooking process). As a rule, a temperature in the range of between 70 and 165° C., preferably between 80 and 125° C. and especially preferably between 85 and 115° C. is chosen, the temperature preferably being at least 5° C. and especially preferably at least 10° C. above the gelling temperature.

To achieve an optimal α-amylase activity, step a2) is preferably at least in part carried out at a pH in the weakly acidic range, preferably between 4.0 and 7.0, especially preferably between 5.0 and 6.5, the pH usually being adjusted before or at the beginning of step a2); preferably, this pH is checked during the liquefaction and, if appropriate, readjusted. The pH is preferably adjusted using dilute mineral acids such as $H_2SO_4$ or $H_3PO_4$, or dilute alkali hydroxide solutions such as NaOH or KOH.

In a preferred embodiment, step a2) of the process according to the invention is carried out in such a way that a portion amounting to not more than 60% by weight, preferably not more than 50% by weight and especially preferably not more than 45% by weight, for example 10 to 60% by weight, in particular 15 to 50% by weight, and especially preferably 20 to 45% by weight, based on the total amount of millbase, is initially suspended in an aqueous liquid, for example fresh water, recirculated process water, for example from the fermentation or the processing stages, or in a mixture of these liquids, and the liquefaction is subsequently carried out.

To carry out the method according to the invention, it is possible to preheat the liquid used for generating the suspension to a moderately increased temperature, for example in the range of from 40 to 60° C. However, it is preferred to employ the liquids at room temperature.

Then, the at least one starch-liquefying enzyme, preferably an α-amylase, is added to this suspension. If an α-amylase is used, it is advantageous only to add some of the α-amylase, for example 10 to 70% by weight, in particular 20 to 65% by weight, based on all of the α-amylase employed in step a2). The amount of α-amylase added at this point in time depends on the activity of the α-amylase in question under the reaction conditions with regard to the starch feedstock used and is generally in the range of from 0.0004 to 2.0% by weight, preferably from 0.001 to 1.0% by weight and especially preferably from 0.02 to 0.3% by weight, based on the total amount of the starch feedstock employed. As an alternative, the α-amylase portion can be mixed with the liquid used before the suspension is made.

In this context, the α-amylase portion is preferably added before heating to the temperature used for the liquefaction has started, in particular at room temperature or only moderately increased temperature, for example in the range of from 20 to 30° C.

Advantageously, the amounts of α-amylase and millbase will be selected in such a way that the viscosity during the gelling process is sufficiently reduced in order to make possible effective mixing of the suspension, for example by means of stirring. Preferably, the viscosity of the reaction mixture during gelling amounts to not more than 20 Pas, especially preferably not more than 10 Pas and very especially preferably not more than 5 Pas. As a rule, the viscosity is measured using a Haake viscometer type Roto Visko RV20 with M5 measuring system and MVDIN instrumentation at a temperature of 50° C. and a shear rate of 200 $s^{-1}$.

The suspension thus made is then heated, preferably at a temperature above the gelling temperature of the starch used. As a rule, a temperature in the range of between 70 and 165° C., preferably between 80 and 125° C. and especially preferably between 85 and 115° C. is chosen, the temperature preferably being at least 5° C. and especially preferably at least 10° C. above the gelling temperature. While monitoring the viscosity, further portions of the starch feedstock, for example in each case 2 to 20% by weight and in particular from 5 to 10% by weight, based on all of the starch employed, are added gradually to the starch-containing suspension. It is preferred to add the portion of the millbase to be added in the course of the liquefaction step in at least 2, preferably at least 4 and especially preferably at least 6 fractions to the reaction mixture. As an alternative, the portion of the millbase which has not employed for making the suspension can be added continuously during the liquefaction step. During the addition, the temperature should advantageously be kept above the gelling temperature of the starch.

After all of the flour has been added, the reaction mixture is usually held for a certain period of time, for example 30 to 60 minutes or longer, if necessary, at the temperature set above the gelling temperature of the starch, i.e. cooked. Then, the reaction mixture is, as a rule, cooled to a temperature slightly less above the gelling temperature, for example 75 to 90° C., before a further α-amylase portion, preferably the main portion, is added. Depending on the activity under the reaction conditions of the α-amylase used, the amount of α-amylase added at this point in time is preferably 0.002 to 2.0% by weight, especially preferably from 0.01 to 1.0% by weight and very especially preferably from 0.02 to 0.4% by weight, based on the total amount of the starch feedstock employed.

At these temperatures, the granular structure of the starch is destroyed (gelling), making possible the enzymatic degradation of the latter. To fully degrade the starch into dextrins, the reaction mixture is held at the set temperature, or, if appropriate, heated further, until the detection of starch by means of iodine or, if appropriate, another test for detecting starch is negative or at least essentially negative. If appropriate, one or more further α-amylase portions, for example in the range of from 0.001 to 0.5% by weight and preferably from 0.002 to 0.2% by weight, based on the total amount of the starch feedstock employed, may now be added to the reaction mixture.

After the starch liquefaction has ended; the dextrins present in the liquid medium are saccharified, i.e. broken down into glucose, either continuously or batchwise, preferably continuously. The liquefied medium can be saccharified continuously in a specific saccharification tank before being fed into the fermentation step (b). On the other hand, it has proved advantageous to carry out only a partial saccharification before the fermentation. For example, a procedure can be followed in which a portion of the dextrins present in the liquid medium, for example in the range of from 10 to 90% by weight and in particular in the range of from 20 to 80% by weight, based on the total weight of the dextrins (or of the original starch) is saccharified and the resulting sugar-containing liquid medium is employed in the fermentation. A further saccharification can then be carried out in situ in the fermentation medium. The saccharification can furthermore be carried out directly in the fermenter (in situ), dispensing with a separate saccharification tank.

Advantages of the in-situ saccharification, i.e. of a saccharification which is in part or fully carried out in the fermenter, is firstly reduced capital expenditure; secondly, the delayed release of the glucose may allow a higher glucose concentration to be provided initially with the batch without inhibition or metabolic changes of the microorganisms employed taking place. In the case of *E. coli* for example, an unduly high glucose concentration leads to the formation of organic acids (acetate), while *Saccharomyces cerevisiae*, for example, switches to fermentation in such a case, although sufficient oxygen is present in aerated fermenters (Crabtree effect). A delayed release of glucose can be adjusted by controlling the glucoamylase concentration. By doing so, it is possible to suppress the abovementioned effects, and more substrate can be provided initially so that the dilution resulting from the feed stream provided can be reduced.

In the case of saccharification in a saccharification tank, the liquefied starch solution is usually chilled or warmed to the temperature optimum of the saccharifying enzyme or slightly below, for example to 50 to 70° C., preferably 60 to 65° C., and subsequently treated with glucoamylase.

If the saccharification is carried out in the fermenter, the liquefied starch solution will, as a rule, be cooled to fermentation temperature, i.e. 32 to 37° C., before it is fed into the fermenter. In this case, the glucoamylase (or the at least one saccharifying enzyme) for the saccharification is added directly to the fermentation liquor. The saccharification of the liquefied starch in accordance with step a2) now takes place in parallel with the metabolization of the sugar by the microorganisms as described in step b).

Prior to addition of the glucoamylase, the pH of the liquid medium is advantageously adjusted to a value in the optimal activity range of the glucoamylase employed, preferably in the range of between 3.5 and 6.0; especially preferably between 4.0 and, 5.5 and very especially preferably between 4.0 and 5.0. However, in particular when carrying out the saccharification directly in the fermenter, it is also possible to adjust the pH to a value outside the abovementioned ranges, for example in the range of from 6.0 to 8.0. This may generally be advantageous, or required as a result of the fermentation conditions to be established, for example in the preparation of lysin, pantothenate and vitamin $B_2$, despite the limited activity of standard glucoamylases in the pH range.

In a preferred embodiment, the saccharification is carried out in a specific saccharification tank. To this end, the liquefied starch solution is warmed to a temperature which is optimal for the enzyme, or slightly below, and the pH is adjusted in the above-described manner to a value which is optimal for the enzyme.

Usually, the glucoamylase is added to the dextrin-containing liquid medium in an amount of from 0.001 to 5.0% by weight, preferably from 0.005 to 3.0% by weight and especially preferably from 0.01 to 1.0% by weight, based on the total amount of the starch feedstock employed. After addition of the glucoamylase, the dextrin-containing suspension is preferably held for a period of, for example 2 to 72 hours or longer, if required, in particular 5 to 48 hours, at the set temperature, the dextrins being saccharified to give monosaccharides. The progress of the saccharification process can be monitored using methods known to the skilled worker, for example HPLC, enzyme assays or glucose test strips. The saccharification is complete when the monosaccharide concentration no longer rises substantially, or indeed drops.

In a preferred embodiment, the discontinuous or continuous addition, preferably the discontinuous and in particular portionwise addition, of the millbase in the presence of the at least one α-amylase and the at least one glucoamylase in step a2) is carried out in such a way that the viscosity of the liquid medium is not more than 20 Pas, preferably not more than 10 Pas and especially preferably not more than 5 Pas. To aid the control of the viscosity, it has proved advantageous to add at least 25% by weight, preferably at least 35% by weight and especially preferably at least 50% by weight of the total amount of the added millbase at a temperature above the gelatinization temperature of the starch present in the millbase. Moreover, controlling the viscosity can furthermore be influenced by adding the at least one starch-liquefying enzyme, preferably an α-amylase, and/or the at least one saccharifying enzyme, preferably a glucoamylase, portionwise themselves.

By practicing steps a1) and a2), it is possible to produce the sugar-containing liquid with a monosaccharide content of preferably more than 30% by weight, especially preferably more than 35% by weight and very especially preferably more than 40% by weight.

Enzymes which can be used for liquefying the starch portion in the millbase are, in principle, all the α-amylases (enzyme class EC 3.2.1.1), in particular α-amylases obtained from *Bacillus lichenformis* or *Bacillus staerothermophilus* and specifically those which are used for liquefying materials obtained by dry-milling methods in connection with the production of bioethanol. The α-amylases which are suitable for the liquefaction are also commercially available, for example from Novozymes under the name Termamyl 120 L, type L; or from Genencor under the name Spezyme. A combination of different α-amylases may also be employed for the liquefaction.

Enzymes which can be used for saccharifying dextrins (i.e. oligosaccharides) in the liquefied starch solution are, in principle, all the glucoamylases (enzyme class EC 3.2.1.3), in particular glucoamylases obtained from *Aspergilus* and specifically those which are used for saccharifying materials obtained by dry-milling methods in connection with the production of bioethanol. The glucoamylases which are suitable for the saccharification are also commercially available, for example from Novozymes under the name Dextrozyme GA; or from Genencor under the name Optidex. A combination of different glucoamylases may also be used.

To stabilize the enzymes employed, the concentration of $Ca^{2+}$ ions may, if appropriate, be adjusted to an enzyme-specific optimum value, for example using $CaCl_2$. Suitable concentration values can be determined by the skilled worker in routine experiments. If, for example, Termamyl is employed as α-amylase, it is advantageous to adjust the $Ca^{2+}$ concentration to for example 50 to 100 ppm, preferably 60 to 80 ppm and especially preferably about 70 ppm in the liquid medium.

Since the entire starch feedstock is used for the production of the sugar-containing liquid medium of a), for example in the case of cereals the entire kernel, the non-starchy solid constituents of the starch feedstock are also present. This frequently brings about the introduction of an amount of phytate from the cereal, which amount is not to be overlooked. To avoid the inhibitory effect which thus results, it is advantageous to add, in step a2), at least one phytase to the liquid medium before subjecting the sugar-containing liquid medium to the fermentation step b).

The phytase can be added before, during or after the liquefaction or the saccharification, if it is sufficiently stable to the respective high temperatures.

Any phytases can be employed as long as their activity is in each case not more than marginally affected under the reaction conditions. Phytases used preferably have a heat stability (T50)>50° C. and especially preferably >60° C.

The amount of phytase is usually from 1 to 10 000 units/kg starch feedstock and in particular 10 to 2000 units/kg starch feedstock.

To increase the overall sugar yield, or to obtain free amino acids, further enzymes, for example pullulanases, cellulases, hemicellulases, glucanases, xylanases, glucosidases or proteases, may additionally be added to the reaction mixture during the production of the sugar-containing liquid medium. The addition of these enzymes can have a positive effect on the viscosity, i.e. reduced viscosity (for example by cleaving longer-chain glucans and/or (arabino-)xylanes), and bring about the liberation of metabolizable glucosides and the liberation of (residual) starch. The use of proteases has analogous positive effects, it additionally being possible to liberate amino acids which act as growth factors for the fermentation.

The sugar-containing liquid medium can advantageously be used for the fermentative production of a microbial metabolite having at least 3 carbon atoms or at least 2 carbon atoms and at least 1 nitrogen atom. To this end, the sugar-containing liquid medium produced in step a) is subjected to a fermentation as described in b). In the fermentation, fine chemicals, i.e. compounds having at least 3 carbon atoms and/or at least one nitrogen atom and at least 2 carbon atoms, are produced by the microorganisms. As a rule, the fermentation process can be carried out in the usual manner which is known to the skilled worker. The ratio of volumes between the sugar-containing liquid medium fed and the liquid medium which has initially been introduced and contains the microorganisms is, in general, in the range of from approximately 1:10 to 10:1, for example approximately 1:2 or approximately 2:1 and in particular approximately 1:1. The sugar content in the fermentation liquor can be regulated in particular via the feed rate of the sugar-containing liquid medium. As a rule, the feed rate will be adjusted in such a way that the monosaccharide content in the fermentation liquor is in the range of from ≥0% by weight to approximately 5% by weight; however, the fermentation can also be carried out at markedly higher monosaccharide contents in the fermentation liquor, for example approximately 10 to 20% by weight.

If the saccharification and the fermentation are carried out separately, the sugar-containing liquid medium produced in step a) can, if appropriate, be sterilized before carrying out the fermentation, during which process the microorganisms are destroyed by thermal, chemical or mechanical methods. For doing so, the liquor is usually heated at temperatures of above 80° C. The destruction, or lysis, of the cells can be effected immediately before the fermentation. To this end, all of the sugar-containing liquid medium is lysed or destroyed. This can be carried out by thermal, mechanical or chemical means. However, for the purpose of the method according to the invention, carrying out a sterilization step before the fermentation, as described herein, has proved to be not necessary; rather, it has proved to be advantageous not to carry out such a sterilization step. Accordingly, a preferred embodiment of the invention relates to a process in which the liquid medium produced in step a) is fermented directly, i.e. without prior sterilization, or a saccharification is carried out which is at least partially performed in situ.

The fermentation results in a liquid medium which, in addition to the desired nonvolatile microbial metabolic product comprises essentially the biomass produced during the fermentation, the nonmetabolized constituents of the saccharified starch solution and, in particular, the nonstarchy solid constituents of the starch source such as, for example, fibers and nonutilized sugars, as well as nonutilized buffer salts and nutrient salts. This liquid medium is also referred to in the present application as fermentation liquor, the term fermentation liquor also comprising the (sugar-containing) liquid medium in which an initially partial or incomplete fermentative conversion of the sugars present, i.e. a partial or incomplete microbial metabolization of the monosaccharides, has taken place.

Hereinbelow, the term fine chemical comprises in particular organic mono-, di- and tricarboxylic acids which preferably have 3 to 10 carbon atoms and which, if appropriate, have one or more, for example 1, 2, 3 or 4, hydroxyl groups attached to them, for example tartaric acid, itaconic acid, succinic acid, fumaric acid, maleic acid, 2,5-furandicarboxylic acid, 3-hydroxypropionic acid, glutaric acid, levulic acid, lactic acid, propionic acid, gluconic acid, aconitic acid and diaminopimelic acid, citric acid; proteinogenic and nonproteinogenic amino acids, for example lysine, glutamate, methionin, phenylalanin, aspartic acid and threonin; purine and pyrimidine bases; nucleosides and nucleotides, for example nicotinamide adenine dinucleotide (NAD) and adenosine-5'-monophosphate (AMP); lipids; saturated and unsaturated fatty acids having preferably 10 to 22 carbon atoms, for example γ-linolenic acid, dihomo-γ-linolenic acid, arachidonic acid, eicosapentaenoic acid and docosahexaenoic acid; diols having preferably 3 to 8 carbon atoms, for example propanediol and butanediol; higher-functionality alcohols having 3 or more, for example 3, 4, 5 or 6, OH groups, for example glycerol, sorbitol, mannitol, xylitol and arabinitol; longer-chain alcohols having at least 4 carbon atoms, for example 4 to 22 carbon atoms, for example butanol; carbohydrates, for example hyaluronic acid and trehalose; aromatic compounds, for example aromatic amines, vanillin and indigo; vitamins and provitamins, for example ascorbic acid, vitamin $B_6$, vitamin $B_{12}$ and riboflavin, cofactors and what are known as nutraceutics; proteins, such as enzymes, for example phytases, xylanases and gluconases; carotenoids, for example lycopene, β-carotin, astaxanthin, zeaxanthin and canthaxanthin; ketones having preferably 3 to 10 carbon atoms and, if appropriate, 1 or more hydroxyl groups, for example acetone and acetoin; lactones, for example γ-butyrolactone, cyclodextrins, biopolymers, for example polyhydroxyacetate, polyesters, polysaccharides, polyisoprenoids, polyamides, polyhydroxyalkanoates, for example poly-3-hydroxybutyric acid and copolyesters with other organic hydroxycarboxylic acids such as 3-hydroxyvaleric acid, 4-hydroxybutyric acid and others which are described in Steinbüchel (Ed.), Biopolymers, 1st Ed., 2003, Wiley-VCH, Weinheim, and the literature cited therein; and precursors and derivatives of the abovementioned compounds. Other compounds which are suitable as fine chemicals are described by Gutcho in Chemicals by Fermentation, Noyes Data Corporation (1973), ISBN: 0818805086.

The term "cofactor" comprises nonproteinaceous compounds which are required for the occurrence of a normal enzyme activity. These compounds can be organic or inorganic; preferably, the cofactor molecules of the invention are organic. Examples of such molecules are NAD and nicotinamide adenine dinucleotide phosphate (NADP); the precursor of these cofactors is niacin.

The term "nutraceutical" comprises food additives which promote health in plants and animals, in particular humans. Examples of such molecules are vitamins, antioxidants and certain lipids, for example polyunsaturated fatty acids.

In particular, the metabolic products produced are selected from amongst enzymes, amino acids, vitamins, disaccharides, aliphatic mono- and dicarboxylic acids having 3 to 10 C atoms, aliphatic hydroxycarboxylic acids having 3 to 10 C atoms, ketones having 3 to 10 C atoms, alkanols having 4 to 10 C atoms, alkanediols having 3 to 8 C atoms and polyhydroxyalkanoates.

It is clear to the skilled worker that the compounds produced via the fermentative route in accordance with the invention are in each case obtained in the enantiomeric form produced by the microorganisms used (if different enantiomers exist). In the case of the amino acids, for example, it is the respective L enantiomer which is obtained as a rule.

The process according to the invention is preferably employed for the production of nonvolatile microbial metabolites. For the purposes of the present invention, nonvolatile metabolites are understood as meaning compounds which in general cannot be removed by distillation from the fermentation liquor without undergoing decomposition. As a rule, these compounds have a boiling point which is above the boiling point of water, frequently above 150° C., and in particular above 200° C., at atmospheric pressure. As a rule, these are compounds which are in the solid state under standard conditions (298 K, 101.3 kPa).

However, it is also possible to employ the process according to the invention for the production of nonvolatile microbial metabolic products which, under standard conditions, have a melting point below the boiling point of water and/or an oily consistency. In this case, as a rule, the maximum temperature will be controlled during work-up, in particular during drying. These compounds can advantageously also be produced in such a way that they are formulated in virtually solid form (pseudo-solid form) on adsorbents. In such a case, the solid constituents of the fermentation liquor will usually be removed before the depletion or isolation of the product of interest in accordance with step c).

Absorbents which are suitable for the above purpose are, for example, active charcoals, aluminas, silica gels, silicic acid, clay, soots, zeolites, inorganic alkali metal and alkaline earth metal salts such as the hydroxides, carbonates, silicates, sulfates and phosphates of sodium, potassium, magnesium and calcium, in particular magnesium and calcium salts, for example $Mg(OH)_2$, $MgCO_3$, $MgSiO_4$, $CaSO_4$, $CaCO_3$, alkaline earth metal oxides, for example MgO and CaO, other inorganic phosphates and sulfates, for example $ZnSO_4$, salts of organic acids, in particular their alkali metal and alkaline earth metal salts, specifically their sodium and potassium salts, for example sodium acetate, sodium formate, sodium hydrogen formate, sodium citrate, potassium acetate, potassium formate, potassium hydrogen formate and potassium citrate, and high-molecular-weight organic carriers such as carbohydrates, for example sugars, optionally modified starches, cellulose, lignin, and generally the carrier materials mentioned hereinbelow in connection with the formulation of the product. As a rule, the abovementioned carrier materials will contain halogens such as chloride ions and nitrates in very small amounts, in particular only traces, or none at all.

Examples of compounds which, under standard conditions, have a melting point below the boiling point of water and/or an oily consistency and which can advantageously be produced in this manner by the process according to the invention are γ-linolenic acid, dihomo-γ-linolenic acid, arachidonic acid, eicosapentaenoic acid and docosahexaenoic acid, furthermore propionic acid, lactic acid, propanediol, butanol and acetone. Within the meaning of the present invention, these compounds in pseudo-solid formulation are likewise considered as being nonvolatile microbial metabolites in solid form.

The microorganisms employed in the fermentation depend in a manner known per se on the fine chemicals in question, as specified in detail hereinbelow. They can be of natural origin or genetically modified. Examples of suitable microorganisms and fermentation processes are those given in Table A hereinbelow:

TABLE A

| Substance | Microorganism | Reference |
|---|---|---|
| Tartaric acid | Lactobacilli, (for example Lactobacillus delbrueckii) | Rehm, H.-J.: Biotechnology, Weinheim, VCH, 1980 and 1993-1995; Gutcho, Chemicals by Fermentation, Noyes Data Corporation (1973), |
| Itaconic acid | Aspergillus terreus, Aspergillus itaconicus | Jakubowska, in Smith and Pateman (Eds.), Genetics and Physiology of Aspergillus, London: Academic Press 1977; Miall, in Rose (Ed.), Economic Microbiology, Vol. 2, pp. 47-119, London: Academic Press 1978; U.S. Pat. No. 3,044,941 (1962). |
| Succinic acid | Actinobacillus sp. 130Z, Anaerobiospirillum succiniproducens, Actinobacillus succinogenes, E. coli | Int. J. Syst. Bacteriol. 26, 498-504 (1976); EP 249773 (1987), Inventors: Lemme and Datta; U.S. Pat. No. 5,504,004 (1996), Inventors: Guettler, Jain and Soni; Arch. Microbiol. 167, 332-342 (1997); Guettler MV, Rumler D, Jain MK., Actinobacillus succinogenes sp. nov., a novel succinic-acid-producing strain from the bovine rumen. Int J Syst Bacteriol. 1999 Jan; 49 Pt 1: 207-16; U.S. Pat. No. 5,723,322, U.S. Pat. No. 5,573,931, U.S. Pat. No. 5,521,075, WO99/06532, U.S. Pat. No. 5,869,301, U.S. Pat. No. 5,770,435 |
| Hydroxypropionic acid | Lactobacillus delbrückii, L. leichmannii or Sporolactobacillus inulinus | RÖMPP Online Version 2.2 |
| Propionic acid | Propionibacterium, for example P. arabinosum, P. schermanii, P. freudenreichii, Clostridium propionicum, | Rehm, H.-J.: Biotechnology, Weinheim, VCH, 1980 and 1993-1995; Gutcho, Chemicals by Fermentation, Noyes Data Corporation (1973), |
| Diaminopimelic acid | Corynebacterium glutamicum | Rehm, H.-J.: Biotechnology, Weinheim, VCH, 1980 and 1993-1995; Gutcho, Chemicals by Fermentation, Noyes Data Corporation (1973), |
| Citric acid | Aspergillus niger, Aspergillus wentii | Crit. Rev. Biotechnol. 3, 331-373 (1986); Food Biotechnol. 7, 221-234 (1993); 10, 13-27 (1996). |
| Aconitic acid | Aspergillus niger, Aspergillus wentii | Crit. Rev. Biotechnol. 3, 331-373 (1986); Food Biotechnol. 7, 221-234 (1993); 10, 13-27 (1996).; Rehm, H.-J.: Biotechnology, Weinheim, VCH, 1980 and 1993-1995; |
| Malic acid | Aspergilli, for example Aspergillus flavus, | U.S. Pat. No. 3,063,910 |

TABLE A-continued

| Substance | Microorganism | Reference |
|---|---|---|
| Gluconic acid | A. niger, A. oryzae, Corynebacterium Aspergilli, for example A. niger | Gutcho, Chemicals by Fermentation, Noyes Data Corporation (1973), |
| Butyric acid | Clostridium (for example Clostridium acetobutlicum, C. butyricum) | Rehm, H.-J.: Biotechnology, Weinheim, VCH, 1980 and 1993-1995; |
| Lactic acid | Lactobacillus for example L. delbruckii, L. leichmannii, | Rehm, H.-J.: Biotechnology, Weinheim, VCH, 1980 and 1993-1995; |
| Lysine | Corynebacterium glutamicum | Ikeda, M.: Amino Acid Production Process (2003), Adv. Biochem. Engin/Biotechnol 79, 1-35. |
| Glutamate | Corynebacterium glutamicum | Ikeda, M.: Amino Acid Production Process (2003), Adv. Biochem. Engin/Biotechnol 79, 1-35. |
| Methionin | Corynebacterium glutamicum | Ikeda, M.: Amino Acid Production Process (2003), Adv. Biochem. Engin/Biotechnol 79, 1-35. |
| Phenylalanin | Corynebacterium glutamicum, E. coli | Trends Biotechnol. 3, 64-68 (1985); J. Ferment. Bioeng. 70, 253-260 (1990). |
| Threonin | E. coli | Ikeda, M.: Amino Acid Production Process (2003), Adv. Biochem. Engin/Biotechnol 79, 1-35. |
| Aspartic acid | E. coli | Ikeda, M.: Amino Acid Production Process (2003), Adv. Biochem. Engin/Biotechnol 79, 1-35 and references cited therein, Gutcho, Chemicals by Fermentation, Noyes Data Corporation (1973) |
| Purine and pyrimidine bases | Bacillus subtilis | Rehm, H.-J.: Biotechnology, Weinheim, VCH, 1980 and 1993-1995; Gutcho, Chemicals by Fermentation, Noyes Data Corporation (1973), |
| Nicotinamide adenine dinucleotide (NAD) | Bacillus subtilis | Rehm, H.-J.: Biotechnology, Weinheim, VCH, 1980 and 1993-1995; Gutcho, Chemicals by Fermentation, Noyes Data Corporation (1973), |
| Adenosine-5'-monophosphate (AMP) | Bacillus subtilis | Rehm, H.-J.: Biotechnology, Weinheim, VCH, 1980 and 1993-1995; Gutcho, Chemicals by Fermentation, Noyes Data Corporation (1973), |
| γ-Linolenic acid | Mucor, Mortiella, Aspergillus spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Dihomo-γ-linolenic acid | Mortiella, Conidiobolus, Saprolegnia spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Arachidonic acid | Mortiella, Phytium spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Eicosapentaenoic acid | Mortiella, Phytium spp., Rhodopseudomonas, Shewanella spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Docosahexaenoic acid | Thraustochytrium, Entomophthora spp., Rhodopseudomonas, Shewanella spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by Pythium irregulare for Lipid Production. Master Thesis Lousiana State University, 31.10.2002 (URN etd-1111102-205855). |
| Propanediol | E. coli | DE 3924423, US 440379, WO 9635799, U.S. Pat. No. 5,164,309 |
| Butanediol | Enterobacter aerogenes, Bacillus subtilis, Klebsiella oxytoca | Rehm, H.-J.: Biotechnology, Weinheim, VCH, 1980 and 1993-1995; Gutcho, Chemicals by Fermentation, Noyes Data Corporation (1973), H. G. SCHLEGEL and H. W. JANNASCH, 1981; Afschar et al.: Mikrobielle Produktion von 2,3-Butanediol, CIT 64 (6), 2004, 570-571 |

TABLE A-continued

| Substance | Microorganism | Reference |
|---|---|---|
| Butanol | Clostridium (for example Clostridium acetobutlicum, C. propionicum) | Rehm, H.-J.: Biotechnology, Weinheim, VCH, 1980 and 1993-1995; Gutcho, Chemicals by Fermentation, Noyes Data Corporation (1973), |
| Glycerol | Yeast, Saccharomyces rouxii | Gutcho, Chemicals by Fermentation, Noyes Data Corporation (1973), |
| Mannitol | Aspergillus candidu, Torulopsis mannitofaciens | Gutcho, Chemicals by Fermentation, Noyes Data Corporation (1973), |
| Arabitol | Saccharomyces rouxii, S. mellis, Sclerotium glucanicum, Pichia ohmeri | Gutcho, Chemicals by Fermentation, Noyes Data Corporation (1973), |
| Xylitol | Saccharomyces cerevisiae | Gutcho, Chemicals by Fermentation, Noyes Data Corporation (1973), |
| Hyaluronic acid | Streptococcus spp. | Rehm, H.-J.: Biotechnology, Weinheim, VCH, 1980 and 1993-1995; |
| Trehalose | Brevibacterium, Corynebacterium, Microbacterium, Arthrobacter spp., Pleurotus genus, Filobasidium floriforme | JP 05099974, JP 06311891, FR 2671099, EP 0555540, JP 3053791, Miyazaki, J.-I., Miyagawa, K.-I., Sugiyama, Y.: Trehalose Accumulation by Basidiomycotinous Yeast, Filobasidium floriforme. Journal of Fermentation and Bioengineering 81, (1996) 4, 315-319. |
| Ascorbic acid | Gluconobacter melanogenes | RÖMPP Online Version 2.2 |
| Vitamin $B_{12}$ | Propionibacterium spp., Pseudomonas denitrificans | Chem. Ber. 1994, 923-927; RÖMPP Online Version 2.2 |
| Riboflavin | Bacillus subtilis, Ashbya Gossypii | WO 01/011052, DE 19840709, WO 98/29539, EP 1186664; Fujioka, K.: New biotechnology for riboflavin (vitamin $B_2$) and character of this riboflavin. Fragrance Journal (2003), 31(3), 44-48. |
| Vitamin $B_6$ | Rhizobium tropici, R. meliloti | EP0765939 |
| Enzymes | Aspergilli (for example Aspergillus niger A. oryzae), Trichoderma, E. coli, Hanseluna or Pichia (for example Pichia pastorius), Bacillus (for example Bacillus licheniformis B. subtilis) and many others | Rehm, H.-J.: Biotechnology, Weinheim, VCH, 1980 and 1993-1995; Gutcho, Chemicals by Fermentation, Noyes Data Corporation (1973), |
| Zeaxanthin | Dunaliella salina | Jin et al (2003) Biotech.Bioeng. 81: 115-124 |
| Canthaxanthin | Brevibacterium | Nelis et al (1991) J Appl Bacteriol 70: 181-191 |
| Lycopene | Blakeslea trispora, Candida utilis | WO 03/056028, EP 01/201762, WO 01/12832, WO 00/77234, Miura et al (1998) Appl Environ Microbiol 64: 1226-1229 |
| β-Carotene | Blakeslea trispora, Candida utilis | Kim S., Seo W., Park Y., Enhanced production of beta-carotene from Blakeslea trispora with Span 20, Biotechnology Letters, Vol 19, No 6, 1997, 561-562; Mantouridou F., Roukas T.: Effect of the aeration rate and agitation speed on beta-carotene production and morphology of Blakeslea trispora in a stirred tank reactor: mathematical modelling, Biochemical Engineering Journal 10 (2002), 123-135; WO 93/20183; WO 98/03480, Miura et al (1998) Appl Environ Microbiol 64: 1226-1229 |
| Astaxanthin | Phaffia Rhodozyma; Candida utilis | US 00/5599711; US 90/00558; WO 91/02060, Miura et al (1998) Appl Environ Microbiol 64: 1226-1229 |
| Polyhydroxy-alkanoates, polyesters | Escherchia coli, Alcaligenes latus, and many others | S. Y. Lee, Plastic Bacteria? Progress and Prospects for polyhydroxyalkanoate production in bacteria, Tibtech, Vo. 14, (1996), pp. 431-438., Steinbüchel, 2003; Steinbüchel (Ed.), Biopolymers, 1st ed., 2003, Wiley-VCH, Weinheim and references cited therein |
| Polysaccharides | Leuconostoc mesenteroides, L. dextranicum, Xanthomonas campestris, and many others | Rehm, H.-J.: Biotechnology, Weinheim, VCH, 1980 and 1993-1995; Gutcho, Chemicals by Fermentation, Noyes Data Corporation (1973), |
| Polyisoprenoides | Lactarius sp., Hygrophorus sp., Russula sp. | Steinbüchel (Ed.), Biopolymers, 1st ed., 2003, Wiley-VCH, Weinheim and references cited therein |

TABLE A-continued

| Substance | Microorganism | Reference |
| --- | --- | --- |
| Acetone | Clostridium (for example. Clostridium acetobutlicum, C. propionicum) | Rehm, H.-J.: Biotechnology, Weinheim, VCH, 1980 and 1993-1995; Gutcho, Chemicals by Fermentation, Noyes Data Corporation (1973), |
| Acetoin | Enterobacter aerogenes, Clostridium acetobutylicum, Lactococcus lactis | Lengeler, J. W., Drews, G., Schlegel, H. G.: Eds., Biology of the Procaryotes, Thieme, Stuttgart (1999), p. 307; RÖMPP Online-Edition |
| Vanillin | Pseudomonas putida, Amycolatopsis sp. | Priefert, H., Rabenhorst, J., Seinbüchel, A. Biotechnological production of vanillin. Appl. Microbiol. Biotechnol. 56, 296-314 (2001) |
| Thurigensin | Bacillus thuringiensis | Jian-Zhong Jong et al.: Fed-batch culture of Bacillus thuringiensis for thuringensin production in a tower type bioreactor. Biotechnology and Bioengineering 48 (3) (2004), 207-213. |
| Polyketides | Streptomyces fradiae, Sorangium cellulosum | Kirst: Fermentation-derived compounds as a source for new products. Pure & Appl. Chem. 70 (2), (1998), 335-338; Zirkle et al.: Heterologous production of the antifungal polyketide antibiotic soraphen A of Sorangium cellulosum So ce26 in Streptomyces lividans. Microbiology 150 (8), (2004), 2761-74. |
| Gibberellic acid | Gibberella fujikuroi | Hollmann et al.: Extraktiv-Fermentation von Gibberellinsäure mit Gibberella fujikuroi. CIT 7 (1995), 892-895. |
| Indigo | Escherichia coli JB 102 | Berry, A., Dodge, T. C., Pepsin, M., Weyler, W.: Application of metabolic engineering to improve both the production and use of biotech indigo. Journal of Industrial Microbiology & Biotechnology 28 (2002), 127-133. |

Preferred embodiments of the process according to the invention relate to the production of enzymes such as phytases, xylanases, glucanases; amino acids such as lysine, methionine, threonine; vitamins such as pantothenic acid and riboflavin; their precursors and derivatives; and the production of the abovementioned mono-, di- and tricarboxylic acids, in particular aliphatic mono- and dicarboxylic acids having 3 to 10 C atoms such as propionic acid and succinic acid, aliphatic hydroxycarboxylic acids having 3 to 10 C atoms such as lactic acid; of the abovementioned longer-chain alkanols, in particular alkanols having 4 to 10 C atoms such as butanol; of the abovementioned diols; in particular alkanediols having 3 to 8 C atoms such as propanediol; of the abovementioned ketones, in particular ketones having 3 to 10 C atoms such as acetone; of the abovementioned carbohydrates, in particular disaccharides such as trehalose; and of polyhydroxyalkanoates.

In a preferred embodiment, the microorganisms employed in the fermentation are therefore selected from among natural or recombinant microorganisms which produce at least one of the following metabolites: enzymes such as phytases, xylanases, glucanases; amino acids such as lysine, threonine, methionine; vitamins such as pantothenic acid and riboflavin; their precursors and/or derivatives; disaccharides such as trehalose; in particular aliphatic mono- and dicarboxylic acids having 3 to 10 C atoms such as propionic acid and succinic acid, aliphatic hydroxycarboxylic acids having 3 to 10 C atoms such as lactic acid; ketones having 3 to 10 C atoms such as acetone; alkanols having 4 to 10 C atoms such as butanol; alkanediols having 3 to 8 C atoms such as propanediol; and polyhydroxyalkanoates.

In particular, the microorganisms are selected from among the genera Corynebacterium, Bacillus, Ashbya, Escherichia, Aspergillus, Alcaligenes, Actinobacillus, Anaerobiospirillum, Lactobacillus, Propionibacterium and Clostridium, in particular, among strains of Corynebacterium glutamicum, Bacillus subtilis, Ashbya gossypii, Escherichia coli, Aspergillus niger or Alcaligenes latus, Anaerobiospirillum succiniproducens, Actinobacillus succinogenes, Lactobacillus delbrückii, Lactobacillus leichmanni, Propionibacterium arabinosum, Propionibacterium schermanii, Propionibacterium freudenreichii, Clostridium propionicum and Clostridium acetobutlicum.

In a specific preferred embodiment, the metabolite produced by the microorganisms in the fermentation is lysine. To carry out the fermentation, analogous conditions and procedures as have been for other carbon feedstocks, for example in Pfefferle et al., loc. cit. and U.S. Pat. No. 3,708,395, can be employed. In principle, both a continuous and a discontinuous (batch or fed-batch) mode of operation are suitable, with the fed-batch mode being preferred.

In a further especially preferred embodiment, the metabolite produced by the microorganisms in the fermentation is methionin. To carry out the fermentation, analogous conditions and procedures as have been described for other carbon feedstocks, for example in WO 03/087386 and WO 03/100072, may be employed.

In a further especially preferred embodiment, the metabolite produced by the microorganisms in the fermentation is pantothenic acid. To carry out the fermentation, analogous conditions and procedures as have been described for other carbon feedstocks, for example in WO 01/021772, may be employed.

In a further especially preferred embodiment, the metabolite produced by the microorganisms in the fermentation takes the form of polyhydroxyalkanoates such as poly-3-hydroxybutyrate and copolyesters with other organic hydroxycarboxylic acids such as 3-hydroxyvaleric acid, 4-hydroxybutyric acid and others which are described in Steinbüchel (loc. cit.), including for example longer-chain hydroxycarboxylic acids such as 3-hydroxyoctanoic acid, 3-hydroxydecanoic acid and 3-hydroxytetradecanoic acid, and mixtures of these. To carry out the fermentation, analogous conditions and procedures as have been described for other carbon feedstocks, for example in S. Y. Lee, Plastic Bacteria Progress and prospects for polyhydroxyalkanoate production in bacteria, Tibtech, Vol. 14, (1996), pp. 431-438, may be employed.

In a further especially preferred embodiment, the metabolite produced by the microorganisms in the fermentation is riboflavin. To carry out the fermentation, analogous conditions and procedures as have been described for other carbon feedstocks, for example in WO 01/011052, DE 19840709, WO 98/29539, EP 1186664 and Fujioka, K: New biotechnology for riboflavin (vitamin B2) and character of this riboflavin. Fragrance Journal (2003), 31(3), 44-48, may be employed.

In a further especially preferred embodiment, the metabolite produced by the microorganisms in the fermentation is a phytase. To carry out the fermentation, analogous conditions and procedures as have been described for other carbon sources, for example in WO 98/55599, can also be applied here.

If appropriate, a sterilization step is carried out in the above-described manner before the fermentation liquor is processed further (i.e. before step c).

The isolation or depletion of the metabolite from the fermentation liquor in accordance with step c) is, as a rule, carried out in such a way that at least one metabolite is depleted or isolated from the fermentation liquor in such a way that the content of this metabolite in the remaining fermentation liquor amounts to not more than 20% by weight, in particular not more than 10% by weight, specifically not more than 5% by weight and very specifically not more than 2.5% by weight, in each case based on the total weight of the remaining fermentation liquor.

The isolation or depletion of fine chemicals (i.e. of the microbial metabolite) from the fermentation liquor in accordance with step c) can be performed as one or more steps. An essential step in this context is the removal of the solid constituents from the fermentation liquor. This can be carried out either before or after isolation of the product of value. Methods conventionally used in the art which also comprise steps for the rough cleaning and the fine purification of the products of value and for formulation are known both for the isolation of products of value and for the removal of solids, i.e. solid-liquid phase separation (for example described in Belter, P. A, Bioseparations: Downstream Processing for Biotechnology, John Wiley & Sons (1988), and Ullmann's Encyclopedia of Industrial Chemistry, 5th ed. on CD-ROM, Wiley-VCH).

To isolate the product of value, a procedure can advantageously be followed in which the solid constituents are first removed from the fermentation liquor, for example by means of centrifugation or filtration, and the product of value is subsequently isolated from the liquid phase, for example by crystallization, precipitation, adsorption or distillation. As an alternative, the product of value can also be isolated directly from the fermentation liquor, for example by using chromatographic methods or extractive methods. A chromatographic method which must be mentioned in particular is ion-exchange chromatography, where the product of value can be isolated selectively on the chromatography column. In this case, the removal of the solids from the fermentation liquor which remains is advantageously carried out for example by decanting, evaporation and/or drying.

Examples of conventional filtration methods are cake filtration and depth filtration (for example described in A. Rushton, A. S. Ward, R. G. Holdich: Solid-Liquid Filtration and Separation Technology, VCH Verlagsgesellschaft, Weinheim 1996, pp. 177 ff., K. J. Ives, in A. Rushton (Ed.): Mathematical Models and Design Methods in Solid-Liquid Separation, NATO ASI series E No. 88, Martinus Nijhoff, Dordrecht 1985, pp. 90 ff.) and cross-flow filtrations, in particular microfiltration for the removal of solids >0.1 µm (for example described in J. Altmann, S. Ripperger, J. Membrane Sci. 124 (1997) 119-128).

Customary centrifugation methods are described for example in G. Hultsch, H. Wilkesmann, "Filtering Centrifuges," in D. B. Purchas, Solid-Liquid Separation, Upland Press, Croydon 1977, pp. 493-559; and H. Trawinski, Die äquivalente Klärfläche von Zentrifugen [The equivalent clarifying area of centrifuges], Chem. Ztg. 83 (1959) 606-612. Various designs such as tube centrifuges, basket centrifuges and, specifically, pusher centrifuges, slip-filter centrifuges and disk separators may be employed.

Conventional extraction methods comprise batchwise or stepwise methods and differential continuous methods with cocurrent flow or countercurrent flow. In this context, the method may involve two or one mobile phase(s). The solubility in both phases, of the product of value and of the secondary components to be removed, can be influenced, inter alia, by the choice of the solvent, the variation of the counterions and by varying the pH (Treybal, R. E., Mass Transfer Operations, 3rd ed., New York, McGraw-Hill, 1979; Kula, M., Kroner, K. H., Hustedt, H. and Schutee, H., Technical aspects of extractive enzyme purification, Ann. N.Y. Acad. Sci., 341 (1981); Robinson, R. G., and Cha, D. Y., Controlled pH extraction in the separation of weak acids and bases, Biotech. Progress, 1(1), 18 (1985)).

Customary adsorption methods are described, for example in D. M. Ruthven: Principles of Adsorption and Adsorption Processes, J. Wiley & Sons, New York 1984; G. Wedler: Adsorption, Verlag Chemie, Weinheim 1970. Solid-bed, moving-bed and fluidized-bed adsorbers can be employed. The adsorption can be carried out batchwise or continuously (K. Hauffe, S. R. Morrison: De Gruyter Studienbuch "Adsorption," De Gruyter, Berlin 1974.; W. Kast: Adsorptionstechnik [Adsorption techniques], VCH Verlagsgesellschaft, Weinheim 1988). In addition to many other adsorbents, activated carbons, ion-exchanger resins, natural or synthetic zeolites and activated aluminas can be employed. Besides, affinity adsorption methods may also be employed (for example described in Arnold, F. H., Blanch, H. W. and Wilke, C. R., Analysis of Affinity separations. Chem. Engr. J., 30, B9 (1985)).

Methods which can be employed in particular for purifying the fine chemicals are, for example, chromatography, precipitation, ultrafiltration, microfiltration, nanofiltration, reverse osmosis, electrophoresis, electrodialysis and isoelectric focusing.

Chromatographic methods can be carried out batchwise or continuously. The continuous chromatography includes, for example, a continuous rotating annular chromatograph (CRAC) (for example described in A. J. P. Martin, Discuss. Farraday Soc. 7 (1949)), a true moving-bed chromatograph (TMBC) (for example described in K. Takeuchi, T. Miyauchi, Y. Uraguchi, J. Chem. Eng. Japan 11 (1978) 216-220.) and a simulated moving-bed chromatograph (SMB) (for example described in D. B. Broughton, Universal Oil Products Co., U.S. Pat. No. 2,985,589, 1961). Solid phases which are employed are, for example, activated aluminas, silica gels, glycol-impregnated diatomaceous earths, dextrans, polymers of sulfonated styrenes, polyacrylamides and polymer-bound proteins (Arnold, F. H., Blanch, H. W. and Wilke, C. R., Analysis of Affinity separations. Chem. Engr. J., 30, B9 (1985); Gibbs, S. J., and Lightfoot, E. N., Scaling up gradient elution chromatography, IEC Fund., 25, 490 (1986); King, C. J., Separation Processes, 2nd ed., New York, McGraw-Hill (1979); Yau, W. W., Kirlland, J. J. and Bly, D. D., Modern Size-Exclusion Liquid Chromatography, Wiley, New York (1979)).

A precipitation may involve a precipitation of either the products of value or the secondary components (J. W. Mullin: Crystallization, 3rd ed., Butterworth-Heinemann, Oxford 1993). The precipitation can be initiated for example by addition of a further solvent, addition of salts and the variation of the temperature. The resulting precipitate can be separated from the liquor by the above-described conventional methods for separating solids.

Examples of materials which can be employed in microfiltration, ultrafiltration, nanofiltration and reverse osmosis are microporous membranes (A. S. Michaels: "Ultrafiltration," in E. S. Perry (ed.): Progress in Separation and Purification, vol. 1, Interscience Publ., New York 1968.), homogeneous membranes (J. Crank, G. S. Park (eds.): Diffusion in Polymers, Academic Press, New York 1968; S. A. Stern: "The Separation of Gases by Selective Permeation," in P. Meares (ed.): Membrane Separation Processes, Elsevier, Amsterdam 1976), asymmetric membranes (R. E. Kesting: Synthetic Polymeric Membranes, A Structural Perspective, Wiley-Interscience, New York 1985) and electrically charged membranes (F. Helfferich: Ion-Exchange, McGraw-Hill, London 1962), all of which are produced by different methods (R. Zsigmondy, U.S. Pat. No. 1,421,341, 1922; D. B. Pall, U.S. Pat. No. 4,340,479, 1982; S. Loeb, S. Sourirajan, U.S. Pat. No. 3,133,132, 1964). Typical materials are cellulose esters, nylon, polyvinyl chloride, acrylonitrile, polypropylene, polycarbonate and ceramics. These membranes are employed as a plate module (R. F. Madsen, Hyperfiltration and Ultrafiltration in Plate-and-Frame Systems, Elsevier, Amsterdam 1977), spiral module (U.S. Pat. No. 3,417,870, 1968 (D. T. Bray)), tube bundle or hollow-fiber module (H. Strathmann: "Synthetic Membranes and their Preparation," in M. C. Porter (ed.): Handbook of Industrial Membrane Technology, Noyes Publication, Park Ridge, N.J. 1990, pp. 1-60). In addition, the use of liquid membranes is possible (N. N. Li: "Permeation Through Liquid Surfactant Membranes," AlChE J. 17 (1971) 459; S. G. Kimura, S. L. Matson, W. J. Ward III: "Industrial Applications of Facilitated Transport," in N. N. Li (ed.): Recent Developments in Separation Science, vol. V, CRC Press, Boca Raton, Fla., 1979, pp. 11-25). The desired product of value can not only be enriched on the feed side and removed via the retentate stream, but also depleted on the feed side and removed via the filtrate/permeate stream.

Electrophoretic methods are described, for example in Rudge, S. R., Ladisch, M. R., Process considerations for scale-up of liquid chromatography and electrophoresis, in Separation Recovery and Purification in Biotechnology, J. Asenjo and J. Hong, eds., ACS Symposium Series, 314, 122 (1986). A large number of variants such as, for example, isoelectric focusing in granulated gel layers, continuous isoelectric focusing with recycling, the "Rotofor" cell, free-flow focusing with recycling and multi-compartmental electrolysis with isoelectric membranes are used. Matrix materials which are employed are, inter alia, cellulose acetate, agarose gels and polyacrylamide gels.

Customary crystallization methods are described, for example, in Janeic, S. J., Grootscholten, P. A., Industrial Crystallization, New York, Academic, 1984; A. W. Bamforth: Industrial Crystallization, Leonard Hill, London 1965; G. Matz: Kristallisation, 2nd ed., Springer Verlag, Berlin 1969; J. Nývlt: Industrial Crystallization—State of the Art. VCH Verlagsges., Weinheim 1982; S. J. Jancić, P. A. M. Grootscholten: Industrial Crystallization, Reidel, Dordecht 1984; O. Söhnel, J. Garside: Precipitation, Butterworth-Heinemann, Oxford, 1992; A. S. Myerson (ed.): Handbook of Industrial Crystallization, Butterworth-Heineman, Boston 1993; J. W. Mullin: Crystallization, 3rd ed., Butterworth-Heinemann, Oxford 1993; A. Mersmann (ed.): Crystallization Technology Handbook, Marcel Dekker, New York 1995. Crystallization can be achieved for example by cooling, evaporation, vacuum crystallization (adiabatic cooling), reaction crystallization and salting out. The crystallization can be carried for example in stirred and unstirred tanks, in the direct-contact process, in evaporative crystallizers (R. K. Multer, Chem. Eng. (N.Y.) 89 (1982) March, 87-89), in vacuum crystallizers batchwise or continuously, for example in forced-circulation crystallizers (Swenson forced-circulation crystallizer) or fluidized-bed crystallizers (Oslo type) (A. D. Randolph, M. A. Larson: Theory of Particulate Processes, 2nd ed. Academic Press, New York 1988; J. Robinson, J. E. Roberts, Can. J. Chem. Eng. 35 (1957) 105-112; J. Nývlt: Design of Crystallizers, CRC Press, Boca Raton, 1992). Fractional crystallization is also possible (L. Gordon, M. L. Salutsky, H. H. Willard: Precipitation from Homogeneous Solution, Wiley-Interscience, New York 1959). Likewise, enantiomers and racemates can be separated (J. Jacques, A. Collet, S. H. Willen: Enantiomers, Racemates and Resolutions, Wiley, New York 1981; R. A. Sheldon: Chirotechnology, Marcel Dekker, New York 1993; A. N. Collins, G. N. Sheldrake, J. Crosby (ed.): Chirality in Industry, Wiley, New York 1985).

Conventional drying methods are described, for example in O. Krischer, W. Kast: Die wissenschaftlichen Grundlagen der Trocknungstechnik [The scientific bases of drying technology], 3rd ed., Springer, Berlin-Heidelberg-New York 1978; R. B. Keey: Drying: Principles and Practice, Pergamon Press, Oxford 1972; K. Kröll: Trockner und Trocknungsverfahren [Dryers and drying methods], 2nd ed., Springer, Berlin-Heidelberg-New York 1978; Williams-Gardener, A.: Industrial Drying, Houston, Gulf, 1977; K. Kröll, W. Kast: Trocknen und Trockner in der Produktion [Drying and dryers in production], Springer, Berlin-Heidelberg-New York 1989. Examples of drying methods include methods for convection drying, for example in a drying oven, tunnel dryer, belt dryer, disc dryer, jet dryer, fluidized-bed dryer, aerated and rotating drum spinners, spray dryers, pneumatic-convector dryers, cyclone dryers, mixer dryers, grinder dryers, also for pastes; ring dryers, tunnel-tube dryers, rotary dryers, carousel dryers. Other methods exploit drying by contact, for example paddle dryers; vacuum, or freeze, drying, cone dryers, suction dryers, disc dryers, film dryers which operate by contact, drum dryers, viscous-phase dryers, plate dryers, rotary-coil dryers, double-cone dryers; or thermal radiation (infrared, for example infrared rotary dryers) or dielectric energy (microwaves) for drying. In most cases, the drying equipment used for thermal drying methods are heated by steam, oil, gas or electricity and can in some cases be operated under reduced pressure, depending on their design.

In addition to drying, it is also possible to employ formulation methods as they are described hereinbelow for the preparation of the protein composition. These also comprise the addition of formulation auxiliaries, as detailed hereinbelow.

In a preferred embodiment, the isolation of the fine chemicals from the fermentation liquor of c) is carried out by means of ion-exchange chromatography. Here, the general conditions and procedures are known to the skilled worker and described, for example in Römpp Lexikon der Chemie [Dictionary of Chemistry], 10th edition, 1997, Georg Thieme Verlag, Stuttgart; Weis, Handbuch der lonenchromatographie [Ion Chromatography Manual], 1991, VCH Verlagsgesellschaft, Weinheim. In general, a procedure will be followed in which the compound produced by the microorganisms is bound selectively on the ion exchanger and the ion exchanger is washed, for example with water, prior to elution of the compound produced by the microorganisms.

Before the solids-loaded fermentation liquor is applied to the ion-exchange chromatography column, the solids may, if appropriate, be removed by means of conventional methods with which the skilled worker is familiar, for example filtration and centrifugation.

In an especially preferred embodiment, the solids are not removed before the solids-loaded fermentation liquor is applied to the ion-exchange chromatography column. In this case, the flow of the solids-loaded fermentation liquor into the ion exchanger is advantageously against gravity so that the solids present do not lead to blocking (i.e. clogging) of the ion exchanger column.

If the metabolite produced via the microorganisms is a basic amino acid, the latter can advantageously be removed from the fermentation liquor by ion-exchange chromatography, employing an acidic cation exchanger column. In this case, the basic amino acid, for example lysine, is bound selectively on the ion exchanger column. Purification by washing, in particular with water, prior to elution is possible. Then, the basic amino acid is eluted with a suitable eluent, for example, ammonia water, preferably with 5% by volume strength ammonia water.

The use of ion-exchange chromatography for the removal or purification of basic amino acids such as lysine is described, for example, in WO 01/072689 and Lee et al., The use of ion exclusion chromatography as approved to the normal ion exchange chromatography to achieve a more efficient lysine recovery from fermentation broth, Enzyme and Microbial Technology 30 (2002), 798-303.

The fermentation residue which remains can be worked up, i.e. treated and/or processed, analogously to what will be described hereinbelow, giving rise to a proteinaceous by-product.

If the metabolite produced by the microorganisms is methionin, the product of value is advantageously isolated by centrifugation or filtration. Here, analogous conditions and procedures as have been described for other carbon feedstocks, for example in prior application DE 10359668.2, may be used. When the fermentation has ended, fermentation liquor generated is heated to dissolve all of the methionin. The solids are then separated off by centrifugation or filtration. The clear runoff from the solids separation step is preferably concentrated by partial or complete evaporation, during which process the methionin crystallizes out. Thereafter, the methionin is dried, if appropriate following a preceding further filtration step.

The solids separated by centrifugation or filtration essentially comprise the biomass produced during the fermentation and the nonmetabolized constituents of the saccharified starch solution, for example fibers. This remaining fermentation residue can be treated or processed analogously to what has been described below, giving a protein-containing secondary product.

If the metabolite produced by the microorganisms is pantothenic acid, the isolation of the product of value is likewise advantageously carried out by filtration or centrifugation. In this context, analogous conditions and procedures as have been described for other carbon feedstocks, for example in EP 1050219 and WO 01/83799, may be employed. Otherwise, work-up can be carried out analogously to what has been described above in the case of methionin. In the case of pantothenic acid, it is preferred additionally to carry out a pasteurization of all of the fermentation liquor before the solids are separated off. The clear runoff obtained from the solids separation step is preferably partially evaporated, if appropriate treated with calcium chloride and dried, preferably spray-dried.

To obtain the pantothenic acid, a procedure may also be followed in which, after step c), the cells and the undissolved, or solid, nonstarchy constituents are separated by means of decanter, centrifuges, filter technology or membrane technology (microfiltration, ultrafiltration, nanofiltration) and/or by a combination of these methods. The stream which is low in, or free from, solids contains the pantothenic acid. This stream can, for example, be further concentrated and/or subjected to a drying or formulation step. The solids-containing stream can be worked up as described hereinbelow to give a proteinaceous by-product.

If appropriate, the cells are lysed or destroyed. This can be effected directly after the fermentation. To this end, all of the fermentation liquor is subjected to a lysis or destruction step, which can be effected thermally, mechanically or chemically. The cells may also be lysed after removal of the solids. When doing so, only the solids-rich stream is subjected to the abovementioned lysis step.

In a preferred embodiment, the work-up of the pantothenic acid is carried out in such a way that the cells are destroyed thermally after fermentation and the cells and the nonstarchy solid constituents are removed by means of decanting, centrifuges, filter technology or membrane technology and/or a combination thereof. The stream which is low in, or free from, solids contains the pantothenic acid. This stream can be further concentrated, for example. It is advantageous before, during or after the concentration step to add adjuvants such as those mentioned hereinbelow to the liquor, which is low in solids. This makes it possible to reduce any foam formation and/or formation of a coating. The concentrated stream is then dried or formulated directly. Again, before, during or after the drying or formulation step, the adjuvants mentioned hereinbelow may be added to reduce the hygroscopicity of the product, to improve the flowing behavior of the product and/or to increase the storage stability. In this case, the solids-containing stream is preferably processed to give a proteinaceous by-product, analogously to what will be described hereinbelow.

A further preferred embodiment for working up pantothenic acid provides the possibility of adding adjuvants with specific cations as early as during the fermentation step. This is described for example in WO 02/072857.

Yet a further preferred embodiment for working up the pantothenic acid by means of centrifugation, decanting, ultrafiltration and/or diafiltration is described in WO 05/028659.

It is also possible to separate the pantothenic acid from the fermentation liquor by means of electrodialysis or ion exchange. However, these processes are not preferred since problems may be expected.

The fermentation residue which remains after isolation or depletion of the pantothenic acid, i.e. in particular the solids which have been separated off, can be treated or processed analogously to what has been described below, giving a proteinaceous secondary product.

If the metabolite produced by the microorganisms takes the form of polyhydroxyalkanoates, the isolation of the product of value is advantageously carried out by extraction with a solvent, such as described, for example, in U.S. Pat. No. 4,310,684 or EP 355307. The remaining solids can be removed in the customary manner, for example by filtration or centrifugation. Otherwise, work-up can be carried out analogously to what has been described above in the case of methionin. In the case of polyhydroxyalkanoates, it is preferred additionally to carry out a pasteurization of all of the fermentation liquor before the solids are separated off. The clear runoff obtained from the solids separation step is preferably partially evaporated, if appropriate treated with calcium chloride and dried, preferably spray-dried. The further purification of the polyhydroxyalkanoates is carried out in a known manner, such as described, for example in U.S. Pat. No. 4,310,684 or EP 355307.

The remaining fermentation residue, i.e. in particular the solids which have been separated off, can be treated or processed analogously to what has been described below giving a proteinaceous secondary product.

The fermentation liquor which remains after removal of the product of interest, for example a basic amino acid such as lysine, comprises essentially the biomass generated during the fermentation of the nonmetabolized constituents of the saccharified starch solution, such as, for example, fibers and unutilized sugars, and unutilized buffer and nutrient salts. These solids can be obtained from the fermentation liquor which remains analogously to the secondary product generated in the production of bioethanol (which is referred to as "distiller's dried grains with soluble (DDGS)" in that context, and marketed under this name). In this context, the fermentation liquor can essentially be separated completely from the solids, or only to some extent. The proteinaceous secondary product which is obtained in this manner, hereinbelow also referred to as protein composition, can be used both before and after further work-up or processing steps as foodstuff or feed additive for feeding animals, in particular agricultural livestock, especially preferably cattle, pigs and poultry, very especially preferably cattle.

The work-up or processing of the fermentation liquor to give a protein composition can be effected by methods which are known to the skilled worker, in particular by altering the dry-matter content (for example by drying or evaporation), grinding and formulation (for example addition of additives, shaping methods such as pelleting and extruding). Work-up and processing of the secondary product furthermore also comprises mixing with other feedstuffs or feed additives, for example in order to standardize the nutrient contents.

As a rule, the protein composition is prepared in such a way that at least some of the volatile constituents of the fermentation liquor are removed after the depletion or isolation of at least one metabolite in accordance with step c). This gives a protein composition in solid or semi-solid form. The content of the depleted or isolated metabolite in the remaining fermentation liquor is, as a rule, not more than 20% by weight, in particular not more than 15% by weight, specifically not more than 10% by weight and very specifically not more than 5% by weight, in each case based on the total weight of the remaining fermentation liquor.

To obtain the protein composition after removal of the product of interest, it is usual either to partially evaporate all of the remaining liquor in an evaporation step which is, as a rule, a multi-step procedure, and subsequently separating off the resulting solids, for example using a decanter, or else the solids are separated directly from all of the fermentation liquor. To remove the solids, it is possible to employ centrifugation, filtration, microfiltration, ultrafiltration, nanofiltration, reversed osmosis or a combination of these methods, for example in a multi-step plant. The solids which are separated off have, as a rule, a dry-matter content of in the range of from 10 to 80% by weight, preferably 15 to 60% by weight and especially preferably 20 to 50% by weight. The finished protein composition obtained by further work-up or processing advantageously has a dry-matter content of approximately 90% by weight, so that the risk of spoilage during storage is reduced.

The protein composition can also be obtained by concentrating the solid constituents of the fermentation liquor which remains after step c), using thermal methods (for example evaporation), mechanical methods (for example using filters, decanters, centrifuges) and the combinations of the above individual methods which are customary for the skilled worker. Concentration of the liquor gives a solid or semi-solid, for example pasty, residue which still comprises small amounts of the metabolite produced in accordance with the invention, as a rule in the range of from 0 to 10% by weight, and in particular in the range of from 0 to 5% by weight, based on the total weight of the residue, and the nonvolatile, generally solid, nonstarchy constituents of the starch source or at least large amounts thereof, frequently at least 90% by weight or all of the solid nonstarchy constituents of the starch source, and the biomass which is the result of the fermentation. This semi-solid or solid residue can be dried or formulated analogously to the unconcentrated fermentation liquor which remains after step c).

Part of the liquid phase which is separated off when the secondary product is obtained can be recirculated as process water. This recirculated portion of the liquid phase can advantageously be employed in the preparation of the sugar-containing liquid in accordance with step a), either all or some of it, or used for making buffer or nutrient salt solutions to be employed in the fermentation. When admixing recirculated process water in step a), it must be taken into consideration that an unduly high proportion may have an adverse effect on the fermentation as the result of an oversupply of certain minerals and ions, for example sodium ions and lactate ions. Preferably, the amount of recirculated process water when making the suspension for the purposes of starch liquefaction in accordance with the invention is therefore limited to not more than 75% by weight, preferably not more than 60% by weight and especially preferably not more than 50% by weight, in each case based on all of the water employed for making the suspension. The amount of process water when making the suspension in the preferred embodiment of step a2) is advantageously in the range of from 5 to 60% by weight and preferably in the range of from 10 to 50% by weight, in each case based on all of the water employed for making the suspension.

The portion of the liquid phase which is not recirculated into the process can be concentrated in a multi-step evaporation procedure to give a syrup. The syrup usually has a dry matter content in the range of from 20 to 90% by weight, preferably 30 to 80% by weight and especially preferably 40 to 70% by weight. This syrup can be mixed with the solids separated off during the decanting step (or any other manner) and then dried. Drying can be effected for example by means of drum dryers, spray dryers or paddle dryers, it being preferred to employ a drum dryer. Drying is preferably carried out in such a way that the resulting solid has a residual moisture content of not more than 30% by weight, preferably not more than 20% by weight and especially preferably not more than 10% by weight.

The properties of the dried secondary product which is present together with the solid fermentation constituents (i.e. of the protein composition) can be finished in a manner known per se with regard to a variety of parameters such as particle size, particle shape, susceptibility to dusting, hygroscopicity, stability, in particular storage stability, color, odor, flowing behavior, susceptibility to agglomerating, electrostatic charging, susceptibility to light and high temperatures, mechanical stability and redispersibility by adding formulation auxiliaries such as carriers and coating materials, binders and other additives.

The formulation auxiliaries which are conventionally employed include, for example, binders, carriers, powder-coating materials/flow improvers, furthermore color pigments, biocides, dispersants, antifoam agents, viscosity regulators, acids, lyes, antioxidants, stabilizers for enzymes, enzyme inhibitors, adsorbates, fats, fatty acids, oils or mixtures of these. Such formulation auxiliaries are advantageously employed as drying auxiliaries when using formulation and drying methods such as spray drying, fluidized-bed drying and lyophilization.

Examples of binders are carbohydrates, particularly sugars such as mono-, di-, oligo- and polysaccharides, for example dextrins, trehalose, glucose, glucose syrup, maltose, sucrose, fructose and lactose; colloidal substances such as animal proteins, for example gelatin, casein, in particular sodium caseinate, plant proteins, for example soya protein, pea protein, bean protein, lupin, zein, wheat protein, corn protein and rice protein, synthetic polymers, for example polyethylene glycol, polyvinyl alcohol and in particular the Kollidon brands from BASF, optionally modified biopolymers, for example lignin, chitin, chitosan, polylactid and modified starches, for example octenyl succinate anhydride (OSA); gums, for example acacia gum; cellulose derivatives, for example methylcellulose, ethylcellulose, (hydroxyethyl)methylcellulose (HEMC), (hydroxy-propylcellulose (HPMC), carboxymethylcellulose (CMC); flours, for example corn flour, wheat flour, rye flour, barley flour and rice flour.

Examples of carrier materials are carbohydrates, in particular the sugars which have been mentioned above as binders, and starches, for example corn starch, rice starch, potato starch, wheat starch and cassava starch; modified starches, for example octenyl succinate anhydride; cellulose and microcrystalline cellulose; inorganic minerals or loam, for example clay, coal, kieselguhr, silicic acid, talc and kaolin; coarse meals, for example coarse wheat meal, bran, for example wheat bran, the flours which have been mentioned above as binders; salts such as metal salts, in particular alkali metal and alkaline earth metal salts of organic acids, for example Mg, Ca, Zn, Na and K citrates, acetates, formates and hydrogen formates, inorganic salts, for example Mg, Ca, Zn, Na and K sulfates, carbonates, silicates or phosphates; alkaline earth metal oxides such as CaO and MgO; inorganic buffers such as alkali metal hydrogen phosphates, in particular sodium and potassium hydrogen phosphates, for example $K_2HPO_4$, $KH_2PO_4$ and $Na_2HPO_4$; and generally the adsorbents mentioned in connection with the production according to the invention of metabolites with a low melting point or of oily consistency.

Examples of powder-coating agents or flow adjuvants are kieselguhr, silicic acid, for example the Sipernat brands from Degussa; clay, coal, tallow and kaolin; the starches, modified starches, inorganic salts, salts of organic acids and buffers which have been mentioned above as carriers; cellulose and microcrystalline cellulose.

As regards other additives, examples which may be mentioned are color pigments such as $TiO_2$; biocides; dispersants; antifoams; viscosity regulators; inorganic acids such as phosphorus acids, nitric acid, hydrochloric acid, sulfuric acid; organic acids such as saturated or unsaturated mono- and dicarboxylic acids, for example formic acid, acetic acid, propionic acid, butyric acid, valeric acid, palmitic acid, stearic acid, oxalic acid, malonic acid, succinic acid, glutaric acid, adipic acid, pimelic acid, maleic acid and fumaric acid; lyes such as alkali metal hydroxides, for example NaOH and KOH; antioxidants; stabilizers for enzymes; enzyme inhibitors; adsorbates, fats; fatty acids and oils.

The amount of the abovementioned additives and, if appropriate, further additives such as coating materials can vary within wide limits depending on the specific requirements of the metabolite in question and depending on the properties of the additives employed, for example in the range of from 0.1 to 80% by weight, in particular in the range of from 5 to 70% by weight and specifically in the range from 10 to 60% by weight, in each case based on the total weight of the finished, formulated product or in each case based on the total weight of the finished, formulated product or composition.

The addition of formulation auxiliaries (also referred to as product confectioning or solids design) can be effected before, during or after processing the fermentation liquor, in particular during drying. The addition of formulation auxiliaries prior to concentration of the fermentation liquor which remains after step c) can be advantageous in particular for improving the processability of the substances or products to be worked up. The formulation auxiliaries can be added both to the secondary product, which is obtained in solid form, and to a solution or suspension comprising said secondary product, for example they can be added directly to the fermentation liquor after step c), or to a solution or suspension obtained during work-up and before the final drying step.

Thus, the auxiliaries can be mixed for example with a suspension obtained by concentrating the fermentation liquor which remains after step c); such a suspension can also be applied to a carrier material, for example by admixing. The addition of formulation auxiliaries is carried out in particular after drying, for example when applying coatings or layers of coatings to a dried particle. Further adjuvants may be added both after drying and after any coating step which has been carried out. The particles obtained by formulation processes can be dried down to the desired residual moisture content by employing the above-described drying processes.

All secondary products which are obtained in solid form, for example particles, granules and extrudates, can be coated with a coating, i.e. with at least one further layer of the substance. Coating is effected for example in mixers or fluidized beds in which the particles to be coated are fluidized and then sprayed with the coating material. The coating material can be in dry form, for example in the form of a powder, or in the form of a solution, dispersion, emulsion or suspension in a solvent, for example water, organic solvents and mixtures of these, in particular in water. If present, the solvent is removed by evaporation while it is sprayed onto the particles, or thereafter. Moreover, coating materials such as fats may also be applied in the form of melts.

Coating materials which can be sprayed on in the form of an aqueous dispersion or suspension are described for example in WO 03/059087. These include, in particular, polyolefins such as polyethylene, polypropylene, polyethylene waxes, waxes, inorganic and organic salts, Acronals, for example butyl acrolate/methyl acrolate copolymer, the Styrofan brands from BASF, for example those based on styrene and butadiene, and hydrophobic substances as described in WO 03/059086. When applying such materials, the solids content of the coating material is typically in the range of from 0.1 to 20% by weight, in particular in the range of from 0.2 to 10% by weight and specifically in the range of from 0.4 to 5% by weight, in each case based on the total weight of the formulated end product.

Coating materials which can be sprayed on in the form of solutions are, for example, polyethylene glycols, cellulose derivatives such as methylcellulose, hydroxypropyl-methylcellulose and ethylcellulose, polyvinyl alcohol, proteins such as gelatin, inorganic and organic salts, carbohydrates such as sugars, for example glucose, lactose, fructose, sucrose and trehalose; starches and modified starches. When applying such materials, the solids content of the coating material is typically in the range of from 0.1 to 20% by weight, in particular in the range of from 0.2 to 10% by weight and specifically in the range of from 0.4 to 5% by weight, in each case based on the total weight of the formulated end product.

Coating materials which can be sprayed on in the form of a melt are described for example in DE 199 29 257 and WO 92/12645. These include, in particular, polyethylene glycols, synthetic fats and waxes, for example Polygen WE® from BASF, natural fats such as animal fats, for example beeswax, and vegetable fats, for example candelilla wax, fatty acids, for example animal waxes, tallow fatty acids, palmitic acid, stearic acid, triglycerides, Edenor products, Vegeole products, Montan ester waxes, for example LuwaxE® from BASF. When applying such materials, the solids content of the coating material is typically in the range of from 1 to 25% by weight, in particular in the range of from 2 to 25% by weight and specifically in the range of from 3 to 20% by weight, in each case based on the total weight of the formulated end product.

After the drying and/or formulation steps, whole or ground cereal kernels, preferably corn, wheat, barley, millet/sorghum and/or rye may be added to the secondary product, or the protein composition.

The invention therefore furthermore relates to a protein composition from a sugar-based microbial fermentation, carried out in accordance with the invention, for the production of a metabolite having at least 3 C atoms or having at least 2 C atoms and at least 1 N atom, which protein composition is obtainable as described above. This protein composition usually comprises protein material, i.e. biomass from the fermentation, nonstarchy constituents of the starch source, in particular fibers, and fermentation product (metabolite). In particular, the protein composition essentially comprises the following dry-matter constituents:
a) 1 to 90% by weight, preferably 5 to 85% by weight and specifically 10 to 75% by weight of biomass from the fermentation;
b) 1 to 90% by weight, in particular 5 to 85% by weight, specifically 10 to 80% by weight and very specifically 15 to 75% by weight of nonstarchy constituents of the starch source, in particular fibers;
c) 0.01 to 10% by weight, in particular 0.1 to 5% by weight, specifically 0.2 to 5% by weight and very specifically 0.3 to 5% by weight of a microbial metabolite having at least 3 C atoms or having at least 2 C atoms and at least 1 N atom;
d) 0 to 90% by weight, in particular 5 to 80% by weight and specifically 10 to 70% by weight of customary formulation auxiliaries; and
e) 0 to 40% by weight, in particular 0.5 to 30% by weight and specifically 1 to 20% by weight of nonmetabolized further constituents of the fermentation liquor, in particular residues of sugars, starch, nutrient salts and/or buffer salts;
where the components a) to e) add up to 100% by weight of dry matter. In the present context, the term "essentially" means that the amount of other constituents which differ from a) to e) is low. As a rule, this amount will not exceed 10% by weight and in particular 5% by weight, in each case based on the total dry matter of the protein composition; specifically, this amount accounts for less than 1% by weight, in particular approximately 0% by weight.

The biomass (component a)) includes, in particular, the amount of crude protein in the protein composition. This amount usually accounts for at least 40% by weight and is generally in the range of from 40 to 90% by weight, specifically in the range of from 40 to 90% by weight, specifically in the range of from 45 to 85% by weight and specifically in the range of from 50 to 80% by weight, in each case based on the total dry matter of the protein composition.

The protein compositions according to the invention usually comprise one or more essential amino acids, in particular at least one amino acid selected from among lysine, methionine, threonine and tryptophan. The essential amino acids, in particular those mentioned, are, as a rule, in each case present in an amount which is increased by a factor of at least 1.5 in comparison with a traditional DDGS secondary product which is generated in a fermentative production of bioethanol. If the amino acid in question is present in the protein composition, the latter has, as a rule, a lysine content of at least 1% by weight, in particular in the range of from 1 to 5% by weight, a methionine content of at least 0.8% by weight, in particular in the range of from 0.8 to 5% by weight, a threonine content of at least 1.5% by weight, in particular in the range of from 1.5 to 5% by weight, and/or a tryptophan content of at least 0.4% by weight, in particular in the range of from 0.4 to 5% by weight, in each case based on the total dry matter of the protein composition.

Usually, the protein compositions according to the invention additionally comprise a small amount of water, frequently in the range of from 0 to 25% by weight, in particular in the range of from 0.5 to 15% by weight, specifically in the range of from 1 to 10% by weight and very specifically in the range of from 1 to 5% by weight of water, in each case based on the total weight of the protein composition.

The invention furthermore relates to a process as described above, wherein
(i) a portion of not more than 50% by weight is removed from the sugar-containing liquid medium obtained in step a) which comprises the non-starchy solid constituents of the starch feedstock and a fermentation as described in b) is carried out with the remainder in order to produce a first metabolite (A); and
(ii) all or some of the non-starchy solid constituents of the starch feedstock are separated from this portion and a fermentation as described in b) is carried out with this portion to produce a second metabolite (B), which is identical to or different from the metabolite (A).

In a preferred embodiment, the removal of the non-starchy solid constituents of (ii) is carried out in such a way that the solids content of the remainder of the sugar-containing liquid medium amounts to not more than 50% by weight, preferably not more than 30% by weight, especially preferably not more than 10% by weight and very especially preferably not more than 5% by weight.

This procedure makes possible, in the separate fermentation of (iii), the use of microorganisms for which certain minimum requirements, for example with regard to the oxygen transfer rate, must be met. Suitable microorganisms which are employed in the separate fermentation of (iii) are, for example, *Bacillus* species, preferably *Bacillus subtilis*. The compounds produced by such microorganisms in the separate fermentation are selected in particular from vitamins, cofactors and nutraceuticals, purine and pyrimidine bases, nucleosides and nucleotides, lipids, saturated and unsaturated fatty acids, aromatic compounds, proteins, carotenoids, specifically from vitamins, cofactors and nutraceuticals, proteins and carotenoids, and very specifically from riboflavin and calcium pantothenate.

In particular, this procedure permits the advantageous use of the process according to the invention even when the fine chemical produced is obtained, in the fermentation, as a solid.

A preferred embodiment of this procedure relates to parallel production of identical metabolites (A) and (B) in two separate fermentations. This is advantageous in particular in a case where different applications of the same metabolite have different purity requirements. Accordingly, the first metabolite (A), for example an amino acid to be used as feed additive, for example lysine, is produced using the solids-containing fermentation liquor and the same second metabolite (B), for example the same amino acid to be used as food additive, in the present case for example lysine, is produced using the solids-depleted fermentation liquor of (ii). Owing to the complete or partial removal of the non-starchy solid constituents, the complexity of the purification when working up the metabolite whose field of application has a higher purity requirement, for example as food additive, can be reduced.

In a further preferred embodiment of this procedure, the metabolite B produced by the microorganisms in the fermentation is riboflavin. To carry out the fermentation, analogous conditions and procedures as have been described for other carbon feedstocks, for example in WO 01/011052, DE 19840709, WO 98/29539, EP 1186664 and Fujioka, K.: New biotechnology for riboflavin (vitamin B2) and character of this riboflavin. Fragrance Journal (2003), 31(3), 4448, can be employed.

For example, the following procedure may be used for carrying out this variant of the process. A preferably large-volume fermentation is implemented for the production of metabolites A, for example of fine chemicals such as lysine, in accordance with process steps a) to c) according to the invention. In accordance with (i), some of the sugar-containing liquid medium obtained in step a) is removed and freed in accordance with (ii) completely or in part from the solids by customary methods, for example centrifugation or filtration. The sugar-containing liquid medium obtained therefrom, which is essentially fully or partially freed from the solids, is, in accordance with (ii), fed to a fermentation for the production of a metabolite B, for example riboflavin. The solids stream separated in accordance with (ii) is advantageously returned to the stream of the sugar-containing liquid medium of the large-volume fermentation.

The riboflavin-containing fermentation liquor which is thus generated in accordance with (ii) can be processed by analogous conditions and procedures as have been described for other carbon feedstocks, for example in DE 4037441, EP 464582, EP 438767 and DE 3819745. Following lysis of the cell biomass, the riboflavin, which is present in crystalline form, is separated, preferably be decanting. Other ways of separating solids, for example filtration, are also possible. Thereafter, the riboflavin is dried, preferably by means of spray dryers and fluidized-bed dryers. As an alternative, the riboflavin-containing fermentation mixture produced in accordance with (ii) can be processed under analogous conditions and using analogous procedures as described in, for example, EP 1048668 and EP 730034. After a pasteurization, the fermentation liquor is centrifuged, and the remaining solids-containing fraction is treated with a mineral acid. The riboflavin formed is removed from the aqueous-acidic medium by filtration, washed, if appropriate, and subsequently dried.

The solids which have been separated off can be processed within the scope of the large-volume fermentation process, as already previously described, which is operated in parallel to give a secondary product.

In a further preferred embodiment of this procedure, the metabolite B produced by the microorganisms in the fermentation is pantothenic acid. To carry out the fermentation, analogous conditions and procedures as have been described for other carbon feedstocks, for example in WO 01/021772, can be employed.

To carry out this process variant, a procedure such as described above for riboflavin may be followed. The sugar-containing liquid medium which has been purified in accordance with (ii) and which has preferably been essentially freed from the solids is fed into a fermentation in accordance with (ii) for the production of pantothenic acid. Here, the fact that the viscosity is reduced in comparison with the solids-containing liquid medium is particularly advantageous. The separated solids stream is preferably returned to the stream of the sugar-containing liquid medium of the large-volume fermentation.

The pantothenic-acid-containing fermentation liquor produced in accordance with (ii) can be processed under analogous conditions and using analogous procedures as have been described for other carbon feedstocks, for example in EP 1050219 and WO 01/83799. After all of the fermentation liquor has been pasteurized, the remaining solids are separated, for example by centrifugation or filtration. The clear runoff obtained in the solids separation step is partly evaporated, if appropriate treated with calcium chloride and dried, in particular spray dried.

The solids which have been separated off can be processed within the scope of the large-volume fermentation process, as already previously described, which is operated in parallel to give a secondary product.

In a further preferred embodiment of this procedure, the metabolite B produced by the microorganisms in the fermentation takes the form of polyhydroxyalkanoates. To carry out the fermentation, analogous conditions and procedures as have been described for other carbon feedstocks, for example in S. Y. Lee, Plastic Bacteria? Progress and prospects for polyhydroxyalkanoate production in bacteria; Tibtech, Vol. 14, (1996), pp. 431-438, can be employed.

To carry out this process variant, a procedure such as described above for riboflavin may be followed. The sugar-containing liquid medium which has been purified in accordance with (ii) and which has preferably been essentially freed from the solids is fed into a fermentation in accordance with (ii) for the production of polyhydroxyalkanoates. The clear runoff obtained in the solids separation step is partly evaporated, if appropriate treated with calcium chloride and dried, in particular spray dried.

The polyhydroxyalkanoate-containing fermentation liquor produced in accordance with (ii) can be processed under analogous conditions and using analogous procedures as have been described for other carbon feedstocks, for example in U.S. Pat. No. 4,310,684 and EP 355307. After all of the fermentation liquor has been pasteurized, the remaining solids are separated, for example by centrifugation or filtration. The clear runoff obtained in the solids separation step is partly evaporated, if appropriate treated with calcium chloride and dried, in particular spray dried. The further purification of the polyhydroxyalkanoates is carried out in a manner known per se, such as, for example, as described in U.S. Pat. No. 4,310, 684 or EP 355307.

The solids which have been separated off can be processed within the scope of the large-volume fermentation process, as already previously described, which is operated in parallel to give a secondary product.

The examples which follow are intended to illustrate individual aspects of the present invention, but are in no way to be understood as limiting.

EXAMPLES

I. Milling the Starch Feedstock

The millbases employed hereinbelow were produced as follows. Whole maize kernels were ground completely using a rotor mill. Using different beaters, milling paths or screen elements, three different degrees of fineness were obtained. A screen analysis of the millbase by means of a laboratory vibration screen (vibration analyzer: Retsch Vibrotronic type VE1; screening time 5 minutes, amplitude: 1.5 mm) gave the results listed in Table 1.

TABLE 1

| | Experiment number | | |
|---|---|---|---|
| | T 70/03 | T 71/03 | T 72/03 |
| <2 mm/% | 99.4 | 100 | 100 |
| <0.8 mm/% | 66 | 100 | 99 |
| <0.63 mm/% | 58.6 | 98.5 | 91 |
| <0.315 mm/% | 48.8 | 89 | 65 |
| <0.1 mm/% | | 25 | 9.6 |
| <0.04 mm/% | | 8 | 3.2 |
| Millbase in total | 20 kg | 11.45 kg | 13.75 kg |

II. Enzymatic Starch Liquefaction and Starch Saccharification

II. 1. Without Phytase in the Saccharification Step

II. 1a) Enzymatic Starch Liquefaction 320 g of dry-milled corn meal (T71/03) were suspended with 480 g of water and admixed with 310 mg of calcium chloride by continuous stirring. Stirring was continued during the entire experiment. After the pH was brought to 6.5 with $H_2SO_4$ and the mixture had been heated to 35° C., 2.4 g of Termamyl 120 type L (Novozymes A/S) were added. In the course of 40 minutes, the reaction mixture was heated to a temperature of 86.5° C., the pH being readjusted with NaOH to the above value, if necessary. Within 30 minutes, a further 400 g of the dry-milled corn meal (T71/03) were added, during which process the temperature was raised to 91° C. The reaction mixture was held at this temperature for approximately 100 minutes. A further 2.4 g of Termamyl 120L were subsequently added and the temperature was held for approximately 100 minutes. The progress of the liquefaction was monitored during the experimentation using the iodine-starch reaction. The temperature was finally raised to 100° C. and the reaction mixture was boiled for a further 20 minutes. At this point in time, starch was no longer detectable. The reactor was cooled to 35° C.

II. 1b) Saccharification

The reaction mixture obtained in II. 1a) was heated to 61° C., with constant stirring. Stirring was continued during the entire experiment. After the pH had been brought to 4.3 with $H_2SO_4$, 10.8 g (9.15 ml) of Dextrozyme GA (Novozymes A/S) were added. The temperature was held for approximately 3 hours, during which time the progress of the reaction was monitored with glucose test strips (S-Glucotest by Boehringer). The results are listed in Table 2 hereinbelow. The reaction mixture was subsequently heated to 80° C. and then cooled. This gave approximately 1180 g of liquid product with a density of approximately 1.2 kg/l and a dry matter content which, as determined by infrared dryer, amounted to approximately 53.7% by weight. After washing with water, the dry matter content (without water-soluble constituents) was approximately 14% by weight. The glucose content of the reaction mixture, as determined by HPLC, amounted to 380 g/l (see Table 2, sample No. 7).

TABLE 2

| Sample No. | min (from addition of glucoamylase) | Glucose concentration in supernatant [g/l] |
|---|---|---|
| 1 | 5 | 135 |
| 2 | 45 | 303 |
| 3 | 115 | 331 |
| 4 | 135 | 334 |
| 5 | 165 | 340 |
| 6 | 195 | 359 |
| 7 | 225 | 380 |

II. 2. With Phytase in the Saccharification Step

II. 2a) Starch Liquefaction

A dry-milled corn meal sample is liquefied as described in II. 1a).

II. 2b) Saccharification

The reaction mixture obtained in II. 2a) is heated to 61° C. with constant stirring. Stirring is continued during the entire experiment. After the pH has been brought to 4.3 with $H_2SO_4$, 10.8 g (9.15 ml) of Dextrozyme GA (Novozymes A/S) and 70 µl of phytase (700 units of phytase, Natuphyt Liquid 10000L from BASF AG) is added. The temperature is held for approximately 3 hours, during which time the progress of the reaction is monitored with glucose test strips (S-Glucotest by Boehringer). The reaction mixture is subsequently heated to 80° C. and then cooled. The product obtained is dried by means of infra-red dryer and washed with water. The glucose content in the reaction mixture is determined by HPLC.

II. 3 Further Protocols for the Enzymatic Starch Liquefaction and Starch Saccharification

II. 3a) Corn Meal 360 g of deionized water are introduced into a reaction vessel. 1.54 ml of $CaCl_2$ stock solution (100 g $CaCl_2 \times 2H_2O$/l) are added to a final concentration of approximately 70 ppm $Ca^{2+}$ in the mash. 240 g of corn meal are slowly run into the water, with constant stirring. After the pH has been brought to 6.5 using 50% by weight of aqueous NaOH solution, 4.0 ml (=2% by weight of enzyme/dry matter) of Termamyl 120 L type L (Novozymes A/S) are added. The mash is then rapidly heated to 85° C. During this process, it is necessary to constantly monitor and, if appropriate, adjust the pH.

After the final temperature has been reached, the addition of further meal, initially 50 g of meal, is started. In addition, 0.13 ml of $CaCl_2$ stock solution is added to the mash in order to maintain the $Ca^{2+}$ concentration at 70 ppm. During the addition, the temperature is held at a constant 85° C. A period of at least 10 minutes is allowed to pass in order to ensure that the reaction is complete before a further portion (50 g of meal and 0.13 ml of $CaCl_2$ stock solution) is added. After the addition of two portions, 1.67 ml of Termamyl are added; thereafter, two further portions (in each case 50 g of meal and 0.13 ml of $CaCl_2$ stock solution) are added. A dry matter content of 55% by weight is reached. After the addition, the temperature is raised to 100° C. and the mash is boiled for 10 minutes.

A sample is taken and cooled to room temperature. After dilution of the sample with deionized water (approximately 1:10), one drop of concentrated Lugol's solution (mixture of 5 g of 1 and 10 g of Kl per liter) is added. A deep blue color indicates a residual starch content; the color changes to brown when all of the starch has been hydrolyzed. When the test indicates that starch is still remaining, the temperature is again brought down to 85° C. and kept constant. A further 1.67 ml of Termamyl are added until the iodine/starch reaction is negative.

The mixture, which tests negative for starch, is then brought to 61° C. for the subsequent saccharification reaction. The pH is brought to 4.3 by addition of 50% strength sulfuric acid. The pH is maintained at this value during the course of the reaction. The temperature is maintained at 61° C. 5.74 ml (=1.5% by weight of enzyme/dry matter) of Dextrozym GA (Novozymes A/S) are added in order to convert the liquefied starch into glucose. The reaction is allowed to proceed for one hour. To inactivate the enzyme, the mixture is heated at 85° C. Sterile containers are filled with the hot mixture and, after cooling, stored at 4° C.

II. 3b) Rye Meal (Including Pretreatment with Cellulase/Hemicellulase)

360 g of deionized water are introduced into a reaction vessel. 155 g of rye meal are slowly run into the water, with constant stirring. The temperature is kept constant at 50° C. After the pH has been brought to 5.5 using 50% by weight of aqueous NaOH solution, 3.21 ml (=2.5% by weight of enzyme/dry matter) of Viscozyme L (Novozymes A/S) are added. After 30 minutes, the addition of further meal is started; initially, 55 g of meal are added. After a further 30 minutes, another 50 g of meal are added; 30 minutes later, yet another 40 g of meal are added. Liquefaction can be started 30 minutes after the last addition.

1.7 ml of $CaCl_2$ stock solution (100 g $CaCl_2 \times 2H_2O$/l) are added. After the pH has been brought to 6.5 using 50% by weight of aqueous NaOH solution, 5.0 ml (=2% by weight of enzyme/dry matter) of Termamyl 120 L type L (Novozymes A/S) are added. The mash is then rapidly heated to 85° C. During this process, the pH is continuously monitored and, if appropriate, adjusted.

After the final temperature has been reached, the addition of further meal, initially 60 g of meal, is started. In addition, 0.13 ml of $CaCl_2$ stock solution is added to the mash in order to maintain the $Ca^{2+}$ concentration at 70 ppm. During the addition, the temperature is held at a constant 85° C. A period of at least 10 minutes is allowed to pass in order to ensure that the reaction is complete before a further portion (40 g of meal and 0.1 ml of $CaCl_2$ stock solution) is added. After the addition of two portions, 1.1 ml of Termamyl are added; thereafter, further portions (40 g of meal and 0.1 ml of $CaCl_2$ stock solution) are added. A dry matter content of 55% by weight is reached. After the addition, the temperature is raised to 100° C. and the mash is boiled for 10 minutes.

A sample is taken and cooled to room temperature. After dilution of the sample with deionized water (approximately 1:10), one drop of concentrated Lugol's solution (mixture of 5 g of 1 and 10 g of Kl per liter) is added. A deep blue color indicates a residual starch content; the color changes to brown when all of the starch has been hydrolyzed. When the test indicates that starch is still remaining, the temperature is again brought down to 85° C. and kept constant. A further 1.1 ml of Termamyl are added until the iodine/starch reaction is negative.

The mixture, which tests negative for starch, is then brought to 61° C. for the subsequent saccharification reaction. The pH is brought to 4.3 by addition of 50% strength sulfuric acid. The pH is maintained at this value during the course of the reaction. The temperature is maintained at 61° C. 5.74 ml (=1.5% by weight of enzyme/dry matter) of Dextrozym GA (Novozymes A/S) are added in order to convert the liquefied starch into glucose. The reaction is allowed to proceed for one hour. To inactivate the enzyme, the mixture is heated at 85° C. Sterile containers are filled with the hot mixture and, after cooling, stored at 4° C.

II. 3c) Wheat Flour (Including Pretreatment with Xylanase)

360 g of deionized water are introduced into a reaction vessel. The water is heated to 55° C., and the pH is adjusted to 6.0 using 50% by weight of aqueous NaOH solution. After temperature and pH have been adjusted, 3.21 ml (=2.5% by weight of enzyme/dry matter) Shearzyme 500L (Novozymes A/S) are added. 155 g of wheat flour are slowly run into the solution, with constant stirring. The temperature and the pH are kept constant. After 30 minutes, the addition of further meal is started; initially, 55 g of meal are added. After a further 30 minutes, another 50 g of meal are added; 30 minutes later, yet another 40 g of meal are added. Liquefaction can be started 30 minutes after the last addition.

The liquefaction and saccharification are carried out as described under II. 3b.

III. Construction of a Lysine-Overproducing C. glutamicum Strain ATCC13032 lysC$^{fbr}$

III. 1 Construction of the Plasmid pCIS lysC

In the first step of the strain construction, an allelic substitution of the wild-type gene which encodes the enzyme aspartate kinase (lysC) was carried out in C. glutamicum ATCC13032. Here, a nucleotide substitution was carried out in the lysC gene so that, in the resulting protein, the amino acid Thr at position 311 was replaced by an Ile. Starting from the chromosomal DNA from ATCC13032 as template for a PCR reaction, lysC was amplified with the oligonucleotide primers

```
                                         (SEQ ID NO: 1)
5'-GAGAGAGAGACGCGTCCCAGTGGCTGAGACGCATC-3'
and
                                         (SEQ ID NO: 2)
5'-CTCTCTCTGTCGACGAATTCAATCTTACGGCCTG-3'
``` with the aid of the Pfu-Turbo PCR system (Stratagene, USA) following the manufacturer's instructions. Chromosomal DNA from C. glutamicum ATCC 13032 was prepared by the method of Tauch et al. (1995) Plasmid 33:168-179 or Eikmanns et al. (1994) Microbiology 140:1817-1828. The amplified fragment is flanked at its 5' end by an SalI restriction cleavage site and at its 3' end by an MluI restriction cleavage site. Prior to cloning, the amplified fragment was digested with these two restriction enzymes and purified with GFX™ PCR, DNA and Gel Band Purification Kit (Amersham Pharmacia, Freiburg).

The resulting polynucleotide was cloned via the SalI and MluI restriction cleavages into pCLIK5 MCS integrativ SacB, hereinbelow referred to as pCIS, (SEQ ID NO: 3) and transformed into *E. coli* XL-1 blue. A selection for plasmid-harboring cells was achieved by plating on kanamycin (20 µg/ml) containing LB agar (Lennox, 1955, Virology, 1:190). The plasmid was isolated and the expected nucleotide sequence was verified by sequencing. The preparation of the plasmid DNA was carried out using methods and materials from Quiagen. Sequencing reactions were carried out by the method of Sanger et al. (1977) Proceedings of the National Academy of Sciences USA 74:5463-5467. The sequencing reactions were separated by means of ABI Prism 377 (PE Applied Biosystems, Weiterstadt) and evaluated. The resulting plasmid was referred to as pCIS lysC (SEQ ID NO:4). It comprises the following essential portions:

| Position | Sequence type | Description |
|---|---|---|
| 155-1420 | CDS | LysC |
| Complement (3935 . . . 5356) | CDS | sacB\*Bacillus subtilis* |
| Complement (5357 . . . 5819) | promoter | Promoter\sacB |
| Complement (3913 . . . 3934) | C region | sacB\downstream region |
| 1974 . . . 2765 | CDS | kanamycin resistance |
| Complement (3032 . . . 3892) | CDS | replication origin\*E. coli*\plasmid pMB |

III. 2 Mutagenesis of the *C. glutamicum* lysC Gene

The directed mutagenesis of the *C. glutamicum* lysC gene was carried out using the QuickChange Kit (Stratagene, USA) following the manufacturer's instructions. The mutagenesis was carried out in the plasmid pCIS lysC (SEQ ID NO:4). The following oligonucleotide primers were synthesized for the substitution of thr 311 by 311 ile with the aid of the Quickchange method (Stratagene):

```
                                               (SEQ ID NO: 5)
5'-CGGCACCACCGACATCATCTTCACCTGCCCTCGTTCCG-3'

(SEQ ID NO: 6)
5'-CGGAACGAGGGCAGGTGAAGATGATGTCGGTGGTGCCG-3'
```

The use of these oligonucleotide primers in the Quickchange reaction leads, in the lysC gene (SEQ ID NO:7), to a substitution of the nucleotide in position 932 (of C by T). The resulting amino acid substitution Thr311 Ile in the lysC gene is verified by the sequencing reaction after transformation into *E. coli* XL1-blue and plasmid preparation. The plasmid was named pCIS lysC thr311 ile (SEQ ID NO:8). It comprises the following essential portions:

| Position | Sequence type | Description |
|---|---|---|
| 155-1420 | CDS | LysC (thr311ile) |
| Complement (3935 . . . 5356) | CDS | sacB\*Bacillus subtilis* |
| Complement (5357 . . . 5819) | promoter | promoter\sacB |
| Complement (3913 . . . 3934) | C region | sacB\downstream region |
| 1974 . . . 2765 | CDS | kanamycin resistance |
| Complement (3032 . . . 3892) | CDS | replication origin\*E. coli*\plasmid pMB |

III. 3 Transformation of pCIS lysC thr311 ile into *C. glutamicum* (Strain ATCC13032)

The plasmid pCIS lysC thr311 ile was transformed into *C. glutamicum* ATCC13032 by means of electroporation as described by Liebl et al., FEMS Microbiology Letters 53:299-303 (1989). Modifications of the protocol are described in DE 10046870. The chromosomal arrangement of the lysC locus of individual transformants was verified using standard methods by means of Southern blot and hybridization as described in Sambrook et al., Molecular Cloning. A Laboratory Manual, Cold Spring Harbor (1989). It was thereby ensured that the transformants were those which have the transformed plasmid integrated at the lysC locus by homologous recombination. After such colonies have been grown overnight in media without antibiotic, the cells are plated onto a sucrose CM agar medium (10% sucrose) and incubated for 24 hours at 30° C.

Since the sacB gene which is present in the vector pCIS lysC thr311 ile converts sucrose into a toxic product, only those colonies which have the sacB gene deleted by a second homologous recombination step between the wild-type gene lysC and the mutated gene lysC thr311 ile are capable of growing. During the homologous recombination, either the wild-type gene or the mutated gene can be deleted together with the sacB gene. When the sacB gene is removed together with the wild-type gene, a mutated transformant results.

Growing colonies were picked out and studied for a kanamycin-sensitive phenotype. Clones with deleted sacB must simultaneously demonstrate kanamycin-sensitive growth behavior. Such kanamycin-sensitive clones were studied for their lysine productivity in a shake flask. For comparison, the untreated *C. glutamicum* ATCC13032 was grown. Clones whose lysine production was increased over the control were selected, chromosomal DNA was obtained, and the corresponding region of the lysC gene was amplified by a PCR reaction (Pfu-Turbo PCR Systems; Stratagene, USA) following the manufacturer's instructions and sequenced (by the method of Sanger et al., loc. cit.). Such a clone with the characteristic of enhanced lysine synthesis and confirmed mutation in lysC at position 932 was referred to as ATCC13032 lysC$^{fbr}$.

Example 1 a) Enzymatic Starch Liquefaction and Starch Saccharification 500 g of dry-milled corn meal were suspended in 750 ml of water and again milled finely in a blender. The suspension was divided into 4 samples No. 1 to No. 4, each of which was treated with approximately 3 g of heat-stable α-amylase (samples No. 1 and 2: Termamyl L; samples No. 3 and 4: Spezyme). Samples No. 2 and 4 were subsequently treated with approx. 7 g/l glucoamylase (sample No. 2: Dextrozyme GA; sample no. 4: Optidex). This gave pale yellow viscous samples whose solids content was in each case separated by centrifugation, during which process a layer of hydrophobic solids floated on top of the clear liquid phase.

The clear supernatant of the resulting samples, in concentrated form and in 10-fold dilution, was analyzed by means of HPLC either ignoring or taking into consideration the spun-down pellet. When the pellet was taken into consideration, a pellet dry-matter content of 50% by weight was assumed. The results, based on the starting sample, are listed in Table 3 hereinbelow.

TABLE 3

| | Sample No. | | | |
|---|---|---|---|---|
| | 1 | 2 | 3 | 4 |
| Supernatant, 10-fold dilution, without pellet | | | | |
| Glucose [g/kg] | 73.0 | 287.3 | 63.7 | 285.1 |
| Fructose [g/kg] | 3.4 | 2.3 | 5.3 | 2.7 |
| Oligosaccharides [g/kg] | 202.1 | 38.2 | 150.8 | 31.5 |
| Total sugars [g/kg] | 278 | 328 | 220 | 319 |
| Supernatant, 10-fold dilution, with pellet | | | | |
| Glucose [g/kg] | | 178 | | 168 |
| Total sugars [g/kg] | 172 | 203 | 130 | 188 |
| Supernatant, without dilution, with pellet | | | | |
| Glucose [g/kg] | | 198 | | 189 | b) Fermentation

Two maize meal hydrolyzates obtained in accordance with Example II. 1 were employed in shake-flask experiments using *Corynebacterium glutamicum* (flasks 4-9). In addition, a wheat flour hydrolyzate prepared analogously to Example II. 1 was used in parallel (flasks 1-3).

1b.1) Preparation of the Inoculum

The cells are streaked onto sterile CM agar (composition: see Table 4; 20 minutes at 121° C.) and then incubated for 48 hours at 30° C. The cells are subsequently scraped from the plates and resuspended in saline. 25 ml of the medium (see Table 5) in 250 ml Erlenmeyer flasks are inoculated in each case with such an amount of the cell suspension thus prepared that the optical density reaches an $OD_{600}$ value of 1 at 600 nm.

TABLE 4

| Composition of CM agar | |
|---|---|
| Concentration | Constituent |
| 10.0 g/l | D glucose |
| 2.5 g/l | NaCl |
| 2.0 g/l | Urea |
| 10.0 g/l | Bacto peptone (Difco) |
| 5.0 g/l | Yeast extract (Difco) |
| 5.0 g/l | Beef Extract (Difco) |
| 22.0 g/l | Agar |

1b.2) Preparation of the Fermentation Liquor

The compositions of the flask media 1 to 9 are listed in Table 5.

TABLE 5

| Flask media | | | |
|---|---|---|---|
| | Flask No. | | |
| | 1-3 | 4-6 | 7-9 |
| Wheat 399.66 g/kg** | 250 g/l*** | | |
| Corn I 283.21 g/kg** | | 353 g/l*** | |
| Corn II 279.15 g/kg** | | | 358 g/l*** |
| $(NH_4)_2SO_4$ | | 50 g/l | |
| $MgSO_4 \cdot 7H_2O$ | | 0.4 g/l | |
| $KH_2PO_4$ | | 0.6 g/l | |
| $FeSO_4 \cdot 7H_2O$ | | 2 mg/l | |
| $MnSO_4 \cdot H_2O$ | | 2 mg/l | |
| Thiamine•HCl | | 0.3 mg/l | |
| Biotin | | 1 mg/l | |

TABLE 5-continued

| Flask media | | | |
|---|---|---|---|
| | Flask No. | | |
| | 1-3 | 4-6 | 7-9 |
| $CaCO_3$ | | 50 g/l | |
| pH* | | 7.8 | |

*to be adjusted with dilute aqueous NaOH solution
**glucose concentration in the hydrolyzate
***amount of hydrolyzate weighed in per liter of medium After the inoculation, the flasks were incubated for 48 hours at 30° C. and with shaking (200 rpm) in a humidified shaker. After the fermentation was terminated, the sugar and lysine contents were determined by HPLC. The HPLC was carried out with an Agilent 1100 series LC system. Precolumn derivatization with ortho-phthaldehyde permits the quantification of the amino acid formed; the product mixture is separated using an Agilent Hypersil AA column. The results are compiled in Table 6.

TABLE 6

| Flask No. | Fructose g/l | Glucose g/l | Sucrose g/l | Total sugars g/l |
|---|---|---|---|---|
| 1 | 0.00 | 0.00 | 4.71 | 4.71 |
| 2 | 0.00 | 7.75 | 4.82 | 12.57 |
| 3 | 0.00 | 13.85 | 4.57 | 18.42 |
| 4 | 0.00 | 17.20 | 11.38 | 28.58 |
| 5 | 0.00 | 21.08 | 11.31 | 32.39 |
| 6 | 0.00 | 25.51 | 11.29 | 36.80 |
| 7 | 0.00 | 32.59 | 9.83 | 42.42 |
| 8 | 0.00 | 24.10 | 10.01 | 34.11 |
| 9 | 0.00 | 39.26 | 9.94 | 49.20 |

In all flasks, lysine was produced in comparable amounts in the order of approximately 30 to 40 g/l, corresponding to the yield obtained in a standard fermentation with glucose nutrient solution.

Example 2

Fermentation

Using a cornmeal hydrolyzate obtained as described in Example II. 1, a fermentation is carried out analogously to Example 1b), using the strain ATCC13032 $lysC^{fbr}$ described under III. The cells are incubated on sterile CM agar (composition Table 4; 20 minutes at 121° C.) for 48 hours at 30° C. The cells are subsequently scraped from the plates and resuspended in saline. 25 ml of the medium 1 or 2 (see Table 5) in 250 ml Erlenmeyer flasks are inoculated in each case with such an amount of the cell suspension thus prepared that the optical density reaches an $OD_{600}$ value of 1 at 610 nm. The samples are then incubated for 48 hours at 200 rpm and 30° C. in a humidified shaker (relative atmospheric humidity 85%). The lysine concentration in the media is determined by HPLC. In all cases, approximately identical lysine quantities were produced.

Example 3

A cornmeal hydrolyzate obtained in accordance with Example II. 3a was employed in shake-flask experiments using *Corynebacterium glutamicum* (ATCC13032 $lysC^{fbr}$) (flasks 1+2). In addition, a rye meal hydrolyzate (flasks 5+6) and a wheat meal hydrolyzate (flasks 3+4), prepared analogously to Example II. 3, were employed in parallel.

3.1) Preparation of the Inoculum

After streaking onto sterile CM+CaAc agar (composition: see Table 7; 20 minutes at 121° C.), the cells were incubated for 48 hours at 30° C., and then inoculated onto a fresh plate and incubated overnight at 30° C. The cells are subsequently scraped from the plate and resuspended in saline. 23 ml of the medium (see Table 8) in 250 ml Erlenmeyer flasks, equipped with two baffles, are inoculated in each case with such an amount of the cell suspension thus prepared that the optical density reaches an $OD_{610}$ value of 0.5 at 610 nm.

TABLE 7

Composition of the CM + CaAc agar plates

| Concentration | Constituent |
|---|---|
| 10.0 g/l | D-glucose |
| 2.5 g/l | NaCl |
| 2.0 g/l | Urea |
| 5.0 g/l | Bacto Peptone (Difco) |
| 5.0 g/l | Yeast extract (Difco) |
| 5.0 g/l | Beef extract (Difco) |
| 20.0 g/l | Casamino acids |
| 20.0 g/l | Agar |

3.2) Preparation of the Fermentation Liquor

The compositions of the flask media 1 to 6 are shown in Table 8. A suitable amount of glucose solution was used in the control medium in place of meal hydrolyzate.

TABLE 8

Flask media

| | Flask No. | | |
|---|---|---|---|
| | 1 + 2 | 3 + 4 | 5 + 6 |
| Corn 344 g/kg** | 174 g/l*** | | |
| Wheat 343 g/kg** | | 175 g/l*** | |
| Rye 310 g/kg** | | | 194 g/l*** |
| $(NH_4)_2SO_4$ | | 20 g/l | |
| Urea | | 5 g/l | |
| $KH_2PO_4$ | | 0.113 g/l | |
| $K_2HPO_4$ | | 0.138 g/l | |
| ACES | | 52 g/l | |
| MOPS | | 21 g/l | |
| Citric acid × $H_2O$ | | 0.49 g/l | |
| 3,4-Dihydroxybenzoic acid | | 3.08 mg/l | |
| NaCl | | 2.5 g/l | |
| KCl | | 1 g/l | |
| $MgSO_4 \times 7H_2O$ | | 0.3 g/l | |
| $FeSO_4 \times 7H_2O$ | | 25 mg/l | |
| $MnSO_4 \times 4\text{-}6H_2O$ | | 5 mg/l | |
| $ZnCl_2$ | | 10 mg/l | |
| $CaCl_2$ | | 20 mg/l | |
| $H_3BO_3$ | | 150 µg/l | |
| $CoCl \times 6H_2O$ | | 100 µg/l | |
| $CuCl_2 \times 2H_2O$ | | 100 µg/l | |
| $NiSO_4 \times 6H_2O$ | | 100 µg/l | |
| $Na_2MoO_4 \times 2H_2O$ | | 25 µg/l | |
| Biotin (vit. H) | | 1050 µg/l | |
| Thiamine × HCl (vit. $B_1$) | | 2100 µg/l | |
| Nicotinamide | | 2.5 mg/l | |
| Pantothenic acid | | 125 mg/l | |
| Cyanocobalamine (vit. $B_{12}$) | | 1 µg/l | |
| 4-Aminobenzoic acid (PABA; vit. $H_1$) | | 600 µg/l | |
| Folic acid | | 1.1 µg/l | |
| Pyridoxine (vit. $B_6$) | | 30 µg/l | |
| Riboflavin (vit. $B_2$) | | 90 µg/l | |
| CSL | | 40 ml/l | |
| pH* | | 6.85 | |

*to be adjusted with dilute aqueous NaOH solution
**glucose concentration in the hydrolyzate
***amount of hydrolyzate weighed in per liter of medium After the inoculation, the flasks were incubated in a humidified shaker for 48 hours at 30° C., with shaking (200 rpm). After the fermentation was terminated, the glucose and lysine contents were determined by HPLC. The HPLC analyses were carried out with an Agilent 1100 series LC system. The quantification of the amino acids requires a pre-column derivatization with ortho-phthalaldehyde, the separation was performed on an Agilent Zorbax Extend C18 column. The results are compiled in Table 9.

TABLE 9

| Flask No. | Glucose [g/l] | Lysine [g/l] |
|---|---|---|
| 1 | 1.2 | 12.0 |
| 2 | 1.2 | 10.8 |
| 3 | 0.2 | 10.6 |
| 4 | 0.2 | 10.0 |
| 5 | 0.0 | 11.1 |
| 6 | 0.0 | 9.5 |

In all flasks, lysine was produced in comparable amounts in the order of approximately 10 to 12 g/l, corresponding to the yield obtained in a standard fermentation with a glucose nutrient solution.

3.3) Isolation of the Lysine

To isolate the lysine, it is usual to carry out a first step in which the solids are separated from the fermentation liquor by means of centrifugation. Filtration methods such as, for example, membrane filtrations may also be employed as an alternative to centrifugation. The fermentation liquor, which is now free from solids, is then acidified (for example using sulfuric acid), whereby lysine is present in singly or doubly protonated form. This acidified liquor is subsequently passed over a cation exchanger so that the lysine binds to the ion exchanger. After washing with water, ammonia water is then passed over the ion exchanger in order to eluate the lysine. The eluate is evaporated; the lysine, which is now present in the eluate in the form of the free base, is subsequently converted into lysine hydrochloride by addition of hydrochloric acid and crystallizes out. The crystals are separated off from the crystal suspension by centrifugation and then dried in a final step. This procedure gives a crystalline lysine of high purity (≥98.5% by weight lysine HCl). Detailed descriptions of this procedure, but also alternative methods for the lysine work-up, can be found in "Ikeda, M.: Amino Acid Production Processes. Advances in Biochemical Engineering/Biotechnology, Vol. 79 (2003), 1-35" and "Hermann, T.: Industrial production of amino acids by coryneform bacteria. Journal of Biotechnology 104 (2003), 155-172".

Example 4

A corn meal hydrolyzate obtained as described in Example II. 3a was employed in shake-flask experiments (flasks 1-3). *Bacillus* PA824 (detailed description in WO 02/061108) was employed as the pantothenate-producing strain. In addition, a rye meal hydrolyzate (flasks 7-9) and a wheat meal hydrolyzate (flasks 4-6), prepared analogously to Example II. 3, were used in parallel.

4.1) Preparation of the Inoculum 42 ml of the preculture medium (see Table 10) in 250 ml Erlenmeyer flasks equipped with two baffles are inoculated in each case with 0.4 ml of a frozen culture and incubated in a humidified shaker for 24 hours at 43° C., with shaking (250 rpm).

TABLE 10

| Composition of the preculture medium | |
|---|---|
| Constituent | Concentration |
| Maltose | 28.6 g/l |
| Soya meal | 19.0 g/l |
| $(NH_4)_2SO_4$ | 7.6 g/l |
| Monosodium glutamate | 4.8 g/l |
| Sodium citrate | 0.95 g/l |
| $FeSO_4 \times 7H_2O$ | 9.5 mg/l |
| $MnCl_2 \times 4H_2O$ | 1.9 mg/l |
| $ZnSO_4 \times 7H_2O$ | 1.4 mg/l |
| $CoCl_2 \times 6H_2O$ | 1.9 mg/l |
| $CuSO_4 \times 5H_2O$ | 0.2 mg/l |
| $Na_2MoO_4 \times 2H_2O$ | 0.7 mg/l |
| $K_2HPO_4 \times 3H_2O$ | 15.2 g/l |
| $KH_2PO_4$ | 3.9 g/l |
| $MgCl_2 \times 6H_2O$ | 0.9 g/l |
| $CaCl_2 \times 2H_2O$ | 0.09 g/l |
| MOPS | 59.8 g/l |
| pH* | 7.2 |

*to be adjusted with dilute aqueous KOH solution 42 ml of the main culture medium (see Table 11) in 250 ml Erlenmeyer flasks, equipped with two baffles, are inoculated with in each case 1 ml of preculture.

4.2) Preparation of the Fermentation Liquor

The compositions of the flask media 1 to 9 are shown in Table 11. A suitable amount of glucose solution was used in the control medium in place of meal hydrolyzate.

TABLE 11

| | Flask media | | |
|---|---|---|---|
| | Flask No. | | |
| | 1-3 | 4-6 | 7-9 |
| Corn | 381.4 g/kg** | 75 g/l*** | |
| Wheat | 342.0 g/kg** | | 84 g/l*** |
| Rye | 303.0 g/kg** | | 94 g/l*** |
| Soya meal | | 19.0 g/l | |
| $(NH_4)_2SO_4$ | | 7.6 g/l | |
| Monosodium glutamate | | 4.8 g/l | |
| Sodium citrate | | 0.95 g/l | |
| $FeSO_4 \times 7H_2O$ | | 9.5 mg/l | |
| $MnCl_2 \times 4H_2O$ | | 1.9 mg/l | |
| $ZnSO_4 \times 7H_2O$ | | 1.4 mg/l | |
| $CoCl_2 \times 6H_2O$ | | 1.9 mg/l | |
| $CuSO_4 \times 5H_2O$ | | 0.2 mg/l | |
| $Na_2MoO_4 \times 2H_2O$ | | 0.7 mg/l | |
| $K_2HPO_4 \times 3H_2O$ | | 15.2 g/l | |
| $KH_2PO_4$ | | 3.9 g/l | |
| $MgCl_2 \times 6H_2O$ | | 0.9 g/l | |
| $CaCl_2 \times 2H_2O$ | | 0.09 g/l | |
| MOPS | | 59.8 g/l | |
| pH* | | 7.2 | |

*to be adjusted with dilute aqueous NaOH solution
**glucose concentration in the hydrolyzate
***amount of hydrolyzate weighed in per liter of medium After the inoculation, the flasks were incubated in a humidified shaker for 24 hours at 43° C., with shaking (250 rpm). After the fermentation was terminated, the glucose and pantothenic acid contents were determined by HPLC. The glucose was determined with the aid of an Aminex HPX-87H column from Bio-Rad. The pantothenic acid concentration was determined by means of separation on an Aqua C18-column from Phenomenex. The results are compiled in Table 12.

TABLE 12

| Flask No. | Glucose [g/l] | Pantothenic acid [g/l] |
|---|---|---|
| 1 | 0.00 | 1.75 |
| 2 | 0.00 | 1.70 |
| 3 | 0.00 | 1.73 |
| 4 | 0.10 | 1.80 |
| 5 | 0.10 | 1.90 |
| 6 | 0.19 | 1.96 |
| 7 | 0.12 | 2.01 |
| 8 | 0.12 | 2.12 |
| 9 | 0.13 | 1.80 |

In all flasks, pantothenic acid was produced in comparable amounts in the order of approximately 1.5 to 2 g/l, corresponding to the yield obtained in a standard fermentation with a glucose nutrient solution.

The product can be worked up for example as described in WO 02/24001, WO 02/072857 and WO 05/028659.

Example 5

A corn meal hydrolyzate obtained as described in Example II. 3a was employed in shake-flask experiments using *Aspergillus niger* (flasks 1-3). In addition, a rye meal hydrolyzate (flasks 7-9) and wheat meal hydrolyzate (flasks 4-6) prepared analogously to Example II. 3 were employed in parallel.

5.1) Strains

*Aspergillus niger* phytase production strain with 6 copies of the *Aspergillus ficuum* phyA gene under the control of the glaA promoter was prepared analogously to the preparation of NP505-7, which is described in detail in WO 98/46772. A strain with 3 modified glaA amplicons (analogous to ISO505), but without integrated phyA expression cassettes, was used as the control.

5.2) Preparation of the Inoculum 20 ml of the preculture medium (see Table 13) in 100 ml Erlenmeyer flasks equipped with one baffle are inoculated in each case with 100 μl of a frozen culture and incubated in a humidified shaker for 24 hours at 34° C., with shaking (170 rpm).

TABLE 13

| Composition of the preculture medium | |
|---|---|
| Constituent | Concentration |
| Glucose | 30.0 g/l |
| Peptone from casein | 10.0 g/l |
| Yeast extract | 5.0 g/l |
| $KH_2PO_4$ | 1.0 g/l |
| $MgSO_4 \times 7H_2O$ | 0.5 g/l |
| $ZnCl_2$ | 30 mg/l |
| $CaCl_2$ | 20 mg/l |
| $MnSO_4 \times 1H_2O$ | 9 mg/l |
| $FeSO_4 \times 7H_2O$ | 3 mg/l |
| Tween 80 | 3.0 g/l |
| Penicillin | 50 000 IU/l |
| Streptomycin | 50 mg/l |
| pH* | 5.5 |

*to be adjusted with dilute sulfuric acid 50 ml of the main culture medium (see Table 14) in 250 ml Erlenmeyer flasks, equipped with one baffle, are inoculated with in each case 5 ml of preculture.

5.3) Preparation of the Fermentation Liquor

The compositions of the flask media 1 to 9 are shown in Table 14. A suitable amount of glucose solution was used in the control medium in place of meal hydrolyzate.

TABLE 14

Flask media

| | | Flask No. | |
|---|---|---|---|
| | 1-3 | 4-6 | 7-9 |
| Corn 381.4 g/kg** | 184 g/l*** | | |
| Wheat 342.0 g/kg** | | 205 g/l*** | |
| Rye 303.0 g/kg** | | | 231 g/l*** |
| Peptone from casein | 25.0 g/l | | |
| Yeast extract | 12.5 g/l | | |
| $KH_2PO_4$ | 1.0 g/l | | |
| $K_2SO_4$ | 2.0 g/l | | |
| $MgSO_4 \times 7H_2O$ | 0.5 g/l | | |
| $ZnCl_2$ | 30 mg/l | | |
| $CaCl_2$ | 20 mg/l | | |
| $MnSO_4 \times 1H_2O$ | 9 mg/l | | |
| $FeSO_4 \times 7H_2O$ | 3 mg/l | | |
| Penicillin | 50 000 IU/l | | |
| Streptomycin | 50 mg/l | | |
| pH* | 5.6 | | |

*to be adjusted with dilute sulfuric acid
**glucose concentration in the hydrolyzate
***amount of hydrolyzate weighed in per liter of medium After the inoculation, the flasks were incubated in a humidified shaker for 6 days at 34° C., with shaking (170 rpm). After the fermentation was terminated, the phytase activity was determined with the aid of an assay. After the fermentation was terminated, the phytase activity was determined with phytic acid as substrate and at a suitable phytase activity level (standard: 0.6 U/ml) in 250 mM acetic acid/sodium acetate/Tween 20 (0.1% by weight), pH 5.5 buffer. The assay was standardized for use in microtiter plates (MTPs). 10 µl of the enzyme solution were mixed with 140 µl of 6.49 mM phytate solution in 250 mM sodium acetate buffer, pH 5.5 (phytate: phytic acid dodecasodium salt. After incubation for one hour at 37° C., the reaction was stopped by addition of an equal volume (150 µl) of trichloroacetic acid. An aliquot of this mixture (20 µl) was transferred into 280 µl of a solution comprising 0.32N $H_2SO_4$, 0.27% by weight of ammonium molybdate and 1.08% by weight of ascorbic acid. This was followed by incubation for 25 minutes at 50° C. The absorption of the blue solution was measured at 820 nm. The results are compiled in Table 15.

TABLE 15

| | Phytase activity [FTU/ml]* |
|---|---|
| Corn | 433 |
| Wheat | 476 |
| Rye | 564 |
| Control | 393 |

*FTU = formazine turbidity unit

The product can be worked up as described in WO 98/55599.

Example 6

A corn meal hydrolyzate obtained as described in Example II. 3a was employed in shake-flask experiments using *Ashbya gossypii* (flasks 1-4). In addition, a rye meal hydrolyzate (flasks 9-12) and wheat meal hydrolyzate (flasks 5-8) prepared analogously to Example II. 3 were employed in parallel.

6.1) Strain

The riboflavin-producing strain employed is *Ashbya gossypii* ATCC 10895 (see also Schmidt G. et al. Inhibition of purified isocitrate lyase identified itaconate and oxalate as potential antimetabolites for the riboflavin overproducer *Ashbya gossypii*. Microbiology 142: 411-417, 1996).

6.2) Preparation of the Inoculum

The cells are streaked onto sterile HMG agar (composition: see Table 16; 20 minutes at 121° C.) and then incubated for 72 hours at 28° C.

TABLE 16

Composition of the HMG agar plates

| Constituent | Concentration |
|---|---|
| D-glucose | 4.0 g/l |
| Yeast extract | 4.0 g/l |
| Malt extract | 10.0 g/l |
| Agar | 30.0 g/l |
| pH | 7.2 |

Thereafter, 50 ml of the preculture medium (see Table 17) in 250 ml Erlenmeyer flasks, equipped with two baffles, are inoculated with in each case one loop-full of cells and incubated in a humidified shaker for 24 hours at 28° C., with shaking (180 rpm).

TABLE 17

Composition of the preculture medium

| Constituent | Concentration |
|---|---|
| Bacto peptone | 10.0 g/l |
| Yeast extract | 1.0 g/l |
| Myo-inositol | 0.3 g/l |
| D-glucose | 10.0 g/l |
| pH* | 7.0 |

*to be adjusted with dilute aqueous NaOH solution 50 ml of the main culture medium (see Table 18) in 250 ml Erlenmeyer flasks, equipped with two baffles, are inoculated with in each case 5 ml of preculture.

6.3) Preparation of the Fermentation Liquor

The compositions of the flask media 1 to 12 are shown in Table 18. A suitable amount of glucose solution was used in the control medium in place of meal hydrolyzate.

TABLE 18

Flask media

| | | Flask No. | | |
|---|---|---|---|---|
| | | 1-4 | 5-8 | 9-12 |
| Corn 381.4 g/kg** | 26.2 g/l*** | | | |
| Wheat 342.0 g/kg** | | | 29.2 g/l*** | |
| Rye 303.0 g/kg** | | | | 33.0 g/l*** |
| Bacto peptone | 10.0 g/l | | | |
| Yeast extract | 1.0 g/l | | | |
| Myo-inositol | 0.3 g/l | | | |
| pH* | 7.0 | | | |

*to be adjusted with dilute aqueous NaOH solution
**glucose concentration in the hydrolyzate
***amount of hydrolyzate weighed in per liter of medium After the inoculation, the flasks were incubated in a humidified shaker for 6 days at 28° C., with shaking (180 rpm). After the fermentation was terminated, the vitamin $B_2$ content was determined by means of HPLC. The results are compiled in Table 19.

TABLE 19

| | Vitamin $B_2$ |
|---|---|
| Corn | 2.73 g/l |
| Wheat | 2.15 g/l |
| Rye | 2.71 g/l |
| Control | 0.12 g/l |

The product can be worked up as described in EP 00345717.

Example 7

A corn meal hydrolyzate obtained as described in Example II. 3a was employed in shake-flask experiments using *Corynebacterium glutamicum* (flasks 1-3). In addition, a rye meal hydrolyzate (flasks 7-9) and wheat meal hydrolyzate (flasks 4-6) prepared analogously to Example II. 3 were employed in parallel.

7.1) Strains

The skilled worker knows *Corynebacterium* strains which produce methionine. The preparation of such strains is described for example in Kumar D. Gomes J. Biotechnology Advances, 23(1):41-61, 2005; Kumar D. et al. Process Biochemistry, 38:1165-1171, 2003; WO 04/024933 and WO 02/18613.

7.2) Preparation of the Inoculum

After streaking onto sterile CM+Kan agar (composition: see Table 20; 20 minutes at 121° C.), the cells are incubated for 24 hours at 30° C. The cells are subsequently scraped from the plates and resuspended in saline. 35 ml of the medium (see Table 5) in 250 ml Erlenmeyer flasks, equipped with two baffles, are in each case inoculated with such an amount of the cell suspension thus prepared that the optical density reaches an $OD_{610}$ value of 0.5 at 610 nm.

TABLE 20

| Composition of the CM + Kan agar plates | |
|---|---|
| Concentration | Constituent |
| 10.0 g/l | D-glucose |
| 2.5 g/l | NaCl |
| 2.0 g/l | Urea |
| 10.0 g/l | Bacto peptone (Difco) |
| 5.0 g/l | Yeast extract (Difco) |
| 5.0 g/l | Beef extract (Difco) |
| 20 µg/ml | Kanamycin |
| 25.0 g/l | Agar |

7.3) Preparation of the Fermentation Liquor

The compositions of the flask media 1 to 9 are shown in Table 21. A suitable amount of glucose solution was used in the control medium in place of meal hydrolyzate.

TABLE 21

| Flask media | | | |
|---|---|---|---|
| | Flask No. | | |
| | 1-3 | 4-6 | 7-9 |
| Corn 381.4 g/kg** | 157.2 g/l*** | | |
| Wheat 342.0 g/kg** | | 175.6 g/l*** | |
| Rye 303.0 g/kg** | | | 198.0 g/l*** |
| $(NH_4)_2SO_4$ | | 20 g/l | |
| Urea | | 5 g/l | |
| $KH_2PO_4$ | | 0.113 g/l | |
| $K_2HPO_4$ | | 0.138 g/l | |

TABLE 21-continued

| Flask media | | | |
|---|---|---|---|
| | Flask No. | | |
| | 1-3 | 4-6 | 7-9 |
| ACES | | 52 g/l | |
| MOPS | | 21 g/l | |
| Citric acid × $H_2O$ | | 0.49 g/l | |
| 3,4-Dihydroxybenzoic acid | | 3.08 mg/l | |
| NaCl | | 2.5 g/l | |
| KCl | | 1 g/l | |
| $MgSO_4 \times 7H_2O$ | | 0.3 g/l | |
| $FeSO_4 \times 7H_2O$ | | 25 mg/l | |
| $MnSO_4 \times 4\text{-}6H_2O$ | | 5 mg/l | |
| $ZnCl_2$ | | 10 mg/l | |
| $CaCl_2$ | | 20 mg/l | |
| $H_3BO_3$ | | 150 µg/l | |
| $CoCl \times 6H_2O$ | | 100 µg/l | |
| $CuCl_2 \times 2H_2O$ | | 100 µg/l | |
| $NiSO_4 \times 6H_2O$ | | 100 µg/l | |
| $Na_2MoO_4 \times 2H_2O$ | | 25 µg/l | |
| Biotin (vit. H) | | 1050 µg/l | |
| Thiamine × HCl (vit. $B_1$) | | 2100 µg/l | |
| Nicotinamide | | 2.5 mg/l | |
| Pantothenic acid | | 125 mg/l | |
| Cyanocobalamine (vit. $B_{12}$) | | 1 µg/l | |
| 4-Aminobenzoic acid (PABA; vit. $H_1$) | | 600 µg/l | |
| Folic acid | | 1.1 µg/l | |
| Pyridoxine (vit. $B_6$) | | 30 µg/l | |
| Riboflavin (vit. $B_2$) | | 90 µg/l | |
| CSL | | 40 ml/l | |
| Kanamycin | | 25 µg/ml | |
| pH* | | 6.85 | |

*to be adjusted with dilute aqueous NaOH solution
**glucose concentration in the hydrolyzate
***amount of hydrolyzate weighed in per liter of medium After the inoculation, the flasks were incubated in a humidified shaker at 30° C. and with shaking (200 rpm) until the glucose had been consumed. After the fermentation was terminated, the methionine content was determined by means of HPLC (column: Agilent ZORBAX Eclipse AAA; Method It. Eclipse AAA protocol, Technical Note 5980-1193). The results are compiled in Table 22.

TABLE 22

| Flask | | Methionine [µmol/l] |
|---|---|---|
| Corn | 1 | 9643.1 |
| | 2 | 9509.2 |
| | 3 | 9395.3 |
| Wheat | 4 | 6839.9 |
| | 5 | 7133.9 |
| | 6 | 7028.9 |
| Rye | 7 | 7894.7 |
| | 8 | 7526.5 |
| | 9 | 6998.9 |
| Control | 10 | 1920.8 |
| | 11 | 1916.3 |

The product can be worked up for example as described in WO 05/007862 and the earlier application DE 10359668.2.

Example 8

A corn meal hydrolyzate obtained as described in Example II. 3a was employed in shake-flask experiments using Bacterium 130Z.

8.1) Strain

Bacterium 130Z (ATCC No. 55618) was employed as the succinate-producing strain.

8.2) Preparation of the Fermentation Liquor 50 ml of the main culture medium (see Table 23) in 120 ml serum flasks are inoculated with in each case 1 ml of a frozen culture. Before the serum flasks are sealed, $CO_2$ is injected (0.7 bar).

The composition of the medium is listed in Table 23 (cf. U.S. Pat. No. 5,504,004). Instead of meal hydrolyzate, a corresponding amount of glucose solution was used in the control medium (final glucose concentration: 100 g/l).

TABLE 23

| Medium* | |
|---|---|
| Constituent | Concentration |
| Corn 381.4 g/kg** | 262 g/l*** |
| NaCl | 0.1 g/l |
| $K_2HPO_4$ | 0.3 g/l |
| $MgCl_2 \times 6H_2O$ | 20 mg/l |
| $CaCl_2 \times H_2O$ | 20 mg/l |
| $(NH_4)_2SO_4$ | 0.1 g/l |
| Biotin | 200 µg/l |
| CSL | 15.0 g/l |
| 10% Yeast extract | 15.0 g/l |
| $MgCO_3$ | 80.0 mg/l |

*under $CO_2/N_2$ atmosphere, also while filling the flasks
**glucose concentration in the hydrolyzate
***amount of hydrolyzate weighed in per liter of medium After inoculation, the serum flasks were incubated in a shaker for 46 hours at 37° C., with shaking (160 rpm). After the fermentation was terminated, the glucose and succinate contents were determined by means of HPLC. The determination was carried out with the aid of an Aminex HPX-87H column from Bio-Rad. The results are compiled in Table 24.

TABLE 24

| No. | Glucose [g/l] | Succinate [g/l] |
|---|---|---|
| 1 | 30.93 | 42.501 |
| 2 | 29.273 | 44.114 |
| Control | 17.414 | 47.73 |

Example 9

A corn meal hydrolyzate obtained as described in Example II. 3a is employed in shake-flask experiments using *Escherichia coli* (flasks 1-3). In addition, a rye meal hydrolyzate (flasks 7-9) and wheat meal hydrolyzate (flasks 4-6) prepared analogously to Example II. 3 are employed in parallel.

9.1) Strain

*Escherichia coli* strains which produce L-threonine are known to the skilled worker. The preparation of such strains is described for example in EP 1013765, A1, EP 1016710 A2, U.S. Pat. No. 5,538,873.

9.2) Preparation of the Inoculum

The cells are streaked onto sterile LB agar. Antibiotics are added to the LB agar if suitable resistance genes exist as markers in the strain in question. For example kanamycin (40 µg/ml) or ampicillin (100 mg/l) can be used for this purpose. The strains are incubated for 24 hours at 30° C. The cells are subsequently scraped from the plate and resuspended in saline. 25 ml of the medium (see Table 25) in 250 ml Erlenmeyer flasks, equipped with two baffles, are inoculated in each case with such an amount of the cell suspension thus prepared that the optical density reaches an $OD_{610}$ value of 0.5 at 610 nm.

9.3) Preparation of the Fermentation Liquor

The compositions of the flask media 1 to 9 are shown in Table 25. A suitable amount of glucose solution was used in the control medium in place of meal hydrolyzate.

TABLE 25

| Flask media | | | |
|---|---|---|---|
| | Flask No. | | |
| | 1-3 | 4-6 | 7-9 |
| Corn 381.4 g/kg** | 157.2 g/l*** | | |
| Wheat 342.0 g/kg** | | 175.6 g/l*** | |
| Rye 303.0 g/kg** | | | 198.0 g/l*** |
| $(NH_4)_2SO_4$ | 22 g/l | | |
| $K_2HPO_4$ | 2 g/l | | |
| NaCl | 0.8 g/l | | |
| $MgSO_4 \times 7H_2O$ | 0.8 g/l | | |
| $FeSO_4 \times 7H_2O$ | 20 mg/l | | |
| $MnSO_4 \times 5H_2O$ | 20 mg/l | | |
| Thiamine × HCl (vit. $B_1$) | 200 mg/l | | |
| Yeast extract | 1.0 g/l | | |
| $CaCO_3$ (sterilized separately) | 30 g/l | | |
| Kanamycin | 50 mg/l | | |
| Ampicillin | 100 mg/l | | |
| pH | 6.9 ± 0.2 | | |

*to be adjusted with dilute aqueous NaOH solution
**glucose concentration in the hydrolyzate
***amount of hydrolyzate weighed in per liter of medium After the inoculation, the flasks are incubated in a humidified shaker at 30° C. and with shaking (200 rpm) until the glucose has been consumed. After the fermentation was terminated, the L-threonine content can be determined by means of reversed-phase HPLC as described by Lindroth et al., Analytical Chemistry 51: 1167-1174, 1979.

Thereafter, the fermentation liquor can be harvested and the L-threonine present in the fermentation liquor can be isolated, purified or otherwise worked up, for example as described in U.S. Pat. No. 5,538,873 and by Okamoto et al., Bioscience, Biotechnology and Biochemistry 61 (11), 1877-1882, 1997.

Example 10

The further L-amino acids glutamate, lysine, histidine, proline and arginine are produced analogously to the procedure described in Example 9 by employing suitable strains. The strains in question are described for example in EP 1016710.

Example 11

A cassava meal hydrolyzate obtained analogously to Example II. 3 was employed in shake-flask experiments using the lysine-producing *Corynebacterium glutamicum* strain described in 11.2) (flasks 1-4). The meal employed had the following size distribution: 45%<100 µm, 56%<200 µm, 79%<630 µm.

Even at the beginning of the liquefaction step, the viscosity of the suspension was relatively high so that cassava meal was initially employed in an amount which corresponded to a dry matter content of 35% by weight. This was followed by a suitably increased addition of meal to reach a dry matter content of 55% by weight in the end. The viscosity of the suspension remained relatively high during the entire liquefaction and saccharification process. Moreover, the cassava meal had a tendency to agglomerate; during the course of the process, the agglomerates only dissolved to some extent. In the iodine-starch test, existing agglomerates were stained deep blue after a few minutes; this suggests that the agglomerated starch was not fully converted, despite repeated boiling up and prolonged waiting periods.

11.1) Strain

The modified wild type with feedback-deregulated aspartokinase ATCC13032 lysC$^{fbr}$ described under III. was used.

11.2) Preparation of the Inoculum

After streaking onto sterile CM+CaAc agar (composition: see Table 26; 20 minutes at 121° C.), the cells were incubated for 24 hours at 30° C. The cells were subsequently scraped from the plate and resuspended in saline. 23 ml of the medium (see Table 27) in 250 ml Erlenmeyer flasks, equipped with two baffles, were inoculated in each case with such an amount of the cell suspension thus prepared that the optical density reached an $OD_{610}$ value of 0.5 at 610 nm.

TABLE 26

Composition of the CM + CaAc agar plates

| Concentration | Constituent |
|---|---|
| 10.0 g/l | D-glucose |
| 2.5 g/l | NaCl |
| 2.0 g/l | Urea |
| 5.0 g/l | Bacto peptone (Difco) |
| 5.0 g/l | Yeast extract (Difco) |
| 5.0 g/l | Beef extract (Difco) |
| 20.0 g/l | Casamino acids |
| 20.0 g/l | Agar |

11.3) Preparation of the Fermentation Liquor

The composition of the flask medium is shown in Table 27. A suitable amount of glucose solution was used in the control medium in place of meal hydrolyzate.

TABLE 27

Flask media

| | |
|---|---|
| Cassava 362 g/kg** | 164 g/l*** |
| (NH$_4$)$_2$SO$_4$ | 20 g/l |
| Urea | 5 g/l |
| KH$_2$PO$_4$ | 0.113 g/l |
| K$_2$HPO$_4$ | 0.138 g/l |
| ACES | 52 g/l |
| MOPS | 21 g/l |
| Citric acid × H$_2$O | 0.49 g/l |
| 3,4-Dihydroxybenzoic acid | 3.08 mg/l |
| NaCl | 2.5 g/l |
| KCl | 1 g/l |
| MgSO$_4$ × 7H$_2$O | 0.3 g/l |
| FeSO$_4$ × 7H$_2$O | 25 mg/l |
| MnSO$_4$ × 4-6H$_2$O | 5 mg/l |
| ZnCl$_2$ | 10 mg/l |
| CaCl$_2$ | 20 mg/l |
| H$_3$BO$_3$ | 150 µg/l |
| CoCl × 6H$_2$O | 100 µg/l |
| CuCl$_2$ × 2H$_2$O | 100 µg/l |
| NiSO$_4$ × 6H$_2$O | 100 µg/l |
| Na$_2$MoO$_4$ × 2H$_2$O | 25 µg/l |
| Biotin (vit. H) | 1050 µg/l |
| Thiamine × HCl (vit. B$_1$) | 2100 µg/l |
| Nicotinamide | 2.5 mg/l |
| Pantothenic acid | 125 mg/l |
| Cyanocobalamine (vit. B$_{12}$) | 1 µg/l |
| 4-Aminobenzoic acid (PABA; vit. H$_1$) | 600 µg/l |
| Folic acid | 1.1 µg/l |
| Pyridoxine (vit. B$_6$) | 30 µg/l |
| Riboflavin (vit. B$_2$) | 90 µg/l |
| CSL | 40 ml/l |
| pH* | 6.85 |

*to be adjusted with dilute aqueous NaOH solution
**glucose concentration in the hydrolyzate
***amount of hydrolyzate weighed in per liter of medium After the inoculation, the flasks were incubated in a humidified shaker for 48 hours at 30° C., with shaking (200 rpm). After the fermentation was terminated, the glucose and lysine contents were determined by HPLC. The HPLC analyses were carried out with an Agilent 1100 series LC system. The glucose was determined with the aid of an Aminex HPX-87H column from Bio-Rad. The amino acid concentration was determined by means of high-pressure liquid chromatography on an Agilent 1100 series LC system HPLC. Pre-column derivatization with orthophthaldehyde permits the quantification of the amino acids formed; the amino acid mixture is separated off a Hypersil AA column (Agilent). The results are compiled in Table 28.

TABLE 28

| Flask No. | Glucose [g/l] | Lysine [g/l] |
|---|---|---|
| 1 | 0.0 | 12.87 |
| 2 | 0.0 | 14.00 |
| 3 | 0.1 | 12.44 |
| Control | 0.1 | 10.15 |

In all flasks, lysine was produced in comparable amounts in the order of approximately 10 to 14 g/l, corresponding to the yield obtained in a standard fermentation with glucose nutrient solution.

Example 12

A partially saccharified corn meal hydrolyzate was employed in shake-flask experiments using *Aspergillus niger*.

12.1) Liquefaction and (Partial) Saccharification

The liquefaction was carried out analogously to Example II. 3a. After the suspension had cooled to 61° C. and the pH adjusted to 4.3, 5.38 ml (=1.5% by weight of enzyme/dry matter) Dextrozyme GA (Novozymes A/S) were added. Every 10, 15, 20, 30, 45 and 60 minutes after the addition of the enzyme, a 50 g sample was taken and suspended in 25 ml of sterile, ice-cooled fully demineralized water. The samples were placed into an ice-bath and immediately employed in the flask test. No inactivation of the enzyme took place.

12.2) Fermentation

The strain used in Example 5.1) was employed. The inoculum was prepared as described in Example 5.2).

The compositions of the flask medium which were listed in Table 29 were used for preparing the fermentation liquor. Each sample was used for two flasks.

TABLE 29

Flask media

| | |
|---|---|
| Corn | 10 g/l*** |
| Peptone from casein | 25.0 g/l |
| Yeast extract | 12.5 g/l |
| KH$_2$PO$_4$ | 1.0 g/l |
| K$_2$SO$_4$ | 2.0 g/l |
| MgSO$_4$ × 7H$_2$O | 0.5 g/l |
| ZnCl$_2$ | 30 mg/l |
| CaCl$_2$ | 20 mg/l |
| MnSO$_4$ × 1H$_2$O | 9 mg/l |
| FeSO$_4$ × 7H$_2$O | 3 mg/l |

TABLE 29-continued

| Flask media | |
|---|---|
| Penicillin | 50 000 IU/l |
| Streptomycin | 50 mg/l |
| pH* | 5.6 |

*to be adjusted with dilute sulfuric acid
***partially saccharified hydrolyzate weighed in per liter of medium After inoculation, the flasks were incubated in a humidified shaker for 6 days at 34° C., with shaking (170 rpm). After the fermentation was terminated, the phytase activity was determined with the aid of an assay (as described in Example 5.3). The results are compiled in Table 30.

TABLE 30

| Termination of the standard saccharification after x minutes | Flask | Phytase activity [FTU/ml] |
|---|---|---|
| 10 | 1 | 425 |
|  | 2 | 387 |
| 15 | 3 | 312 |
|  | 4 | 369 |
| 20 | 5 | 366 |
|  | 6 | 316 |
| 30 | 7 | 343 |
|  | 8 | 454 |
| 45 | 9 | 372 |
|  | 10 | 358 |
| 60 | 11 | 298 |
|  | 12 | 283 |

Example 13

A partially saccharified corn meal hydrolyzate was employed in shake-flask experiments using *Corynebacterium glutamicum*.

13.1) Liquefaction and (Partial) Saccharification

The liquefaction was carried out analogously to Example II. 3a. After the suspension had cooled to 61° C. and the pH adjusted to 4.3, 5.38 ml (=1.5% by weight of enzyme/dry matter) Dextrozyme GA (Novozymes A/S) were added. Every 10, 15, 20, 30, 45 and 60 minutes after the addition of the enzyme, a 50 g sample was taken and suspended in 25 ml of sterile, ice-cooled fully demineralized water. The samples were placed into an ice-bath and immediately employed in the flask test. No inactivation of the enzyme took place.

13.2) Fermentation

The strain used in Example 3) was employed. The inoculum was prepared as described in Example 3.1).

The compositions of the flask medium which are listed in Table 31 were used for preparing the fermentation liquor. Each sample was used for three flasks.

TABLE 31

| Flask media | |
|---|---|
| Corn | 4.5 g/l*** |
| $(NH_4)_2SO_4$ | 20 g/l |
| Urea | 5 g/l |
| $KH_2PO_4$ | 0.113 g/l |
| $K_2HPO_4$ | 0.138 g/l |
| ACES | 52 g/l |
| MOPS | 21 g/l |
| Citric acid × $H_2O$ | 0.49 g/l |
| 3,4-Dihydroxybenzoic acid | 3.08 mg/l |
| NaCl | 2.5 g/l |
| KCl | 1 g/l |
| $MgSO_4 \times 7H_2O$ | 0.3 g/l |

TABLE 31-continued

| Flask media | |
|---|---|
| $FeSO_4 \times 7H_2O$ | 25 mg/l |
| $MnSO_4 \times 4\text{-}6H_2O$ | 5 mg/l |
| $ZnCl_2$ | 10 mg/l |
| $CaCl_2$ | 20 mg/l |
| $H_3BO_3$ | 150 µg/l |
| $CoCl \times 6H_2O$ | 100 µg/l |
| $CuCl_2 \times 2H_2O$ | 100 µg/l |
| $NiSO_4 \times 6H_2O$ | 100 µg/l |
| $Na_2MoO_4 \times 2H_2O$ | 25 µg/l |
| Biotin (vit. H) | 1050 µg/l |
| Thiamine × HCl (vit. $B_1$) | 2100 µg/l |
| Nicotinamide | 2.5 mg/l |
| Pantothenic acid | 125 mg/l |
| Cyanocobalamine (vit. $B_{12}$) | 1 µg/l |
| 4-Aminobenzoic acid (PABA; vit. $H_1$) | 600 µg/l |
| Folic acid | 1.1 µg/l |
| Pyridoxine (vit. $B_6$) | 30 µg/l |
| Riboflavin (vit. $B_2$) | 90 µg/l |
| CSL | 40 ml/l |
| pH* | 6.85 |

*to be adjusted with dilute aqueous NaOH solution
***amount of hydrolyzate weighed in per liter of medium After the inoculation, the flasks were incubated in a humidified shaker for 48 hours at 30° C., with shaking (200 rpm). After the fermentation was terminated, the glucose and lysine contents were determined by HPLC. The HPLC analyses were carried out with an Agilent 1100 series LC system. The glucose was determined with the aid of an Aminex HPX-87H column from Bio-Rad. The amino acid concentration was determined by means of high-pressure liquid chromatography on an Agilent 1100 series LC system HPLC. Precolumn derivatization with orthophthaldehyde permits the quantification of the amino acids formed; the amino acid mixture is separated off a Hypersil AA column (Agilent). The results are compiled in Table 32.

TABLE 32

| Termination of the standard saccharification after x minutes | Flask | Lysine [g/l] |
|---|---|---|
| 10 | 1 | 15.05 |
|  | 2 | 11.71 |
|  | 3 | 14.24 |
| 15 | 4 | 14.91 |
|  | 5 | 15.27 |
|  | 6 | 12.20 |
| 20 | 7 | 13.19 |
|  | 8 | 13.65 |
|  | 9 | 11.14 |
| 30 | 10 | 15.38 |
|  | 11 | 12.45 |
|  | 12 | 11.56 |
| 45 | 13 | 13.13 |
|  | 14 | 14.64 |
|  | 15 | 13.48 |
| 60 | 16 | 14.58 |
|  | 17 | 13.72 |
|  | 18 | 14.27 |

Example 14

In a fermentation for the production of lysine, carried out analogously to Example 3, a protein composition was obtained after depletion of the lysine from the fermentation liquor in accordance with step c) as dried fermentation residue. Table 33 identifies essential constituents of the composition and their amounts by weight and compares them with the traditional DDGS composition.

TABLE 33

Analytical results based on dry matter in % by weight**

|  | Protein composition | Tabulated value* | Ratio |
|---|---|---|---|
| Crude protein | 68.1 | 29.7 | 2.29 |
| Crude fat | 8.4 | 10.0 | 0.84 |
| Crude fiber | 1.5 | (8.8) | 0.17 |
| Crude ash | 7.9 | 5.2 | 1.52 |
| Acid detergent fiber (ADF) | 4.6 | 19.7 | 0.23 |
| Neutral detergent fiber (ADF) | 17.9 | 38.8 | 0.46 |
| Lysine | 3.72 | 0.67 | 5.55 |
| Methionine | 0.87 | 0.54 | 1.61 |
| Threonine | 1.93 | 1.02 | 1.89 |
| Tryptophan | 0.46 | 0.26 | 1.77 |
| Phosphorus | 0.54 | 0.83 | 0.65 |
| Calcium | <0.11 | 0.22 | — |

*for DDGS (distiller's dried grain with solubles, the secondary product from bioethanol production) in accordance with National Research Council (NRC), Nutrient Requirements for Dairy Cattle, Seventh Revised Edition, National Academy Press, 2001 (or Spiehs M. J., Whitney M. H. and Shurson G. C: Nutrient database for distiller's dried grains with solubles produced from new ethanol plants in Minnesota and South Dakota, Journal of Animal Science 80, 2002, 2639-2645)

**the parameters mentioned, and the analytical methods required, are known to the skilled worker.

We claim:

1. A process for the production of at least one microbial metabolite having at least 3 carbon atoms, or having at least 2 carbon atoms and at least 1 nitrogen atom by means of sugar-based microbial fermentation, comprising:
   a) the preparation of a sugar-containing liquid hydrolyzate with a monosaccharide content of more than 20% by weight from a starch feedstock, the sugar-containing liquid hydrolyzate also comprising at least 20% by weight of the total non-starchy solid constituents of the starch feedstock;
   b) the fermentation for the production of the at least one metabolite, which comprises culturing, by using the sugar-containing liquid hydrolyzate, a microorganism strain which produces the at least one metabolite, where a fermentation liquor is obtained which contains the at least one metabolite; and
   c) depletion or isolation of at least one metabolite from the fermentation liquor,
   where the sugar containing liquid hydrolyzate is obtained in step a) by:
   a1) milling the starch feedstock, Which is selected from cereal kernels, by dry-milling process; and
   a2) liquefying the millbase in an aqueous liquid in the presence of at least one starch-liquefying enzyme, followed by saccharification using at least one saccharifying enzyme, to obtain a sugar-containing liquid hydrolyzate having a monosaccharide content of more than 20% by weight and also comprising at least 20% by weight of the total non-starchy solid constituents of the starch,
   where at least 40% of the millbase is added continuously or batchwise to the aqueous liquid in the course of the liquefaction step where the liquefaction is carried out at least in part above the gelling temperature of the starch employed and where at least 25% by weight of the total amount of the millbase added during the liquefaction are added at a temperature above the gelling temperature of the starch present in the millbase; and where the at least one metabolite produced is selected from the group consisting of organic mono-, di- and tricarboxylic acids which optionally have hydroxyl groups attached to them and which have 3 to 10 carbon atoms, among proteinogenic and nonproteinogenic amino acids, purine bases, pyrimidine bases, nucleosides, nucleotides, lipids, saturated and unsaturated fatty acids, dials having 3 to 10 carbon atoms, higher-functionality alcohols having 3 or more hydroxyl groups, longer-chain alcohols having at least 4 carbon atoms, carbohydrates, aromatic compounds, vitamins, provitamins, cofactors, nutraceuticals, proteins, carotenoids, ketones having 3 to 10 carbon atoms, lactones, biopolymers, and cyclodextrins.

2. The process according to claim 1, wherein the at least one starch-liquefying enzyme is selected from α-amylases and the at least one saccharifying enzyme from glucoamylases.

3. The process according to claim 1, wherein the cereal is selected from corn, rye, tritical and wheat kernels.

4. The process according to claim 1, wherein the millbase obtained during milling in step a1) comprises at least 50% by weight of flour particles with a particle size of more than 100 μm.

5. The process according to claim 1, wherein the liquefaction and saccharifying of the millbase in step a2) is carried out in such a way that the viscosity of the reaction mixture during the gelling process in step a2) amounts to not more than 20 Pas.

6. The process according to claim 2, wherein, in step a2), some of the at least one α-amylase is added to the aqueous liquid during the liquefaction.

7. The process according to claim 1, wherein a sugar-containing liquid medium with a monosaccharide content of more than 40% by weight is obtained.

8. The process according to claim 1, wherein at least one phytase is added to the sugar-containing liquid before the fermentation step b).

9. The process according to claim 1, wherein the at least one metabolite produced is selected from non-volatile substances.

10. The process according to claim 1, wherein the at least one metabolite produced is selected from the group consisting of enzymes, amino acids, vitamins, disaccharides, aliphatic mono- and dicarboxylic acids having 3 to 10 carbon atoms, aliphatic hydroxycarboxylic acids having 3 to 10 carbon atoms, ketones having 3 to 0.10 carbon atoms, alkanols having 4 to 10 carbon atoms, alkanediols having 3 to 8 carbon atoms, and polyhydroxyalkanoates.

11. The process according to claim 1, wherein the microorganism is selected from natural or recombinant microorganisms which produce at least one of the following metabolites: enzymes, amino acids, vitamins, disaccharides, aliphatic mono- and dicarboxylic acids having 3 to 10 carbon atoms, aliphatic hydroxycarboxylic acids having 3 to 10 carbon atoms, ketones having 3 to 10 carbon atoms, alkanols having 4 to 10 carbon atoms, alkanediols having 3 to 8 carbon atoms, and polyhydroxyalkanoates.

12. The process according to claim 11, wherein the microorganism is selected from the genera *Corynebacterium, Bacillus, Ashbya, Escherichia, Aspergillus, Alcaligenes, Actinobacillus, Anaerohiospirillum, Lactobacillus, Propionibacterium* and *Clostridium*, in particular among strains of *Corynebacterium glutamicum, Bacillus subtilis, Ashbya gossypii, Escherichia coli, Aspergillus niger* or *Alcaligenes latus, Anaerohiospirillum succiniproducens, Actinohacillus succinogenes, Lactobacillus delbrückii, Lactobacillus leichmanni, Propionibacterium arabinosum, Propionibacterium schermanii, Propionibacterium freudenreichii, Clostridium propionicum*, and *Clostridium acetobutlicum*.

13. The process according to claim 1, wherein the depletion or isolation of the at least one metabolite from the fermentation liquor as described in step c) is carried out by means of ion-exchange chromatography.

14. The process according to claim 13, wherein the metabolite is bound selectively on the ion exchanger and, if appropriate, the ion exchanger is washed prior to elution of the product.

15. The process according to claim 13, wherein the solids-loaded fermentation liquor flows towards the ion exchanger against gravity.

16. The process according to claim 1, wherein
  (i) a portion of not more than 50% by weight is removed from the sugar-containing liquid hydrolyzate obtained in step a) which comprises the non-starchy solid constituents of the starch feedstock and a fermentation as described in b) is carried out with the remainder in order to produce a first metabolite (A); and
  (ii) all or some of the non-starchy solid constituents of the starch feedstock are separated from this portion and a fermentation as described in h) is carried out with this portion to produce a second metabolite (B), which is identical to or different from the metabolite (A).

17. The process according to claim 16, wherein the separation of the non-starchy solid constituents of (ii) is carried out in such a way that the solids content of the remainder of the sugar-containing liquid amounts to not more than 50% by weight.

18. The process according to claim 16, wherein the metabolite (B) is selected from the group consisting of phytase, riboflavin, pantothenic acid, and polyhydroxyalkanoates.

19. The process according to claim 1, wherein, after the depletion or isolation of the at least one metabolite in accordance with step c), the volatile constituents of the fermentation liquor are removed to at least some extent, giving a solid or semisolid protein composition.

20. A protein composition obtained by the process according to claim 19, consisting essentially of the following dry matter constituents:
  a) 1 to 90% by weight of biomass from the fermentation;
  b) 1 to 90% by weight of non-starchy constituents of the starch feedstock;
  c) 0.01 to 10% by weight of a microbial metabolite having at least 3 carbon atoms or at least 2 carbon atoms and at least one nitrogen atom;
  d) 0 to 90% by weight of customary formulation auxiliaries; and
  e) 0 to 40% by weight of unmetabolized further constituents of the fermentation liquor;
  where the components a) to e) add up to 100% by weight of dry matter;
  where the metabolite is selected from the group consisting of organic mono-, di- and tricarboxylic acids which optionally have hydroxyl groups attached to them and which have 3 to 10 carbon atoms, among proteinogenic and nonproteinogenic amino acids, purine bases, pyrimidine bases, nucleosides, nucleotides, lipids, saturated and unsaturated fatty acids, diols having 3 to 10 carbon atoms, higher-functionality alcohols having 3 or more hydroxyl groups, longer-chain alcohols having at least 4 carbon atoms, carbohydrates, aromatic compounds, vitamins, provitamins, cofactors, nutraceuticals, proteins, carotenoids, ketones having 3 to 10 carbon atoms, lactones, biopolymers, and cyclodextrins.

21. The protein composition according to claim 20 with a crude protein content in the range of from 40 to 90% by weight, based on the dry matter of the protein composition.

22. The protein composition according to claim 20 which features at least one essential amino acid from among lysine, methionine, threonine and tryptophan.

\* \* \* \* \*

SEQUENCE LISTING

```
<160> NUMBER OF SEQ ID NOS: 8

<210> SEQ ID NO 1
<211> LENGTH: 35
<212> TYPE: DNA
<213> ORGANISM: Artificial Sequence
<220> FEATURE:
<223> OTHER INFORMATION: PCR primer

<400> SEQUENCE: 1
gagagagaga cgcgtcccag tggctgagac gcatc                              35

<210> SEQ ID NO 2
<211> LENGTH: 34
<212> TYPE: DNA
<213> ORGANISM: Artificial Sequence
<220> FEATURE:
<223> OTHER INFORMATION: PCR primer

<400> SEQUENCE: 2
ctctctctgt cgacgaattc aatcttacgg cctg                               34

<210> SEQ ID NO 3
<211> LENGTH: 4327
<212> TYPE: DNA
<213> ORGANISM: Artificial Sequence
<220> FEATURE:
<223> OTHER INFORMATION: Plasmid pCIS

<400> SEQUENCE: 3
tcgagaggcc tgacgtcggg cccggtacca cgcgtcatat gactagttcg gacctaggga    60
tatcgtcgac atcgatgctc ttctgcgtta attaacaatt gggatcctct agacccggga   120
tttaaatgat ccgctagcgg gctgctaaag gaagcggaac acgtagaaag ccagtccgca   180
gaaacggtgc tgacccgga tgaatgtcag ctactgggct atctggacaa gggaaaacgc    240
aagcgcaaag agaaagcagg tagcttgcag tgggcttaca tggcgatagc tagactgggc   300
ggttttatgg acagcaagcg aaccggaatt gccagctggg gcgccctctg gtaaggttgg   360
gaagccctgc aaagtaaact ggatggcttt cttgccgcca aggatctgat ggcgcagggg   420
atcaagatct gatcaagaga caggatgagg atcgtttcgc atgattgaac aagatggatt   480
gcacgcaggt tctccggccg cttgggtgga gaggctattc ggctatgact gggcacaaca   540
gacaatcggc tgctctgatg ccgccgtgtt ccggctgtca gcgcaggggc gcccggttct   600
ttttgtcaag accgacctgt ccggtgccct gaatgaactg caggacgagg cagcgcggct   660
atcgtggctg gccacgacgg cgttccttgc gcagctgtg ctcgacgttg tcactgaagc   720
```

```
gggaagggac tggctgctat tgggcgaagt gccggggcag gatctcctgt catctcacct      780
tgctcctgcc gagaaagtat ccatcatggc tgatgcaatg cggcggctgc atacgcttga      840
tccggctacc tgcccattcg accaccaagc gaaacatcgc atcgagcgag cacgtactcg      900 gatgaagcc ggtcttgtcg atcaggatga tctggacgaa gagcatcagg ggctcgcgcc       960
agccgaactg ttcgccaggc tcaaggcgcg catgcccgac ggcgaggatc tcgtcgtgac     1020
ccatggcgat gcctgcttgc cgaatatcat ggtggaaaat ggccgctttt ctggattcat     1080
cgactgtggc cggctgggtg tggcggaccg ctatcaggac atagcgttgg ctacccgtga     1140
tattgctgaa gagcttggcg gcgaatgggc tgaccgcttc ctcgtgcttt acggtatcgc     1200
cgctcccgat tcgcagcgca tcgccttcta tcgccttctt gacgagttct tctgagcggg     1260
actctggggt tcgaaatgac cgaccaagcg acgcccaacc tgccatcacg agatttcgat     1320
tccaccgccg ccttctatga aaggttgggc ttcggaatcg ttttccggga cgccggctgg     1380
atgatcctcc agcgcgggga tctcatgctg agttcttcg cccacgctag cggcgcgccg      1440
gccggcccgg tgtgaaatac cgcacagatg cgtaaggaga aaataccgca tcaggcgctc     1500
ttccgcttcc tcgctcactg actcgctgcg ctcggtcgtt cggctgcggc gagcggtatc     1560
agctcactca aaggcggtaa tacggttatc cacagaatca ggggataacg caggaaagaa     1620
catgtgagca aaaggccagc aaaaggccag gaaccgtaaa aaggccgcgt tgctggcgtt     1680
tttccatagg ctccgccccc ctgacgagca tcacaaaaat cgacgctcaa gtcagaggtg     1740
gcgaaacccg acaggactat aaagatacca ggcgtttccc cctggaagct ccctcgtgcg     1800
ctctcctgtt ccgaccctgc cgcttaccgg atacctgtcc gcctttctcc cttcgggaag     1860
cgtggcgctt tctcatagct cacgctgtag gtatctcagt tcggtgtagg tcgttcgctc     1920
caagctgggc tgtgtgcacg aacccccgt tcagcccgac cgctgcgcct tatccggtaa      1980
ctatcgtctt gagtccaacc cggtaagaca cgacttatcg ccactggcag cagccactgg     2040
taacaggatt agcagagcga ggtatgtagg cggtgctaca gagttcttga agtggtggcc     2100
taactacggc tacactagaa ggacagtatt tggtatctgc gctctgctga gccagttac      2160 cttcggaaaa agagttggta gctcttgatc cggcaaacaa accaccgctg gtagcggtgg     2220
tttttttgtt tgcaagcagc agattacgcg cagaaaaaaa ggatctcaag aagatccttt     2280
gatcttttct acggggtctg acgctcagtg gaacgaaaac tcacgttaag ggattttggt     2340
catgagatta tcaaaaagga tcttcaccta gatccttta aaggccggcc gcggccgcca     2400
tcggcatttt cttttgcgtt tttatttgtt aactgttaat tgtccttgtt caaggatgct     2460
gtctttgaca acagatgttt tcttgccttt gatgttcagc aggaagctcg gcgcaaacgt     2520
tgattgtttg tctgcgtaga atcctctgtt tgtcatatag cttgtaatca cgacattgtt     2580
tcctttcgct tgaggtacag cgaagtgtga gtaagtaaag gttacatcgt taggatcaag     2640 atccatttt aacacaaggc cagttttgtt cagcggcttg tatgggccag ttaaagaatt      2700
agaaacataa ccaagcatgt aaatatcgtt agacgtaatg ccgtcaatcg tcattttga      2760 tccgcgggag tcagtgaaca ggtaccattt gccgttcatt ttaaagacgt tcgcgcgttc     2820
aatttcatct gttactgtgt tagatgcaat cagcggtttc atcactttt tcagtgtgta      2880 atcatcgttt agctcaatca taccgagagc gccgtttgct aactcagccg tgcgtttttt     2940
atcgctttgc agaagttttt gactttcttg acggaagaat gatgtgcttt gccatagta      3000 tgctttgtta aataaagatt cttcgccttg gtagccatct tcagttccag tgtttgcttc     3060
```

```
aaatactaag tatttgtggc ctttatcttc tacgtagtga ggatctctca gcgtatggtt    3120
gtcgcctgag ctgtagttgc cttcatcgat gaactgctgt acattttgat acgttttttcc   3180 gtcaccgtca aagattgatt tataatcctc tacaccgttg atgttcaaag agctgtctga    3240
tgctgatacg ttaacttgtg cagttgtcag tgtttgtttg ccgtaatgtt taccggagaa    3300
atcagtgtag aataaacgga ttttccgtc agatgtaaat gtggctgaac ctgaccattc     3360
ttgtgtttgg tcttttagga tagaatcatt tgcatcgaat ttgtcgctgt ctttaaagac    3420
gcggccagcg ttttccagc tgtcaataga agtttcgccg acttttttgat agaacatgta    3480 aatcgatgtg tcatccgcat ttttaggatc tccggctaat gcaaagacga tgtggtagcc    3540
gtgatagttt gcgacagtgc cgtcagcgtt ttgtaatggc cagctgtccc aaacgtccag    3600
gccttttgca gaagagatat ttttaattgt ggacgaatca aattcagaaa cttgatatt     3660 ttcattttt tgctgttcag ggatttgcag catatcatgg cgtgtaatat gggaaatgcc     3720
gtatgtttcc ttatatggct tttggttcgt ttctttcgca aacgcttgag ttgcgcctcc    3780
tgccagcagt gcggtagtaa aggttaatac tgttgcttgt tttgcaaact ttttgatgtt    3840
catcgttcat gtctcctttt ttatgtactg tgttagcggt ctgcttcttc cagccctcct    3900
gtttgaagat ggcaagttag ttacgcacaa taaaaaaaga cctaaaatat gtaaggggtg    3960
acgccaaagt atacactttg ccctttacac attttaggtc ttgcctgctt tatcagtaac    4020
aaacccgcgc gatttacttt tcgacctcat tctattagac tctcgtttgg attgcaactg    4080
gtctattttc ctcttttgtt tgatagaaaa tcataaaagg atttgcagac tacgggccta    4140
aagaactaaa aaatctatct gtttcttttc attctctgta ttttttatag tttctgttgc    4200
atgggcataa agttgccttt ttaatcacaa ttcagaaaat atcataatat ctcatttcac    4260
taaataatag tgaacggcag gtatatgtga tgggttaaaa aggatcggcg gccgctcgat    4320
ttaaatc                                                              4327

<210> SEQ ID NO 4
<211> LENGTH: 5860
<212> TYPE: DNA
<213> ORGANISM: Artificial Sequence
<220> FEATURE:
<223> OTHER INFORMATION: Plasmid pCIS lysC

<400> SEQUENCE: 4
cccggtacca cgcgtcccag tggctgagac gcatccgcta aagccccagg aaccctgtgc     60
agaaagaaaa cactcctctg ctaggtagaa cacagtttat aaaggtagag ttgagcgggt    120
aactgtcagc acgtagatcg aaaggtgcac aaaggtggcc ctggtcgtac agaaatatgg    180
cggttcctcg cttgagagtg cggaacgcat tagaaacgtc gctgaacgga tcgttgccac    240
caagaaggct ggaaatgatg tcgtggttgt ctgctccgca atgggagaca ccacggatga    300
acttctagaa cttgcagcgg cagtgaatcc cgttccgcca gctcgtgaaa tggatatgct    360
cctgactgct ggtgagcgta tttctaacgc tctcgtcgcc atggcgattg agtcccttgg    420
cgcagaagcc caatctttca cgggctctca ggctggtgtg ctcaccaccg agcgccacgg    480
aaacgcacgc attgttgatg tcactccagg tcgtgtgcgt gaagcactcg atgagggcaa    540
gatctgcatt gttgctggtt tccagggtgt taataaagaa acccgcgatg tcaccacgtt    600
gggtcgtggt ggttctgaca ccactgcagt tgcgttggca gctgctttga acgctgatgt    660
gtgtgagatt tactccggacg ttgacggtgt gtataccgct gacccgcgca tcgttcctaa    720
tgcacagaag ctggaaaagc tcagcttcga agaaatgctg gaacttgctg ctgttggctc    780
```

```
caagattttg gtgctgcgca gtgttgaata cgctcgtgca ttcaatgtgc cacttcgcgt      840
acgctcgtct tatagtaatg atcccggcac tttgattgcc ggctctatgg aggatattcc      900
tgtggaagaa gcagtcctta ccggtgtcgc aaccgacaag tccgaagcca agtaaccgt       960 tctgggtatt tccgataagc caggcgaggc tgcgaaggtt ttccgtgcgt tggctgatgc     1020
agaaatcaac attgacatgg ttctgcagaa cgtctcttct gtagaagacg gcaccaccga     1080
catcaccttc acctgccctc gttccgacgg ccgccgcgcg atggagatct tgaagaagct     1140
tcaggttcag ggcaactgga ccaatgtgct ttacgacgac caggtcggca agtctccct      1200 cgtgggtgct ggcatgaagt ctcacccagg tgttaccgca gagttcatgg aagctctgcg     1260
cgatgtcaac gtgaacatcg aattgatttc cacctctgag attcgtattt ccgtgctgat     1320
ccgtgaagat gatctggatg ctgctgcacg tgcattgcat gagcagttcc agctgggcgg     1380
cgaagacgaa gccgtcgttt atgcaggcac cggacgctaa agttttaaag gagtagtttt     1440
acaatgacca ccatcgcagt tgttggtgca accggccagg tcggccaggt tatgcgcacc     1500
cttttggaag agcgcaattt cccagctgac actgttcgtt tctttgcttc cccacgttcc     1560
gcaggccgta agattgaatt cgtcgacatc gatgctcttc tgcgttaatt aacaattggg     1620
atcctctaga cccgggattt aaatcgctag cgggctgcta aaggaagcgg aacacgtaga     1680
aagccagtcc gcagaaacgg tgctgacccc ggatgaatgt cagctactgg gctatctgga     1740
caagggaaaa cgcaagcgca aagagaaagc aggtagcttg cagtgggctt acatggcgat     1800
agctagactg ggcggttta tggacagcaa gcgaaccgga attgccagct ggggcgccct      1860
ctggtaaggt tgggaagccc tgcaaagtaa actggatggc tttcttgccg ccaaggatct     1920
gatggcgcag gggatcaaga tctgatcaag agacaggatg aggatcgttt cgcatgattg     1980
aacaagatgg attgcacgca ggttctccgg ccgcttgggt ggagaggcta ttcggctatg     2040
actgggcaca acagacaatc ggctgctctg atgccgccgt gttccggctg tcagcgcagg     2100
ggcgcccggt tcttttgtc aagaccgacc tgtccggtgc cctgaatgaa ctgcaggacg     2160
aggcagcgcg gctatcgtgg ctggccacga cgggcgttcc ttgcgcagct gtgctcgacg     2220
ttgtcactga agcgggaagg gactggctgc tattgggcga agtgccgggg caggatctcc     2280
tgtcatctca ccttgctcct gccgagaaag tatccatcat ggctgatgca atgcggcggc     2340
tgcatacgct tgatccggct acctgcccat tcgaccacca agcgaaacat cgcatcgagc     2400
gagcacgtac tcggatggaa gccggtcttg tcgatcagga tgatctggac gaagagcatc     2460
aggggctcgc gccagccgaa ctgttcgcca ggctcaaggc gcgcatgccc gacggcgagg     2520
atctcgtcgt gacccatggc gatgcctgct tgccgaatat catggtggaa aatggccgct     2580
tttctggatt catcgactgt ggccggctgg gtgtggcgga ccgctatcag gacatagcgt     2640
tggctacccg tgatattgct gaagagcttg gcggcgaatg ggctgaccgc ttcctcgtgc     2700
tttacggtat cgccgctccc gattcgcagc gcatcgcctt ctatcgcctt cttgacgagt     2760
tcttctgagc gggactctgg ggttcgaaat gaccgaccaa gcgacgccca acctgccatc     2820
acgagatttc gattccaccg ccgccttcta tgaaaggttg gcttcggaa tcgttttccg      2880 ggacgccggc tggatgatcc tccagcgcgg ggatctcatg ctggagttct cgcccacgc      2940 tagcggcgcg ccggccggcc cggtgtgaaa taccgcacag atgcgtaagg agaaaatacc     3000
gcatcaggcg ctcttccgct tcctcgctca ctgactcgct gcgctcggtc gttcggctgc     3060
ggcgagcggt atcagctcac tcaaaggcgg taatacggtt atccacagaa tcaggggata     3120
```

```
acgcaggaaa gaacatgtga gcaaaaggcc agcaaaaggc caggaaccgt aaaaaggccg    3180
cgttgctggc gttttttccat aggctccgcc cccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta aaggacagt atttggtatc tgcgctctgc    3660
tgaagccagt taccttcgga aaagagttg gtagctcttg atccggcaaa caaccaccg    3720 ctggtagcgg tggttttttt gtttgcaagc agcagattac gcgcagaaaa aaaggatctc    3780
aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900
gccgcggccg ccatcggcat tttcttttgc gttttatttt gttaactgtt aattgtcctt    3960
gttcaaggat gctgtctttg acaacagatg ttttcttgcc tttgatgttc agcaggaagc    4020
tcggcgcaaa cgttgattgt tgtctgcgt agaatcctct gttttgtcata tagcttgtaa    4080 tcacgacatt gtttcctttc gcttgaggta cagcgaagtg tgagtaagta aaggttacat    4140
cgttaggatc aagatccatt tttaacacaa ggccagtttt gttcagcggc ttgtatgggc    4200
cagttaaaga attagaaaca taaccaagca tgtaaatatc gttagacgta atgccgtcaa    4260
tcgtcatttt tgatccgcgg gagtcagtga acaggtacca tttgccgttc attttaaaga    4320
cgttcgcgcg ttcaatttca tctgttactg tgttagatgc aatcagcggt ttcatcactt    4380
ttttcagtgt gtaatcatcg tttagctcaa tcataccgag agcgccgttt gctaactcag    4440
ccgtgcgttt tttatcgctt tgcagaagtt tttgactttc ttgacggaag aatgatgtgc    4500
ttttgccata gtatgctttg ttaaataaag attcttcgcc ttggtagcca tcttcagttc    4560
cagtgtttgc ttcaaatact aagtatttgt ggcctttatc ttctacgtag tgaggatctc    4620
tcagcgtatg gttgtcgcct gagctgtagt tgccttcatc gatgaactgc tgtacatttt    4680
gatacgtttt tccgtcaccg tcaaagattg atttataatc ctctacaccg ttgatgttca    4740
aagagctgtc tgatgctgat acgttaactt gtgcagttgt cagtgtttgt ttgccgtaat    4800
gtttaccgga gaaatcagtg tagaataaac ggatttttcc gtcagatgta atgtggctg    4860 aacctgacca ttcttgtgtt tggtctttta ggatagaatc atttgcatcg aatttgtcgc    4920
tgtctttaaa gacgcggcca gcgttttttcc agctgtcaat agaagtttcg ccgacttttt    4980
gatagaacat gtaaatcgat gtgtcatccg cattttagg atctccggct aatgcaaaga    5040
cgatgtggta gccgtgatag tttgcgacag tgccgtcagc gttttgtaat ggccagctgt    5100
cccaaacgtc caggccttt gcagaagaga tatttttaat tgtggacgaa tcaaattcag    5160
aaacttgata ttttttcattt ttttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340 acttttgat gttcatcgtt catgtctcct tttttatgta ctgtgttagc ggtctgcttc    5400
ttccagccct cctgttgaa gatggcaagt tagttacgca caataaaaaa agacctaaaa    5460
tatgtaaggg gtgacgccaa agtatacact ttgccctta cacattttag gtcttgcctg    5520
```

```
ctttatcagt aacaaacccg cgcgatttac ttttcgacct cattctatta gactctcgtt    5580
tggattgcaa ctggtctatt ttcctctttt gtttgataga aaatcataaa aggatttgca    5640
gactacgggc ctaaagaact aaaaaatcta tctgtttctt ttcattctct gtatttttta    5700
tagtttctgt tgcatgggca taaagttgcc ttttttaatca caattcagaa aatatcataa    5760
tatctcattt cactaaataa tagtgaacgg caggtatatg tgatgggtta aaaaggatcg    5820
gcggccgctc gatttaaatc tcgagaggcc tgacgtcggg                          5860
```

```
<210> SEQ ID NO 5
<211> LENGTH: 38
<212> TYPE: DNA
<213> ORGANISM: Artificial Sequence
<220> FEATURE:
<223> OTHER INFORMATION: PCR primer

<400> SEQUENCE: 5
cggcaccacc gacatcatct tcacctgccc tcgttccg                            38

<210> SEQ ID NO 6
<211> LENGTH: 38
<212> TYPE: DNA
<213> ORGANISM: Artificial Sequence
<220> FEATURE:
<223> OTHER INFORMATION: PCR primer

<400> SEQUENCE: 6
cggaacgagg gcaggtgaag atgatgtcgg tggtgccg                            38

<210> SEQ ID NO 7
<211> LENGTH: 1266
<212> TYPE: DNA
<213> ORGANISM: Corynebacterium glutamicum

<400> SEQUENCE: 7
```

```
gtggccctgg tcgtacagaa atatggcggt tcctcgcttg agagtgcgga acgcattaga     60
aacgtcgctg aacggatcgt tgccaccaag aaggctggaa atgatgtcgt ggttgtctgc    120
tccgcaatgg gagacaccac ggatgaactt ctagaacttg cagcggcagt gaatcccgtt    180
ccgccagctc gtgaaatgga tatgctcctg actgctggtg agcgtatttc taacgctctc    240
gtcgccatgg ctattgagtc ccttggcgca gaagcccaat ctttcacggg ctctcaggct    300
ggtgtgctca ccaccgagcg ccacggaaac gcacgcattg ttgatgtcac tccaggtcgt    360
gtgcgtgaag cactcgatga gggcaagatc tgcattgttg ctggtttcca gggtgttaat    420
aaagaaaccc gcgatgtcac cacgttgggt cgtggtggtt ctgacaccac tgcagttgcg    480
ttggcagctc ttttgaacgc tgatgtgtgt gagatttact cggacgttga cggtgtgtat    540
accgctgacc cgcgcatcgt tcctaatgca cagaagctgg aaaagctcag cttcgaagaa    600
atgctggaac ttgctgctgt tggctccaag attttggtgc tgcgcagtgt tgaatacgct    660
cgtgcattca atgtgccact tcgcgtacgc tcgtcttata gtaatgatcc cggcactttg    720
attgccggct ctatggagga tattcctgtg gaagaagcag tccttaccgg tgtcgcaacc    780
gacaagtccg aagccaaagt aaccgttctg ggtatttccg ataagccagg cgaggctgcg    840
aaggttttcc gtcgcgttgg ctgatgcagaa atcaacattg acatggttct gcagaacgtc    900
tcttctgtag aagacggcac caccgacatc accttcacct gccctcgttc cgacggccgc    960
cgcgcgatgg agatcttgaa gaagcttcag gttcagggca actggaccaa tgtgctttac    1020
```

```
gacgaccagg tcggcaaagt ctccctcgtg ggtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctaa                                                               1266

<210> SEQ ID NO 8
<211> LENGTH: 5860
<212> TYPE: DNA
<213> ORGANISM: Artificial Sequence
<220> FEATURE:
<223> OTHER INFORMATION: Plasmid pCIS lysC thr311ile

<400> SEQUENCE: 8
cccggtacca cgcgtcccag tggctgagac gcatccgcta aagccccagg aaccctgtgc      60
agaaagaaaa cactcctctg gctaggtaga cacagtttat aaaggtagag ttgagcgggt     120
aactgtcagc acgtagatcg aaaggtgcac aaaggtggcc ctggtcgtac agaaatatgg     180
cggttcctcg cttgagagtg cggaacgcat tagaaacgtc gctgaacgga tcgttgccac     240
caagaaggct ggaaatgatg tcgtggttgt ctgctccgca atgggagaca ccacggatga     300
acttctagaa cttgcagcgg cagtgaatcc cgttccgcca gctcgtgaaa tggatatgct     360
cctgactgct ggtgagcgta tttctaacgc tctcgtcgcc atggctattg agtcccttgg     420
cgcagaagcc caatctttca cgggctctca ggctggtgtg ctcaccaccg agcgccacgg     480
aaacgcacgc attgttgatg tcactccagg tcgtgtgcgt gaagcactcg atgagggcaa     540
gatctgcatt gttgctggtt tccagggtgt aataaagaa acccgcgatg tcaccacgtt     600
gggtcgtggt ggttctgaca ccactgcagt tgcgttggca gctgctttga acgctgatgt     660
gtgtgagatt tactcggacg ttgacggtgt gtataccgct gacccgcgca tcgttcctaa     720
tgcacagaag ctggaaaagc tcagcttcga agaaatgctg gaacttgctg ctgttggctc     780
caagattttg gtgctgcgca gtgttgaata cgctcgtgca ttcaatgtgc cacttcgcgt     840
acgctcgtct tatagtaatg atcccggcac tttgattgcc ggctctatgg aggatattcc     900
tgtggaagaa gcagtcctta ccggtgtcgc aaccgacaag tccgaagcca agtaaccgt      960 tctgggtatt tccgataagc caggcgaggc tgcgaaggtt ttccgtgcgt tggctgatgc    1020
agaaatcaac attgacatgg ttctgcagaa cgtctcttct gtagaagacg gcaccaccga    1080
catcatcttc acctgccctc gttccgacgg ccgccgcgcg atggagatct gaagaagct     1140 tcaggttcag ggcaactgga ccaatgtgct ttacgacgac caggtcggca agtctccct     1200 cgtgggtgct ggcatgaagt ctcacccagg tgttaccgca gagttcatgg aagctctgcg    1260
cgatgtcaac gtgaacatcg aattgatttc cacctctgag attcgtattt ccgtgctgat    1320
ccgtgaagat gatctggatg ctgctgcacg tgcattgcat gagcagttcc agctgggcgg    1380
cgaagacgaa gccgtcgttt atgcaggcac cggacgctaa agttttaaag gagtagtttt    1440
acaatgacca ccatcgcagt tgttggtgca accggccagg tcggccaggt tatgcgcacc    1500
cttttggaag agcgcaattt cccagctgac actgttcgtt tctttgcttc cccacgttcc    1560
gcaggccgta agattgaatt cgtcgacatc gatgctcttc tgcgttaatt aacaattggg    1620
atcctctaga cccgggattt aaatcgctag cgggctgcta aaggaagcgg aacacgtaga    1680
aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
```

```
agctagactg ggcggttta tggacagcaa gcgaaccgga attgccagct ggggcgccct    1860
ctggtaaggt tgggaagccc tgcaaagtaa actggatggc tttcttgccg ccaaggatct    1920
gatggcgcag gggatcaaga tctgatcaag agacaggatg aggatcgttt cgcatgattg    1980
aacaagatgg attgcacgca ggttctccgg ccgcttgggt ggagaggcta ttcggctatg    2040
actgggcaca acagacaatc ggctgctctg atgccgccgt gttccggctg tcagcgcagg    2100
ggcgcccggt tcttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacggcgagg    2520
atctcgtcgt gacccatggc gatgcctgct tgccgaatat catggtggaa aatggccgct    2580
tttctggatt catcgactgt ggccggctgg gtgtggcgga ccgctatcag gacatagcgt    2640
tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgagc gggactctgg ggttcgaaat gaccgaccaa gcgacgccca acctgccatc    2820
acgagatttc gattccaccg ccgccttcta tgaaaggttg gcttcggaa tcgttttccg    2880
ggacgccggc tggatgatcc tccagcgcgg ggatctcatg ctggagttct cgcccacgc    2940
tagcggcgcg ccggccggcc cggtgtgaaa taccgcacag atgcgtaagg agaaaatacc    3000
gcatcaggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaggc caggaaccgt aaaaaggccg    3180
cgttgctggc gttttccat aggctccgcc ccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta aaggacagt atttggtatc tgcgctctgc    3660
tgaagccagt taccttcgga aaaagagttg gtagctcttg atccggcaaa caaaccaccg    3720
ctggtagcgg tggttttttt gtttgcaagc agcagattac gcgcagaaaa aaggatctc    3780
aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900
gccgcggccg ccatcggcat tttcttttgc gttttattt gttaactgtt aattgtcctt    3960
gttcaaggat gctgtctttg acaacagatg ttttcttgcc tttgatgttc agcaggaagc    4020
tcggcgcaaa cgttgattgt ttgtctgcgt agaatcctct gtttgtcata tagcttgtaa    4080
tcacgacatt gtttcctttc gcttgaggta cagcgaagtg tgagtaagta aaggttacat    4140
```

```
cgttaggatc aagatccatt tttaacacaa ggccagtttt gttcagcggc ttgtatgggc    4200
cagttaaaga attagaaaca taaccaagca tgtaaatatc gttagacgta atgccgtcaa    4260 tcgtcattt  tgatccgcgg gagtcagtga acaggtacca tttgccgttc attttaaaga    4320
cgttcgcgcg ttcaatttca tctgttactg tgttagatgc aatcagcggt ttcatcactt    4380
ttttcagtgt gtaatcatcg tttagctcaa tcataccgag agcgccgttt gctaactcag    4440
ccgtgcgttt tttatcgctt tgcagaagtt tttgactttc ttgacggaag aatgatgtgc    4500
ttttgccata gtatgctttg ttaaataaag attcttcgcc ttggtagcca tcttcagttc    4560
cagtgtttgc ttcaaatact aagtatttgt ggcctttatc ttctacgtag tgaggatctc    4620
tcagcgtatg gttgtcgcct gagctgtagt tgccttcatc gatgaactgc tgtacatttt    4680
gatacgtttt tccgtcaccg tcaaagattg atttataatc ctctacaccg ttgatgttca    4740
aagagctgtc tgatgctgat acgttaactt gtgcagttgt cagtgtttgt ttgccgtaat    4800
gtttaccgga gaaatcagtg tagaataaac ggattttttcc gtcagatgta aatgtggctg    4860
aacctgacca ttcttgtgtt tggtctttta ggatagaatc atttgcatcg aatttgtcgc    4920
tgtctttaaa gacgcggcca gcgttttttcc agctgtcaat agaagtttcg ccgacttttt    4980
gatagaacat gtaaatcgat gtgtcatccg cattttttagg atctccggct aatgcaaaga    5040
cgatgtggta gccgtgatag tttgcgacag tgccgtcagc gttttgtaat ggccagctgt    5100
cccaaacgtc caggcctttt gcagaagaga tattttttaat tgtggacgaa tcaaattcag    5160
aaacttgata ttttttcattt ttttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340 acttttttgat gttcatcgtt catgtctcct tttttatgta ctgtgttagc ggtctgcttc    5400
ttccagccct cctgtttgaa gatggcaagt tagttacgca caataaaaaa agacctaaaa    5460
tatgtaaggg gtgacgccaa agtatacact ttgcccttta cacattttag gtcttgcctg    5520
ctttatcagt aacaaacccg cgcgatttac ttttcgacct cattctatta gactctcgtt    5580
tggattgcaa ctggtctatt ttcctctttt gtttgataga aaatcataaa aggatttgca    5640
gactacgggc ctaaagaact aaaaaatcta tctgtttctt ttcattctct gtatttttta    5700
tagtttctgt tgcatgggca taaagttgcc tttttaatca caattcagaa aatatcataa    5760
tatctcattt cactaaataa tagtgaacgg caggtatatg tgatgggtta aaaaggatcg    5820
gcggccgctc gatttaaatc tcgagaggcc tgacgtcggg                          5860
```